(12) United States Patent
Takaai et al.

(10) Patent No.: US 9,315,640 B2
(45) Date of Patent: Apr. 19, 2016

(54) POLYACRYLIC ACID-TYPE WATER ABSORBENT RESIN AND METHOD FOR PRODUCING SAME

(71) Applicant: Nippon Shokubai Co., Ltd., Osaka-shi (JP)

(72) Inventors: Toshihiro Takaai, Himeji (JP); Hidenori Wada, Himeji (JP); Sinichi Fujino, Himeji (JP)

(73) Assignee: Nippon Shokubai Co., Ltd., Osaka-Shi (JP)

(*) Notice: Subject to any disclaimer, the term of this patent is extended or adjusted under 35 U.S.C. 154(b) by 0 days.

(21) Appl. No.: 14/723,026

(22) Filed: May 27, 2015

(65) Prior Publication Data
US 2015/0259494 A1 Sep. 17, 2015

Related U.S. Application Data

(62) Division of application No. 13/807,530, filed as application No. PCT/JP2011/064951 on Jun. 29, 2011, now Pat. No. 9,074,030.

(30) Foreign Application Priority Data

Jun. 30, 2010 (JP) .................. 2010-149907

(51) Int. Cl.
| | | |
|---|---|---|
| C08J 9/12 | (2006.01) | |
| C08J 9/20 | (2006.01) | |
| A61L 15/24 | (2006.01) | |
| A61L 15/60 | (2006.01) | |
| C08F 220/06 | (2006.01) | |
| C08F 20/00 | (2006.01) | |
| C08J 3/24 | (2006.01) | |
| C08J 9/36 | (2006.01) | |
| C08F 2/01 | (2006.01) | |

(52) U.S. Cl.
CPC ............... *C08J 9/122* (2013.01); *A61L 15/24* (2013.01); *A61L 15/60* (2013.01); *C08F 2/01* (2013.01); *C08F 20/00* (2013.01); *C08F 220/06* (2013.01); *C08J 3/245* (2013.01); *C08J 9/20* (2013.01); *C08J 9/36* (2013.01); *C08J 2203/06* (2013.01); *C08J 2205/05* (2013.01); *C08J 2333/02* (2013.01); *C08J 2335/02* (2013.01); *Y10T 428/2982* (2015.01)

(58) Field of Classification Search
CPC .......... C08J 9/122; C08J 9/20; C08J 2203/06; C08J 2205/05; C08J 2333/02; C08J 3/245; C08J 9/36; C08J 2335/02; A61L 15/24; A61L 15/60; C08F 220/06; C08F 20/00; C08F 2/01; Y10T 428/2982
USPC ...................... 428/402; 524/78, 853; 427/212
See application file for complete search history.

(56) References Cited

U.S. PATENT DOCUMENTS

| | | |
|---|---|---|
| 4,703,067 A | 10/1987 | Mikita et al. |
| 4,857,610 A | 8/1989 | Chmelir et al. |
| 5,118,719 A | 6/1992 | Lind |
| 5,145,906 A | 9/1992 | Chambers et al. |
| 5,154,713 A | 10/1992 | Lind |
| 5,314,420 A | 5/1994 | Lind |
| 5,380,808 A | 1/1995 | Sumiya et al. |
| 5,399,591 A | 3/1995 | Smith et al. |
| 5,451,613 A | 9/1995 | Smith et al. |
| 5,462,972 A | 10/1995 | Smith et al. |
| 5,712,316 A | 1/1998 | Dahmen et al. |
| 5,750,585 A | 5/1998 | Park et al. |
| 5,856,370 A | 1/1999 | Chmelir |
| 5,985,944 A | 11/1999 | Ishizaki et al. |
| 6,107,358 A | 8/2000 | Harada et al. |
| 6,136,873 A | 10/2000 | Hähnle et al. |

(Continued)

FOREIGN PATENT DOCUMENTS

| | | |
|---|---|---|
| EP | 0303518 | 8/1987 |
| EP | 0496067 | 1/1991 |

(Continued)

*Primary Examiner* — Leszek Kiliman
(74) *Attorney, Agent, or Firm* — Cesari and McKenna LLP

(57) ABSTRACT

Provided is a method for producing a water absorbent resin, which promotes the formation of interconnected voids (continuous gas bubbles) in a foamed polymer (foam-like water absorbent resin) by a more convenient method, and produces with high efficiency a water absorbent resin which exhibits a high water absorption rate even when stepped into a sheet form or a powder form in hygiene articles and the like. Disclosed is a method for producing a polyacrylic acid-type water absorbent resin, comprising (A) a step of obtaining an aqueous solution of acrylic acid-type monomers containing gas bubbles dispersed therein; (B) a step of polymerizing the aqueous monomer solution and thereby obtaining a foamed polymer; and (C) a step of heating and drying the foamed polymer, wherein gas bubbles are incorporated such that the volumetric expansion factor defined by the following formula (1);

[Formula 1]

Volumetric expansion factor=(Volume of aqueous monomer solution after gas bubble dispersion)/(volume of aqueous monomer solution before gas bubble dispersion)   Formula (1);

exceeds 1.1 times, and the aqueous monomer solution having a monomer concentration defined by the following formula (2);

[Formula 2]

Monomer concentration [wt %]=(Weight of a monomer)/{(weight of a monomer)+(weight of solvent)}×100   Formula (2);

of 40% by weight or greater is boiling polymerized at a temperature of 100° C. or higher.

8 Claims, 6 Drawing Sheets

(56) References Cited

U.S. PATENT DOCUMENTS

| | | |
|---|---|---|
| 6,174,929 B1 | 1/2001 | Hahnle et al. |
| 6,174,978 B1 | 1/2001 | Hatsuda et al. |
| 6,245,410 B1 | 6/2001 | Hähnle et al. |
| 6,417,425 B1 | 7/2002 | Whitmore et al. |
| 6,455,600 B1 | 9/2002 | Hähnle et al. |
| 6,750,262 B1 | 6/2004 | Hähnle et al. |
| 9,074,030 B2 * | 7/2015 | Takaai ............ C08J 9/20 |
| 2005/0176834 A1 | 8/2005 | Hintz et al. |
| 2007/0123658 A1 * | 5/2007 | Torii ............ A61L 15/60 525/329.7 |
| 2007/0225422 A1 | 9/2007 | Sakamoto et al. |
| 2009/0177174 A1 | 7/2009 | Akiyama et al. |
| 2009/0318885 A1 | 12/2009 | Dairoku et al. |
| 2010/0240808 A1 * | 9/2010 | Wada ............ B01J 20/261 524/78 |
| 2010/0268181 A1 | 10/2010 | Ziemer et al. |

FOREIGN PATENT DOCUMENTS

| | | | |
|---|---|---|---|
| JP | 57-034101 | | 2/1982 |
| JP | 01-318021 | | 12/1989 |
| JP | A-1991-115313 | | 5/1991 |
| JP | 10-168129 | * | 6/1998 |
| JP | 2005-111474 | | 4/2005 |
| JP | 2009-247969 | | 10/2009 |
| WO | WO 94/22502 | | 10/1994 |
| WO | WO 2005/063313 | | 7/2005 |
| WO | WO 2009/048145 | | 4/2009 |
| WO | WO2009/048145 | * | 4/2009 |

* cited by examiner

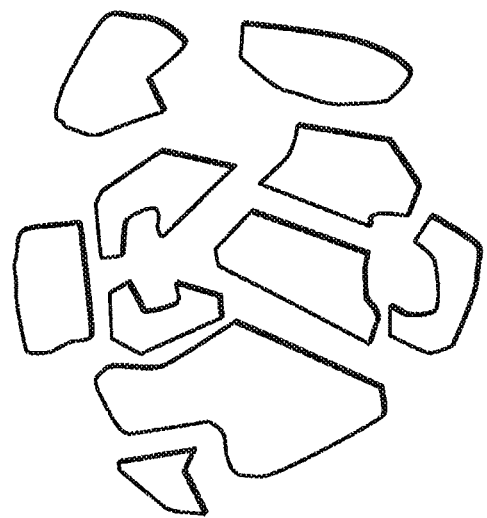
Fine pulverization
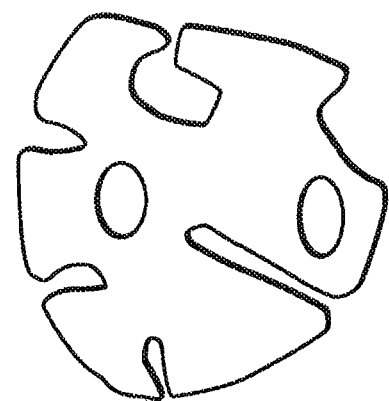
FIG.8

POLYACRYLIC ACID-TYPE WATER ABSORBENT RESIN AND METHOD FOR PRODUCING SAME

CROSS-REFERENCE TO RELATED APPLICATIONS

The present application is a divisional of commonly assigned copending U.S. patent application Ser. No. 13/807,530, filed on Dec. 28, 2012, which was a National Stage of International Application No. PCT/JP2011/064951, filed on Jun. 29, 2011, which claims the benefit of Japanese Application No. 2010-149907, filed on Jun. 30, 2010. All prior applications are hereby incorporated by reference in their entirety.

BACKGROUND OF THE INVENTION

1. Field of the Invention

The present invention relates to a polyacrylic acid-type water absorbent resin and a method for producing the same. More particularly, the present invention relates to the use of the water absorbent resin in hygiene products such as disposable diapers and sanitary napkins and the like, and to a foam-like polyacrylic acid-type water absorbent resin having improved water absorption performance (particularly, the water absorption rate), and a method for producing the same.

2. Background Information

Water absorbent resins are widely utilized in a variety of applications, such as hygiene products such as disposable diapers, sanitary napkins, and incontinence products for adults, and soil water retention agents, and thus, water absorbent resins are produced and consumed in large quantities. Known examples of such water absorbent resins include a partially neutralized crosslinked product of polyacrylic acid; a hydrolysate of a starch-acrylic acid graft polymer; a saponification product of a vinyl acetate-acrylic acid ester copolymer; a hydrolysate of an acrylonitrile copolymer or an acrylamide copolymer, or a crosslinked product thereof; and a crosslinked product of a cationic monomer, and the like. These water absorbent resins are produced by, for example, a method of polymerizing an aqueous solution containing a hydrophilic monomer while pulverizing the polymer gel by stirring (Patent Literature 1), methods of static polymerizing an aqueous solution containing a monomer (Patent Literatures 2 to 6), reverse phase suspension polymerization, or dropping polymerization, and the like.

In recent years, thin type hygiene products with smaller contents of cotton-like pulp are commercially available; however, the use amount of water absorbent resins has increased accordingly, so that there is a demand for a further improvement of the physical properties of water absorbent resins. Under such circumstances, an increase in the water absorption rate of water absorbent resins is desired, and a wide variety of technologies have been suggested by various water absorbent resin manufacturers (Patent Literatures 7 to 33). For example, a method of dispersing a large amount of gas bubbles in an aqueous monomer solution, and using a large amount of a surfactant, or optionally a gas bubble stabilizer, so as to prevent the disappearance of the gas bubbles until the initiation of polymerization (Patent Literatures 8, 20 and 21); a method of maintaining an aqueous monomer solution at a low temperature (Patent Literatures 7 and 9); and a method of producing a foam-like water absorbent resin (Patent Literatures 8, 20, 21, and 30 to 33) have been suggested.

Furthermore, foaming polymerization is carried out for the purpose of enhancing the water absorption rate through an increase in the surface area, and in regard to this foaming polymerization, specifically, as a foaming agent that is used for the monomer, a technology of using a carbonic acid salt (Patent Literatures 10 to 17); a technology of using an organic solvent (Patent Literatures 18 and 19); a technology of using an inert gas (Patent Literature 22); a technology of using an azo compound (Patent Literatures 23 and 24); a technology of using an insoluble inorganic powder (Patent Literature 25), and the like are known. Furthermore, a technology of carrying out foam formation and crosslinking after polymerization (Patent Literature 26), a technology of using water-insoluble particles in the polymerization (Patent Literature 27), a technology of performing polymerization in a state in which precipitates of an acrylic acid sodium salt are dispersed (Patent Literature 28), and the like have been proposed.

Furthermore, in the method of producing a foam-like water absorbent resin, the purport of recommending "avoidance of boiling at the time of polymerization" (Patent Literatures 8, 20, 21, and 30 to 32) has been disclosed, or "polymerization at or below 65° C." (Patent Literature 33) has been disclosed.

In addition, in regard to polymerization other than foaming polymerization, a technology of controlling the maximum temperature to be low for the purpose of reducing a soluble fraction or the like has been disclosed. Specifically, a technology of adjusting the maximum temperature to 95° C. or lower (Patent Literature 34), a technology of performing polymerization at a polymerization temperature of 20° C. to 70° C. (Patent Literature 35), and a technology of performing polymerization at a polymerization temperature of 20° C. to 95° C. (Patent Literature 36) have been proposed.

However, in the method of dispersing a large amount of gas bubbles by using a large amount of a surfactant, at least continuous gas bubbles are formed by polymerization, but a relatively long time is required for the dispersion of gas bubbles. Also, when a water absorbent resin produced by that method is used in hygiene products, the interface (surface) tension of the body fluid is decreased by the large amount of surfactant, and therefore, there is a problem that the liquid absorption characteristics of the hygiene products are impaired, and the amount of re-wetting increases. Furthermore, in the method of maintaining an aqueous monomer solution at a low temperature, since a long time is required for polymerization, productivity becomes poor, and also, there is a problem that there is almost no interconnection of gas bubbles (continuous gas bubbles) in the obtained porous polymer, and the extent of increase in the water absorption rate becomes low in spite of the decrease in the bulk density. Furthermore, in the step of foaming polymerization by which polymerization of a monomer is carried out, with gas bubbles dispersed in the monomer, which has been suggested in the past in the Patent Literatures described above and the like, an excessive decrease in the bulk density occurs, so that the transportation cost and the storage cost are increased. Also, there are also problems of deterioration of physical properties caused by a decrease in the impact resistance of the water absorbent resin powder, and powder dust generation.

As discussed above, many methods for increasing the water absorption rate have been proposed as in Patent Literatures 7 to 33 and the like; however, these methods require expensive production facilities, exhibit low productivity, or are accompanied by an increase in the cost due to the use of large amounts of surfactants, or by a decrease in the surface tension of the water absorbent resin (and a consequent increase in the amount of re-wetting of diapers). In addition, these methods still bring about insufficient formation of foams, and further foaming causes impairment of the water absorption characteristics (for example, water absorption capacity under load, liquid permeability, extractable polymer content, and residual monomer), or, since the volumetric expansion factor caused by foaming is high, the bulk density is excessively decreased, and thereby, fine powders increase. Furthermore, the "avoidance of boiling at the time of polymerization" that is recommended in Patent Literatures 8, 20, 21 and 30 to 33, and the like causes a decrease in productivity or requires expensive cooling facilities and the like.

Furthermore, since water absorbent resins are generally in the form of powder (particulate form), when the water absorbent resins are actually used in disposable diapers, sanitary napkins, tampons, and the like, it is necessary to manufacture the powdered (particulate) water absorbent resin into a sheet form, a cylindrical form or the like after mixing a water absorbent resin with a fibrous material or an adhesive as necessary. Such manufacturing process causes not only an increase in the cost, but also a decrease in the water absorption rate or powder destruction (generation of fine powder).

Also, in addition to the problem of the water absorption rate, water absorbent resins are mainly used in hygiene materials, and along with the increase in the use amount (g or % by weight) per one hygiene material, the degree of whiteness of the water absorbent resin itself is more emphasized, so that the problem of coloration is also increasing. Thus, Patent Literature 29 discloses a method for preventing coloration by using an acrylic acid ammonium salt in the monomer, or a method of preventing coloration by adding a compound containing a phosphorus atom or a sulfur-based reducing agent multiple times.

Furthermore, while water-containing gel-like crosslinked polymers obtainable by polymerizing an aqueous monomer solution require large facilities or a large amount of heat energy, and a long drying time for drying of the polymer, there are also problems such as deterioration or coloration of the water absorbent resins caused by drying for a long time, and an increase in the production cost for the water absorbent resins. Today, shortening of the drying time is an important problem to be addressed for the water absorbent resins, from the viewpoints of cost, physical properties, and coloration.

Also, while conventional water absorbent resins are primarily in the form of powder, in the case of using the water absorbent resins as absorbing articles such as disposable diapers (final consumption materials), there is a problem that a step of fixing or incorporating a water absorbent resin powder into an absorbing article may be needed, an expensive adhesive for the fixation should be used, and powder may be dropped-out or migrate.

In order to solve such problems with powder, a water absorbent resin molded product in the form of sheet etc. or a composite have also been suggested (Patent Literatures 37 and 38). However, complicated steps or expensive auxiliary raw materials are needed for molding, and also, since molded products such as a sheet form have greatly decreased specific surface areas as compared with powders, such molded products have insufficient water absorption rate and insufficient gas permeability, and cause leakage or stuffiness of disposable diapers and the like.

CITATION LIST

Patent Literature

Patent Literature 1: Japanese Patent Application Laid-Open (JP-A) No. 57-034101
Patent Literature 2: U.S. Pat. No. 4,857,610
Patent Literature 3: EP 0 303 518 B
Patent Literature 4: U.S. Pat. No. 5,145,906
Patent Literature 5: U.S. Pat. No. 5,380,808
Patent Literature 6: EP 0 496 067 B
Patent Literature 7: U.S. Pat. No. 5,118,719
Patent Literature 8: U.S. Pat. No. 6,174,929
Patent Literature 9: U.S. Pat. No. 6,107,358
Patent Literature 10: U.S. Pat. No. 5,118,719
Patent Literature 11: U.S. Pat. No. 5,154,713
Patent Literature 12: U.S. Pat. No. 5,314,420
Patent Literature 13: U.S. Pat. No. 5,399,591
Patent Literature 14: U.S. Pat. No. 5,451,613
Patent Literature 15: U.S. Pat. No. 5,462,972
Patent Literature 16: U.S. Pat. No. 5,712,316
Patent Literature 17: WO 2005/063313 A
Patent Literature 18: WO 94/022502 A
Patent Literature 19: U.S. Pat. No. 4,703,067
Patent Literature 20: U.S. Pat. No. 6,136,873
Patent Literature 21: U.S. Pat. No. 6,750,262
Patent Literature 22: U.S. Pat. No. 6,107,358
Patent Literature 23: U.S. Pat. No. 5,856,370
Patent Literature 24: U.S. Pat. No. 5,985,944
Patent Literature 25: US 2010/0268181
Patent Literature 26: US 2005/0176834
Patent Literature 27: US 2007/0225422
Patent Literature 28: JP 1-318021 A
Patent Literature 29: US 2009/318885
Patent Literature 30: U.S. Pat. No. 6,750,262
Patent Literature 31: U.S. Pat. No. 6,455,600
Patent Literature 32: U.S. Pat. No. 6,245,410
Patent Literature 33: U.S. Pat. No. 5,750,585
Patent Literature 34: U.S. Pat. No. 6,174,978
Patent Literature 35: U.S. Pat. No. 5,380,808
Patent Literature 36: EP 0 496 067 B
Patent Literature 37: US 2009/0177174
Patent Literature 38: U.S. Pat. No. 6,417,425

SUMMARY OF THE INVENTION

Technical Problem

A problem to be solved by the present invention is to increase the water absorption rate of a water absorbent resin, and particularly, to increase the water absorption rate through foaming or transition into porous formation. More preferably, the problem is to promote the formation of interconnected voids (continuous gas bubbles) in a foamed polymer (foam-like water absorbent resin) by a more convenient method, and to simplify the drying step for the water absorbent resin.

That is, the problem is to provide a water absorbent resin which has a high water absorption rate even in the form of sheet (molded product) or in the form of powder in hygiene products and the like, and a highly efficient production method for the water absorbent resin.

Solution to Problem

In order to solve the problem described above, the inventors paid attention to the dispersion of gas bubbles in the monomer at the time of polymerization and to the polymerization method, and found that the problem may be solved by using a particular method, thus completing the present invention.

That is, in order to solve the problem described above, the method for producing a water absorbent resin of the present invention provides a method for producing a polyacrylic acid-type water absorbent resin, comprising (A) a step of obtaining an aqueous solution of acrylic acid-type monomers containing gas bubbles dispersed therein; (B) a step of polymerizing the aqueous monomer solution and thereby obtaining a foamed polymer; and (C) a step of heating and drying the foamed polymer, wherein gas bubbles are incorporated such that the volumetric expansion factor defined by the following formula (1);

[Formula 1]

Volumetric expansion factor [times]=(Volume of aqueous monomer solution after gas bubble dispersion)/(volume of aqueous monomer solution before gas bubble dispersion)    Formula (1)

exceeds 1.1 times, and the aqueous monomer solution having a monomer concentration defined by the following formula (2);

[Formula 2]

Monomer concentration [wt %]=(Weight of a monomer)/{(weight of a monomer)+(weight of solvent)}×100    Formula (2);

of 40% by weight or greater is boiling polymerized at a temperature of 100° C. or higher.

Furthermore, the present invention provides a polyacrylic acid-type water absorbent resin having an open gas bubble ratio of 5% or greater.

Advantageous Effects of the Invention

According to the method for producing a water absorbent resin of the present invention, the water absorption rate of a water absorbent resin is enhanced by foaming. As a preferred embodiment, a water absorbent resin having continuous gas bubbles can also be obtained. When the water absorbent resin of the present invention is used, since the open gas bubble ratio is high, the water absorption rate and the gas permeability of the water absorbent resin are enhanced.

BRIEF DESCRIPTION OF THE DRAWINGS

FIG. 8 is a schematic diagram illustrating an example of the method for determining the true specific gravity of a water absorbent resin.

DETAILED DESCRIPTION

Figure 1:
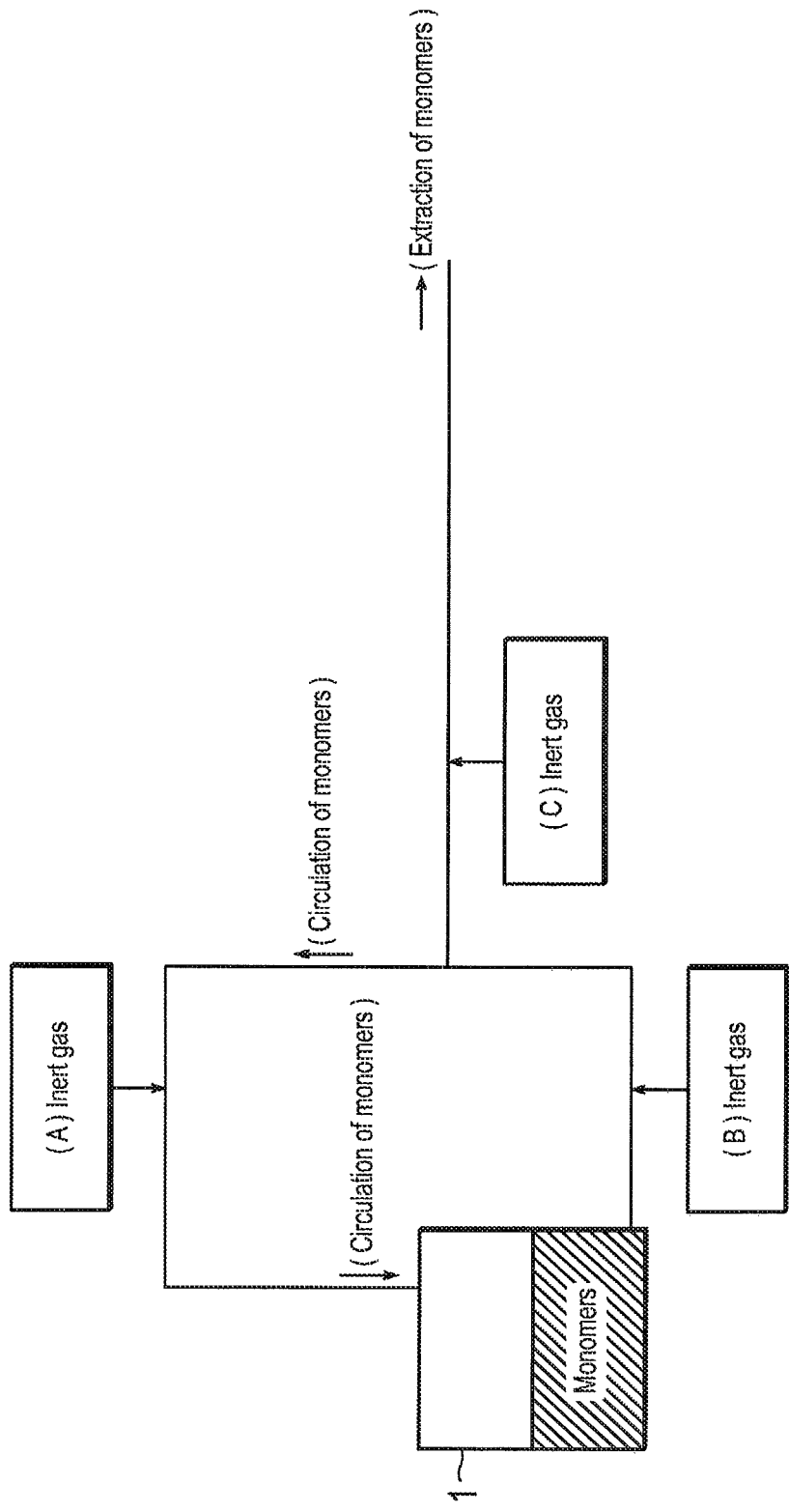
FIG. 1 is a flow diagram illustrating an example of a foam stabilizing step of circulating an aqueous monomer solution containing an inert gas in a circulating tank.

Hereinafter, the method for producing a polyacrylic acid-type water absorbent resin according to the present invention will be described in detail. However, the scope of the present invention is not intended to be restrained by these descriptions, and in addition to the following examples, the present invention can be appropriately modified and carried out to the extent that the purport of the present invention is not impaired.

Specifically, the present invention is not intended to be limited to the embodiments described below, and various modifications can be made within the scope disclosed in the claims. Embodiments obtainable by appropriately combining the technical means respectively disclosed in different embodiments are also included in the technical scope of the present invention.

[1] Definition of Terms (1-1) "Water Absorbent Resin"

The "water absorbent resin" according to the present invention means a water-swellable, water-insoluble polymer gelling agent, and the "water absorbent resin powder" means a water absorbent resin that has been pulverized into a powder form. Meanwhile, the term "water-swellable" means that the CRC (water absorption capacity without load) defined in ERT441.2-02 is 5 [g/g] or higher, preferably 10 to 100 [g/g], and more preferably 20 to 80 [g/g]. Also, the term "water-insoluble" means that the Ext (extractables) defined in ERT470.2-02 is 0% to 50% by weight, preferably 0% to 30% by weight, more preferably 0% to 20% by weight, and particularly preferably 0% to 10% by weight.

The water absorbent resin can be appropriately designed in accordance with the use, and although there are no particular limitations, a hydrophilic crosslinked polymer obtained by crosslinking polymerizing an unsaturated monomer having a carboxyl group is preferred. Furthermore, the water absorbent resin is not limited to the form in which the entire amount (100% by weight) is composed of a polymer, and the water absorbent resin may also contain additives and the like as other components in addition to the water absorbent resin, to the extent that the performance described above is maintained. That is, even a water absorbent resin composition containing a water absorbent resin powder and additives is also collectively referred to as a water absorbent resin in the present invention. The content of the polyacrylic acid (salt)-type water absorbent resin is preferably 70% to 99.9% by weight, more preferably 80% to 99.7% by weight, and still more preferably 90% to 99.5% by weight, relative to the total amount. Regarding the other components in addition to the water absorbent resin, water is preferred from the viewpoints of the water absorption rate and the impact resistance of the powder (particles), and additives are included as necessary.

(1-2) "Polyacrylic Acid-Type Water Absorbent Resin", "Foam-Like Water Absorbent Resin", and "Water Absorbent Resin Molded Product"

The "polyacrylic acid-type water absorbent resin" according to the present invention means a water absorbent resin which contains an arbitrary graft component, and contains, as a main component, acrylic acid and/or a salt thereof (hereinafter, referred to as acrylic acid (salt)) as a repeating unit.

Specifically, the polyacrylic acid-type water absorbent resin refers to a polymer containing acrylic acid (salt) in an amount of 50% to 100% by mole among all the monomers used in polymerization (excluding the crosslinking agent), and refers to a water absorbent resin containing acrylic acid (salt) in an amount of preferably 70% to 100% by mole, more preferably 90% to 100% by mole, and particularly preferably substantially 100% by mole. Furthermore, the salt as a polymer essentially includes water-soluble salts, and preferably includes a monovalent salt, more preferably an acrylic metal salt or an ammonium salt, particularly an alkali metal salt, and further sodium salt.

Furthermore, such a water absorbent resin which is in the form of foam (expanded) or in a porous form is called "foam-like water absorbent resin", and the shape (a sheet shape, a block shape, a powder shape or the like) does not matter.

Meanwhile, in the present invention, a hydro gel that has been heated and dried is referred to as a water absorbent resin dried product.

Meanwhile, with regard to powdered (particulate) water absorbent resins, a water absorbent resin having a certain shape such as a sheet shape, a block shape or a cylindrical shape may be particularly referred to as a water absorbent resin molded product in the following descriptions, and a representative example may be a sheet-form water absorbent resin.

(1-3) "Open Gas Bubble" and "Independent Gas Bubble"

Figure 7:
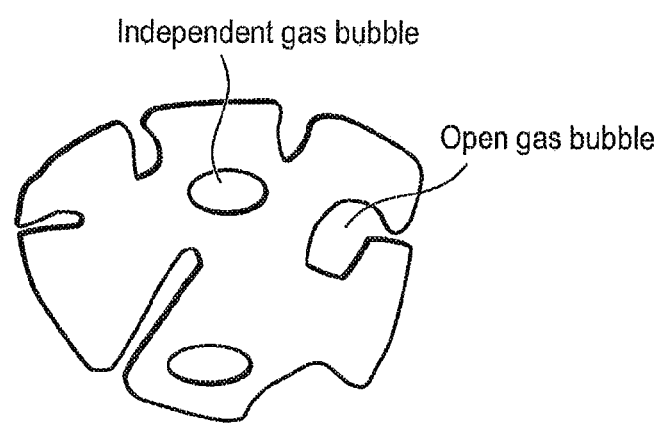
FIG. 7 is a conceptual diagram of open gas bubbles and independent gas bubbles.

According to the present invention, the "open gas bubble" (also called continuous gas bubble) refers to a gas bubble that is not completely surrounded by a wall of the water absorbent resin (a gas bubble that are interconnected with the outside of the water absorbent resin), and the "independent gas bubble" refers to a gas bubble that is completely surrounded in the interior of the water absorbent resin by a wall of the water absorbent resin. FIG. 7 presents a conceptual diagram of open gas bubbles and independent gas bubbles.

(1-4) "EDANA" and "ERT"

"EDANA" is an abbreviation of the European Disposables and Nonwovens Association, and "ERT" is an abbreviation of measurement method for a water-absorbent resin of an European standard (nearly a world standard) (EDANA Recommended Test Method).

Meanwhile, according to the present invention, unless particularly stated otherwise, the physical properties of a water absorbent resin powder are measured according to the original document of ERT (published document: revised in 2002).

(a) "CRC" (ERT441.2-02)

"CRC" is an abbreviation of Centrifuge Retention Capacity, and means water absorption capacity without load (it may also be referred to simply "water absorption capacity"). Specifically, it is water absorption capacity (unit; g/g) after immersing 0.2 g of a water-absorbent resin powder in a non-woven bag in an excess amount of an aqueous 0.9% by weight sodium chloride solution for 30 minutes, and then draining water therefrom with a centrifugal separating machine.

(b) "AAP" (ERT442.2-02)

AAP is an abbreviation of Absorption Against Pressure, and means water absorption capacity under load. Specifically, it means water absorption capacity (unit; g/g) after swelling 0.9 g of a water-absorbent resin with an excess amount of an aqueous 0.9% by weight sodium chloride solution under a load of 2.06 kPa (0.3 psi, 21 [g/cm$^2$]) for 1 hour. Meanwhile, in ERT442.2-02, the "AAP" is indicated as Absorption Under Pressure, but the meaning is substantially identical. Furthermore, the measurement may also be made by changing only the load conditions to 4.83 kPa (0.7 psi, 50 [g/cm$^2$]).

(c) "Ext" (ERT470.2-02)

"Ext" is an abbreviation of Extractables, and means a water-soluble content (amount of water-solubles). Specifically, it is a value (unit; % by weight) obtained by stirring 1 g of a water-absorbent resin powder in 200 g of an aqueous 0.9% by weight sodium chloride solution for 16 hours at 500 rpm, and measuring an amount of dissolved polymer by pH titration.

(d) "PSD" (ERT420.2-02)

"PSD" is an abbreviation of Particle Size Distribution, and means a particle size distribution measured by sieve classification. A weight average particle diameter (D50) and a particle size distribution width are measured by a method similar to "(1) Average Particle Diameter and Distribution of Particle Diameter" described in WO 2004/69915 A.

(1-5) "Liquid Permeability"

"Liquid permeability" means the flow properties of a liquid that flows between the particles of a swollen water absorbent resin powder under a load or without load. Representative measurement methods for this "liquid permeability" include SFC (Saline Flow Conductivity) and GBP (Gel Bed Permeability).

"SFC (saline flow conductivity)" means the liquid permeability of a 0.69 wt % saline solution in 0.9 g of a water absorbent resin powder under a load of 2.07 kPa (0.3 psi). This is measured according to the SFC test method described in U.S. Pat. No. 5,669,894.

"GBP (gel bed permeability)" means liquid permeability of a 0.69 wt % physiological saline for a water absorbent resin powder under a load or in free expansion. This is measured according to the GBP test method described WO 2005/016393 A.

(1-6) Others

In the present description, "X to Y" showing a range indicates to be equal to or higher than X and equal to or lower than Y. Also, "t (ton)" as a unit of weight means "Metric Ton". Unless otherwise specified, "ppm" should mean "ppm by weight". In the present description, "mass", "% by mass" and "parts by mass" are used synonymously to "weight", "% by weight" and "parts by weight", respectively. Still more, physical properties or the like is measured at room temperature (20 to 25° C.)/a relative humidity of 40 to 50%, unless otherwise specified. Furthermore, the term " . . . acid (salt)" means " . . . acid and/or salt thereof", and "(meth)acrylic" means "acrylic and/or methacrylic".

[2] Method for Producing Polyacrylic Acid-Type Water Absorbent Resin

The polyacrylic acid-type water absorbent resin according to the present invention can be produced by, for example, the following method. Such a production method can be suitably applied to continuous production.

Here, a gas used in the present invention for the production of gas bubbles refers to a compound which itself is gaseous at normal temperature before use, and this is a concept different from a solid foaming agent that generates gas at the time of polymerization or the like (for example, a carbonate, or an azo compound). Therefore, in the present invention, an aqueous solution of acrylic acid-type monomers containing gas bubbles dispersed therein is formed by directly mixing a gas, preferably an inert gas, with an aqueous monomer solution or raw materials thereof (an individual monomer and a solvent).

(2-1) (A) a Step of Obtaining Aqueous Solution of Acrylic Acid-Type Monomers Containing Gas Bubbles Dispersed Therein (Dispersion Step)

(Composition of a Monomer)

A monomer used in the present invention is not particular limited as long as the monomer is capable of forming a water absorbent resin when polymerized, but in view of properties, acrylic acid (salt) is used, and further examples include the compounds listed below. Examples thereof include an anionic unsaturated monomer such as (meth)acrylic acid, (anhydrous) maleic acid, itaconic acid, cinnamic acid, vinylsulfonic acid, allyltoluenesulfonic acid, vinyltoluenesulfonic acid, styrenesulfonic acid, 2-(meth)acrylamido-2-methylpropanesulfonic acid, 2-(meth)acryloylethanesulfonic acid, 2-(meth)acryloylpropanesulfonic acid, 2-hydroxyethyl (meth)acryloyl phosphate, and a salt thereof; a mercapto group-containing unsaturated monomer; a phenolic hydroxyl group-containing unsaturated monomer; an amide group-containing unsaturated monomer such as (meth)acrylamide, N-ethyl (meth)acrylamide, and N,N-dimethyl (meth)acrylamide; and an amino group-containing unsaturated monomer such as N,N-dimethylaminoethyl (meth)acrylate, N,N-dimethylaminopropyl (meth)acrylate, and N,N-dimethylaminopropyl (meth)acrylamide, and the like.

In addition to those described above, in order to improve a property such as flexibility of the foam-like polymer (foamed polymer) thus obtainable, other monomers may also be used in combination. Regarding the monomer to be used in combination, use of water-soluble or hydrophobic unsaturated monomers such as 2-hydroxyethyl (meth)acrylate, methoxypolyethylene glycol (meth)acrylate, polyethylene glycol (meth)acrylate, isobutylene, lauryl (meth)acrylate, and the like as a copolymer component is also included.

These monomers may be used singly, or two or more kinds may be used in combination. However, from the viewpoints of the performance of the resulting water absorbent resin powder and cost, a polyacrylic acid-type water absorbent resin which use an acrylic acid-type monomer including acrylic acid and/or salts thereof (for example, a salt such as a sodium salt, a lithium salt, a potassium salt, an ammonium salt, and amines is preferred, and among these, a sodium salt is more preferred in view of cost) is preferred.

The use amount of acrylic acid and/or a salt thereof as the polyacrylic acid-type water absorbent resin is 50% by mole or greater, preferably 70% by mole or greater, more preferably 80% by mole or greater, still more preferably 90% by mole or greater, and particularly preferably 95% by mole or greater (the upper limit is 100% by mole), relative to the total amount of monomer components (excluding the internal crosslinking agent that will be described below), and most preferably, the use amount is substantially 100% by mole. Meanwhile, polyacrylic acid as used in the present invention is a concept including polyacrylic acid salts (particularly a monovalent salt).

(Methoxyphenol Compound)

In the method for producing a water absorbent resin according to the present invention, a monomer containing a methoxyphenol compound in an amount of 200 ppm or less, relative to the content of acrylic acid, is preferably used. The main component of this monomer may be acrylic acid, or may also be acrylic acid and an acrylic acid salt. Specific examples of the methoxyphenols include o-, m-, p-methoxyphenol, and a methoxyphenol compound which is these methoxyphenol having one substituent or two or more substituents such as a methyl group, a t-butyl group, and a hydroxyl group. Particularly preferably, p-methoxyphenol is used in the present invention.

The content of the methoxyphenol compound is preferably 200 ppm by weight or less, more preferably 10 ppm to 200 ppm, still more preferably 10 ppm to 120 ppm, particularly preferably 10 ppm to 90 ppm, and most preferably 20 ppm to 90 ppm, in an acrylic acid equivalent. When the content of the methoxyphenol compound is 200 ppm or less, coloration (yellow tint/yellowing) of the water absorbent resin thus obtained can be suppressed. Furthermore, if the content of the methoxyphenol compound is less than 10 ppm, that is, if the methoxyphenol compound which is a polymerization inhibitor has been removed by purification such as distillation, there is a risk that polymerization may occur before polymerization is intentionally initiated, and also, weather resistance of a water absorbent resin obtained by using acrylic acid (salt) as a main raw material may be poor.

The main component of the monomer is acrylic acid and/or an acrylic acid salt, but these acrylic acid and acrylic acid salts have different molecular weights. In the present invention, the value relative to the content of acrylic acid is defined in consideration of this difference of molecular weights. The value relative to the content of acrylic acid is the content ratio by weight (weight ratio) of those trace amount components relative to the weight of acrylic acid in the case where all the acrylic acid salts are assumed as an equimolar amount of unneutralized acrylic acid. That is, for example, the content of sodium acrylate (molecular weight 94) after neutralization is calculated on a weight basis relative to the content of acrylic acid (molecular weight 72), and the content ratio (weight ratio) of the methoxyphenol compound and the like is defined based on the weight after the calculation relative to the content of acrylic acid (calculation is made based on 72 instead of 94). That is, in regard to the water absorbent resin obtained after polymerization, when a partially neutralized or completely neutralized acrylic acid salt has formed a polymer, the value relative to the content of acrylic acid can be calculated such that the partially neutralized or completely neutralized polyacrylic acid salt is assumed as an equimolar amount of unneutralized polyacrylic acid. The term "partially neutralized" as described above means that the neutralization rate is greater than 0% by mole and less than 100% by mole. The term "completely neutralized" as described above means that the neutralization rate is 100% by mole. The term "unneutralized" means that the neutralization rate is 0% by mole.

As described above, it is preferable that the method for producing a water absorbent resin of the present invention is a method for producing a water absorbent resin, which involves polymerization of an aqueous monomer solution containing 200 ppm or less of a methoxyphenol compound (particularly, p-methoxyphenol). Furthermore, when the aqueous monomer solution goes through the polymerization step (concentration, initiator, and temperature) and the hydro gel goes through the drying step (temperature, time, solids content, amount of airflow, and the like), a predetermined amount of the methoxyphenol compound is consumed, so that a water absorbent resin containing a methoxyphenol compound (particularly, p-methoxyphenol) in an amount of preferably 60 ppm or less, and more preferably 5 ppm to 60 ppm, particularly a water absorbent resin containing a methoxyphenol compound uniformly in the interior of the polymer, can be obtained.

That is, the production method of the present invention may be a production method in which the content of a methoxyphenol compound (particularly, p-methoxyphenol) in the water absorbent resin obtainable by the polymerization step and drying step is adjusted to 60 ppm or less by using a monomer having a content of a methoxyphenol compound (particularly, p-methoxyphenol) of 200 ppm or less.

In regard to the methoxyphenol compound at the time of polymerization, in the case of making calculations by taking acrylic acid (molecular weight 72) as the reference, the acrylic acid salt obtained by neutralization as necessary has an increased molecular weight (for example, in the case of a 75 mol %-neutralized sodium salt, the molecular weight is 88.5), and the content of the methoxyphenol compound is decreased. Furthermore, by taking the consumption at the time of polymerization into consideration as well, in the present invention, it is preferable to adjust the content of methoxyphenol compound in the polyacrylic acid salt thus obtained to 60 ppm or less, while the content of methoxyphenol compounds in the acrylic acid salt before polymerization is 200 ppm or less.

Meanwhile, the method for controlling the methoxyphenol compound in the water absorbent resin is not limited to the example described above, and the methods described below may also be mentioned as other techniques. These methods may also be used in combination.

Production method 1: a method of polymerizing a monomer in the absence of a methoxyphenol compound, or a monomer containing less than 10 ppm of a methoxyphenol compound, drying the polymer, and then adding a predetermined amount of a methoxyphenol compound.

Production method 2: a method of polymerizing a monomer containing an excess amount of a methoxyphenol compound into a water absorbent resin, and then removing a predetermined amount of a methoxyphenol compound by washing before drying. Meanwhile, washing can be achieved by using water or a water-alcohol mixture.

Furthermore, for the monomer used in the present invention, a polymerization inhibitor other than methoxyphenol compounds may be used in the production step, and the polymerization inhibitor may also be used in combination with methoxyphenol compounds.

As the polymerization inhibitor other than methoxyphenol compounds, for example, phenothiazine, hydroquinone, copper salts, manganese acetate, methylene blue, and the like are effective. However, unlike methoxyphenol compounds, since these polymerization inhibitors inhibit polymerization, a smaller final amount is better. When the polymerization inhibitor is used in combination with methoxyphenol compounds, the concentration thereof in the monomer is preferably 0.01 ppm to 10 ppm.

It should be noted that quantitative determination of the components described above can be carried out by liquid chromatography or gas chromatography. Particularly, in the present invention, the content of a methoxyphenol compound is such that a value measured by the methods of Examples as described below is employed.

(Monomer Concentration)

The monomer concentration at the time of polymerization is 40% by weight or greater, more preferably 45% by weight or greater, still more preferably 50% by weight or greater, and particularly preferably 53% by weight or greater. The upper limit is not particularly limited, but the upper limit is preferably 80% by weight or less, and more preferably 75% by weight or less. Meanwhile, in the present invention, the monomer concentration is defined by the following formula (2):

[Formula 3]

$$\text{Monomer concentration [wt \%]} = (\text{Weight of a monomer})/\{(\text{weight of a monomer}) + (\text{weight of a solvent})\} \times 100 \quad \text{Formula (2)}$$

The (weight of a monomer) in the above formula (2) represents the total weight of monomers present in the aqueous monomer solution. For example, as in the case of Examples described below, in the case of using acrylic acid and sodium hydroxide for neutralizing acrylic acid when an aqueous monomer solution is prepared, the value obtained by subtracting the water amount generated by the neutralization reaction from the total amount of acrylic acid and sodium hydroxide (total weight of acrylic acid and sodium acrylate present in the aqueous monomer solution) will be the (a weight of monomer) in the formula (2). Furthermore, when an aqueous monomer solution is prepared, in the case of using acrylic acid and sodium acrylate, the total amount of acrylic acid and sodium acrylate will be the (weight of a monomer) in the formula (2).

Also, the (weight of solvent) in the above formula (2) represents the amount of solvent in the case where the raw materials supplied to the polymerization system are supplied in the state of solution such as an aqueous solution. Therefore, the surfactant, hydrophilic polymer and the like that will be described below, which are used as necessary, are not taken into consideration in the definition (calculation) of the monomer concentration.

If the monomer concentration at the time of polymerization is less than 40% by weight, not only the productivity is lowered, but the stability of gas bubbles dispersed in the aqueous monomer solution is also poor, and the gas bubbles are easy to be defoamed during polymerization. Therefore, it is not preferable. Meanwhile, in a high concentration region where the monomer concentration at the time of polymerization is 40% by weight or greater, preferably 42% by weight or greater, more preferably 43% by weight or greater, still more preferably 45% by weight or greater, and particularly preferably 50% by weight or greater, the interconnectivity of bubbles (continuous bubble formability) is increased even under the conditions other than as defined in the present invention. Therefore, there lies the superiority of the present invention. The solvent for the monomers is water, and a small amount (for example, in the range of greater than 0% by weight and less than or equal to 30% by weight, further in the range of greater than 0% by weight and less than or equal to 10% by weight, relative to the total amount of solvent) of an organic solvent may also be used together, in addition to water. Examples of the organic solvent include alcohols such as methyl alcohol, ethyl alcohol, n-propyl alcohol, isopropyl alcohol, n-butyl alcohol, isobutyl alcohol, t-butyl alcohol, and the like.

As in the case of Patent Literature 28 (JP 1-318021 A), polymerization in the form of a slurry of a monomer (aqueous dispersion liquid of an acrylic acid salt) may deteriorate the physical properties (water absorption capacity, extractable polymer content, residual monomer, and the like). Therefore, in the present invention, when the monomer described above is an acid group-containing monomer, the neutralization rate is adjusted to the extent that neutralized salts are not precipitated out in the aqueous monomer solution. That is, not an aqueous dispersion liquid of an acrylic acid-type monomer, but an aqueous solution of an acrylic acid-type monomer is polymerized in the present invention. Since precipitation of neutralized salts may vary depending on the solubility of the neutralized salts in water, the monomer concentration, the neutralization rate, temperature, pressure, the base used for neutralization, and the dispersant (a surfactant, another monomer, or a water-soluble polymer) that is optionally used and so on, even for the same monomer, the temperature of the aqueous monomer solution may increase, causing an increase in the solubility of the monomer. Thus, the precipitation of neutralized salts is appropriately determined, and depends on those conditions.

Since according to the present invention, polymerization is carried out in a relatively short time in the state in which gas bubbles are dispersed in an aqueous monomer solution to make the surface area of the liquid large, while water is evaporated, if a salt of a monomer, for example, sodium acrylate, has been precipitated out before polymerization, most of the salt remains behind even after the polymerization without being dissolved, and therefore, it is not preferable. Furthermore, if the salt precipitated out during polymerization is dissolved, evaporation of water is suppressed, and a time for the salt to be dissolved is required. Thus, the polymerization time must be adjusted to be relatively longer. In this case, the degree of foaming, among others, the interconnectivity of gas bubbles (continuous gas bubble formability) which is a preferred embodiment, is markedly decreased. Regarding the neutralization described above, if necessary, it is still acceptable to neutralize the polymer gel obtained after polymerization. However, for the applications which have a possibility of being brought into contact with a human body, such as hygiene products, neutralization after polymerization should be avoided as far as possible. For the use in hygiene products and the like, the neutralization rate of the monomers or the polymer gel is preferably 40% to 90% by mole, and more preferably 50% to 80% by mole.

(Internal Crosslinking Agent)

On the occasion of polymerization, an internal crosslinking agent is used according to necessity. As such an internal crosslinking agent, conventionally known internal crosslinking agents can be used. Specific examples thereof include N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate, and the like. Among these, one kind or two or more kinds can be used in consideration of reactivity. Among them, it is preferable to use a compound having two or more polymerizable unsaturated groups.

The use amount of the above internal crosslinking agent can be appropriately determined by the desired physical properties of the water absorbent resin, but usually, the use amount is preferably 0.0001% to 3% by mole, more preferably 0.0005% to 2% by mole, and still more preferably 0.001% to 1% by mole, relative to the amount of the monomer components. When the use amount of the internal crosslinking agent is 0.0001% by mole or greater, the proportion of the extractable polymer content of the resulting water absorbent resin powder is appropriate, and therefore, a sufficient amount of water absorption under pressure can be secured. Furthermore, when the use amount of the internal crosslinking agent is 3% by mole or less, the crosslinking density is also appropriate, and a sufficient amount of water absorption of the resulting water absorbent resin powder is obtained. Meanwhile, the internal crosslinking agent may be added to the reaction system all at once, or may be added in divided portions.

(Site of Dispersion of Gas Bubbles)

The method for dispersing gas bubbles in an aqueous solution of acrylic acid-type monomers is such that gas bubbles may be introduced into an aqueous solution of acrylic acid-type monomers after preparation, or gas bubbles may be introduced individually into the raw materials of the aqueous solution of acrylic acid-type monomers, and then the aqueous solution of acrylic acid-type monomers may be prepared from the raw materials containing gas bubbles. In the case of introducing gas bubbles into the raw materials, examples of the site of dispersion of gas bubbles include unneutralized acrylic acid, a solvent (water or the like), an aqueous solution of an acrylic acid salt as a neutralization product of acrylic acid, an aqueous solution of acrylic acid-type monomers, a crosslinking agent, and the like. A preferred example is a mixture of these components, and gas bubbles are dispersed in water, an aqueous solution of an acrylic acid salt, or an aqueous solution of acrylic acid-type monomers that is prepared from those raw materials and will be polymerized.

(Gas)

Examples of the gas used for such dispersion of gas bubbles include air, an exhaust gas, oxygen, nitrogen, carbon dioxide, argon, helium, ozone, mixtures thereof, and the like. In view of polymerizability, one or more kinds of inert gases such as nitrogen, carbon dioxide and argon are preferably used, and among these, inexpensive nitrogen is particularly preferred. The proportion of the inert gas is 80% by volume or greater, more preferably 99% by volume or greater, still more preferably 99.9% by volume or greater, and particularly preferably 99.99% by volume or greater, and the pressure is appropriately determined to be normal pressure, an added pressure, or a reduced pressure.

The temperature of the inert gas is also appropriately determined and is not particularly limited. However, from the viewpoint of effects, the temperature is preferably the boiling point of the gas (for example, −210° C. for nitrogen) to 1000° C., and more preferably in the range of 0° C. to 100° C., or 10° C. to 50° C. The temperature of the aqueous monomer solution may be controlled, or the solubility or dispersibility of the gas may be adjusted, by cooling or heating the gas temperature. Meanwhile, in the case of dispersing carbon dioxide in the monomer, solid $CO_2$ (dry ice, melting point −79° C.), carbonic acid salts (for example, sodium carbonate, sodium hydrogen carbonate, magnesium carbonate, and the like; generates $CO_2$ gas by neutralization with acrylic acid), solid urea (generates $N_2$ gas) and the like may be used as the source of gas generation. However, from the viewpoints of effects and cost, a gaseous gas, particularly a gas in the temperature range described above, is preferably used.

In the following description, a method of mainly using a gaseous gas directly will be described.

(Method for Dispersing Gas Bubbles)

The method for dispersing gas bubbles (particularly, a gaseous gas) in the present invention is preferably carried out by at least one method selected from the following, and/or a combination of those methods, such that the volumetric expansion factor after the dispersion in the aqueous monomer solution prior to dispersion of gas bubbles exceeds 1.1 times. Furthermore, for stable dispersion of gas bubbles, a surfactant is preferably used.

According to the present invention, the method for dispersing gas bubbles may be in a batch mode or in a continuous mode, and may be carried out in a single stage or in two or more stages. However, from the viewpoint of the stability of gas bubbles, it is preferable to carry out the dispersion in a single stage in a continuous mode. That is, it is preferable to continuously supply a gas to a continuous fluid of the aqueous monomer solution or other raw materials, and particularly, it is preferable that a gas be continuously supplied into the pipe through which the aqueous monomer solution or other raw materials are transported. In this manner, gas bubbles are dispersed in the aqueous monomer solution. In the case of using an inert gas as the gas, it is also preferable to have the aqueous monomer solution degassed in advance (to a dissolved oxygen content of 1 [mg/l] or less), so as to accelerate polymerization.

(Liquid-Gas Mixing and Dispersion of Gas Bubbles in Mixing Zone Having Surface Asperity and/or Filler)

As the method for dispersing gas bubbles according to the present invention, preferably, a method of dispersing gas bubbles by introducing the aqueous monomer solution and a gas into a mixing zone having surface asperity and/or a filler, and thereby mixing the two components, is used. When mixing is carried out in a mixing zone having surface asperity, protrusions, a blade, baffle plates, a filler or the like, which disturbs the flow of a fluid, gas bubbles can be uniformly and stably dispersed in the aqueous monomer solution.

Figure 3:
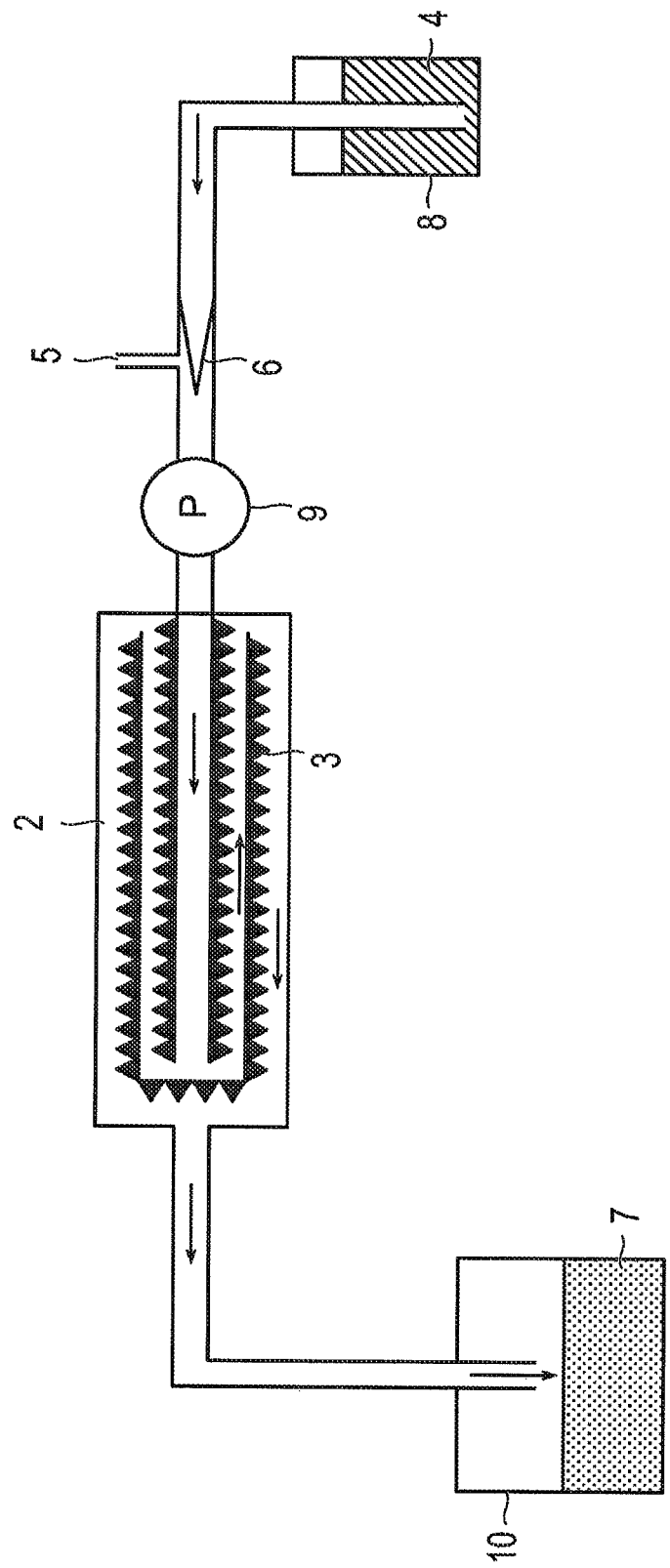
FIG. 3 is a schematic diagram illustrating a mixing zone having surface asperity or a filler.

As the mixing zone having surface asperity or a filler, for example, the mixing zone illustrated in FIG. 3 may be used. In FIG. 3, when an aqueous monomer solution containing gas bubbles that have been fluid mixed is passed through between gaps having protrusions, the gas bubbles are stably and uniformly dispersed. Thus, an aqueous monomer solution in which the volumetric expansion factor exceeds 1.1 times as compared with the state in which gas bubbles are not dispersed, can be obtained. To explain more specifically with reference to FIG. 3, an aqueous monomer solution 4 prepared in a monomer preparation tank 8 is passed through a mixing zone 2 having surface asperity 3 by using an aspirator 6 and a pump 9, and a gas bubble-containing aqueous monomer solution 7 is sent to a storage tank 10. Before the mixing zone 2, a gas 5 and the aqueous monomer solution 4 are mixed. Examples of apparatuses having such a mixing zone include "WHIP AUTO (trade name)" manufactured by Deutsch Hans Kratt GmbH, "ZANOMAT (trade name)" manufactured by Deutsch F. Pfeifinger AG, and the like.

According to the present invention, the aqueous monomer solution containing gas bubbles dispersed therein can also be stirred by providing a rotating blade in the mixing zone. Through stirring, fine gas bubbles can be dispersed in the aqueous monomer solution more uniformly and stably. Specifically, an S1 mixer etc. may be used.

(a) Dissolution of Gas by Pressurization of Aqueous Monomer Solution and Gas, and Subsequent Pressure Release As the method for dispersing gas bubbles according to the present invention, a dispersion method involving dissolution of a gas by pressurization of the aqueous monomer solution and the gas, and subsequent pressure release, is preferably used. When a gas is dissolved in the liquid by applying pressure at about 100 kPa to 1000 kPa, or at about 200 kPa to 400 kPa, and then a flash operation is performed in the liquid through a pressure reducing valve, that is, the pressure is released, the gas that is in an oversaturated state due to pressure reduction is released from the liquid mainly in the form of microbubbles. The solubility of the gas in the liquid is determined in accordance with the temperature and pressure, according to Henry's Rule (p=HC). Dispersed gas bubbles are obtained through a gas that has been first dissolved by such pressurization.

The degree of oversaturation is preferably 1.01 times to 10 times, more preferably 1.05 times to 5 times, and still more preferably 1.06 times to 3 times, relative to the saturation solubility at a predetermined temperature of the gas.

(b) Formation of Swirling Flow of Aqueous Monomer Solution and Gas

In addition to the methods described above, a preferred example of the method for dispersing gas bubbles according to the present invention may be formation of a swirling flow of the aqueous monomer solution and the gas. This method is a method of swirling a gas-liquid two-phase fluid and thereby dispersing gas bubbles at the outlet port (discharge port of a mixing machine), and the ratio of the gas flow rate and the liquid flow rate is preferably 1/7 to 1/15, while the swirling speed is preferably 10 to 10,000 rotations per second, and more preferably 100 to 1,000 rotations per second.

Examples of a swirling type fine gas bubble generator are described in, for example, WO 00/69550 A, JP 2003-205228 A, JP 2000-447 A, JP 2006-116365 A, and the like, but there are no particular limitations.

(c) Mixing of Gas into Aqueous Monomer Solution Through Fine Pores

This is a method of generating gas bubbles through the fine pores of various porous materials, membranes, filters and the like, and porous glass ($Na_2O$—$CaO$—$Al_2O_3$—$B_2O_3$—$SiO_2$-type glass) or the like is used. The method can be carried out by using, for example, a Kinoshita type glass ball filter manufactured by Kinoshita Rika Kogyo Co., Ltd.

(Dispersion of Gas Bubbles by Microbubble Generator)

The dispersion of gas bubbles according to the present invention may also be carried out by mixing the aqueous monomer solution and an inert gas with a microbubble generator. One or more techniques of the items (a) to (c) described above or items (1) to (8) described below can be applied to the generation of microbubbles, and preferably, item (a) or (b) is applied. If necessary, a shear force is further applied to the gas-liquid mixture formed from the aqueous monomer solution and gas bubbles. Meanwhile, there are no particular limitations on the microbubble generator that is employed in the present invention, and commercially available products can be used. Examples of commercially available products will be listed below.

OHR Line Mixer (OHR Laboratory Corp.)

M type microbubble generator (Nanoplanet Research Institute Corp.)

Microbubble generator for business use, SMB-450 type (Ishimaru Shoko Co., Ltd.)

Microbubble generator, Mbelife (Kansai Automation Equipment Co., Ltd.)

Sphere-mounted gas bubble generator, MBO type (Nishida Tekko Corp.)

PumpAerator (Teikoku Denki Manufacturing Co., Ltd.)

A microbubble generator has a water inlet port and a water outlet port, and when a liquid (water or monomers) is allowed to flow in through this water inlet port at or more than a certain pressure, in the inside of the microbubble generator, the gas incorporated in the water gathers at the center due to a density difference, and forms a gas axis. Thereby, a pressure gradient is produced between the outer periphery and the center inside the microbubble generator. At this time, an almost vacuum state is attained at the center of the gas axis. On the other hand, while the water that is pressurized and attempts to jet out, and the water that attempts to flow into the gas axis in a vacuum state (a supernegative pressure state) collide with each other and swirl around, the gas axis passes through between these waters, and at this time, the gas is sheared and finely broken to become microbubbles.

According to the present invention, the number average diameter of the gas bubbles including the microbubbles generated by the microbubble generator or other techniques is preferably 5 μm to 1000 μm, and more preferably 10 μm to 500 μm. If the average diameter of the gas bubbles is less than 5 μM, interconnection of gas bubbles after polymerization is decreased, and the water absorbent resin is likely to have a poor water absorption rate. If the average diameter is greater than 1 mm, the strength becomes fragile, and it is difficult to obtain a powder with a majority of particles having a size of 150 μm or greater by pulverizing the polymer gel after drying.

Furthermore, the throughput of the microbubble generator can be appropriately set based on the desired physical properties of the water absorbent resin powder or the like, but it is preferable to set the flow velocity of the aqueous monomer solution high. The flow velocity of the aqueous monomer solution is preferably 500 [kg/hr] or greater, more preferably 1000 [kg/hr] or greater, and still more preferably 2000 [kg/hr] or greater. Meanwhile, such an amount of production per hour is not limited to the use of a microbubble generator, and the production method of the present invention can be generally suitably applied to the industrial production of a large scale.

(Other Methods Used in Combination as Necessary)

In addition to the method for gas-liquid mixing and gas bubble dispersion in a mixing zone having surface asperity and/or a filler, the methods (a) to (c), and the method for dispersing gas bubbles by a microbubble generator described above as the methods for dispersing gas bubbles, the following methods (1) to (8) can be used or can be used in combination.

(1) Static Mixer System

A static mixer in which there is no movable part, and a fluid is mixed when it passes through elements that are fixed inside a pipe. A gas-liquid two-phase flow that flows in a swirling form is blasted by a spiral flow inducing unit inside a round pipe and mushroom-shaped protrusions equipped inside the pipe, and thereby, gas bubbles are generated. A specific example is an OHR mixer.

(2) Cavitation System

It is a method of modifying the shape of flow channels so as to intentionally induce cavitation inside a gas dispersing machine, and thereby generating gas bubbles.

(3) Combination of Centrifugal Pump and Swirling Flow Type Microbubble Generator It is a method of dissolving a gas under pressure into a liquid by the vortex stirring action by means of a pump and an increase in pressure with the pump, and micronizing the gas that is not dissolved, with a swirling flow type microbubble generator.

(4) Venturi System

A method of generating gas bubbles by blasting large gas bubbles by means of a shock wave that is produced by a rapid change in the liquid flow velocity when a gas and a liquid are simultaneously allowed to flow through a straw section (contraction), may be used.

(5) Rotation System

A method of generating gas bubbles by rotating a stirring blade at a high speed and self-supplying a gas, may be used.

(6) Ultrasonic System

A method of generating gas bubbles by appropriately setting the ultrasonic wave frequency, the pressure amplitude, and the like, may be used.

(7) Phase Change System

When a gas mixture of a gas (nitrogen gas) and water vapor is blown through a fine nozzle into a liquid, the water vapor coalesces, and gas bubbles of the gas (nitrogen gas) that does not coalesce remain behind.

(8) Electrolytic Degradation Method

A method of generating gas bubbles having a size in the order of micrometers by electrolysis of water, may be used.

Among these, preferably from the viewpoint of effects, a gas-liquid mixture composed of an aqueous monomer solution and gas bubbles is further subjected to a shear treatment at the step of obtaining an aqueous solution of acrylic acid-type monomers, and as the shearing method, the (3) combination of a centrifugal pump and a swirling flow type microbubble generator, or a static mixer combining shear and swirling flow, which is represented by an OHR mixer, is used.

(Volumetric Expansion Factor of Aqueous Monomer Solution)

According to the present invention, the extent of dispersion of gas bubbles in the aqueous solution of acrylic acid-type monomers is defined as the volumetric expansion factor after dispersion in the aqueous monomer solution prior to gas bubble dispersion. That is, the volumetric expansion factor is defined by the following formula (1).

[Formula 4]

Volumetric expansion factor [times]=(Volume of aqueous monomer solution after gas bubble dispersion)/(volume of aqueous monomer solution before gas bubble dispersion)     Formula (1)

The volumetric expansion factor is greater than 1.1 times, preferably greater than 1.1 times and less than or equal to 10 times, more preferably greater than 1.1 times and less than or equal to 8 times, and still more preferably 1.2 times to 5 times. The production method of the present invention is characterized in that gas bubble in the polymer gel are likely to be interconnected at a relatively low extent of gas bubble dispersion which gives a volumetric expansion factor of greater than 1.1 times, and preferably 1.2 times or greater. As the volumetric expansion factor is higher, continuous gas bubbles can be easily formed. However, as the factor is higher, the pore size of the gas bubble tends to increase, and the gas bubble stability in the aqueous monomer solution is also poor. Thus, an operation of uniform gas bubble dispersion is achieved with difficulty. In the case where a porous gel is dried and pulverized, and is used as a powder, even from the viewpoint of the handleability of particles in a powder form, or of avoiding an excessive decrease in bulk density or impact resistance, it is desirable to adjust the volumetric expansion factor to 10 times or less, 8 times or less, or 5 times or less.

Examples of the method for controlling the volumetric expansion factor to exceed 1.1 times include a method of appropriately setting the conditions for the gas bubble generator; a method of adding an additive for enhancing the gas bubble stability, such as a surfactant or a hydrophilic polymer, to the aqueous monomer solution; a method of adjusting the expansion factor by debubbling; and the like.

(2-2) Uniforming Step (D) of Bubbles in the Aqueous Monomer (Uniforming Step of Bubbles)

The present invention may further include a uniforming step of bubbles or a debubbling step as necessary. When a uniforming step of bubbles is included, starting from large gas bubbles, gas bubbles are sequentially eliminated from the monomers, and excessive foaming is suppressed. By achieving a uniform gas bubble size, the stability of gas bubbles is enhanced. The time of uniforming of bubbles to be used is 5 seconds or longer, 10 seconds to 60 minutes, preferably 30 seconds to 30 minutes, and particularly preferably 60 seconds to 20 minutes.

As a preferred method for uniforming of bubbles, a method of using the circulation tank illustrated in FIG. 1 or FIG. 2 described below may be used. Furthermore, another preferred method for uniforming of bubbles may be a method of introducing gas bubbles and then retaining the system at normal pressure for a predetermined time, or repeating the steps. The retention temperature is 0° C. to 100° C., and more preferably 20° C. to 50° C.

Regarding the uniforming step of bubbles used in the present invention, a known technology may be employed, and examples include the method described in U.S. Pat. No. 6,667,372, the method described in "Foam Engineering, 1$^{st}$ Edition" published by Technosystem Publishing Co., Ltd., pp. 759-774, and the like.

A preferred uniforming step of bubbles involves circulating a monomer containing a circulating gas stream (gas bubbles) in a circulation tank, and the uniforming step of bubbles preferably involves oxygen in an amount of 1% by volume or more in the headspace of the circulation tank. It is preferable to carry out the step (B) of polymerizing an aqueous monomer solution after the uniforming step of bubbles. At this time, it is preferable to perform polymerization after at least a portion of the aqueous monomer solution from the circulation line is neutralized as necessary. In addition, uniforming of bubbles may also be accumulating gas bubbles by maintaining the time to the initiation of polymerization for a certain time in the pipe or in the polymerization apparatus.

Figure 2:
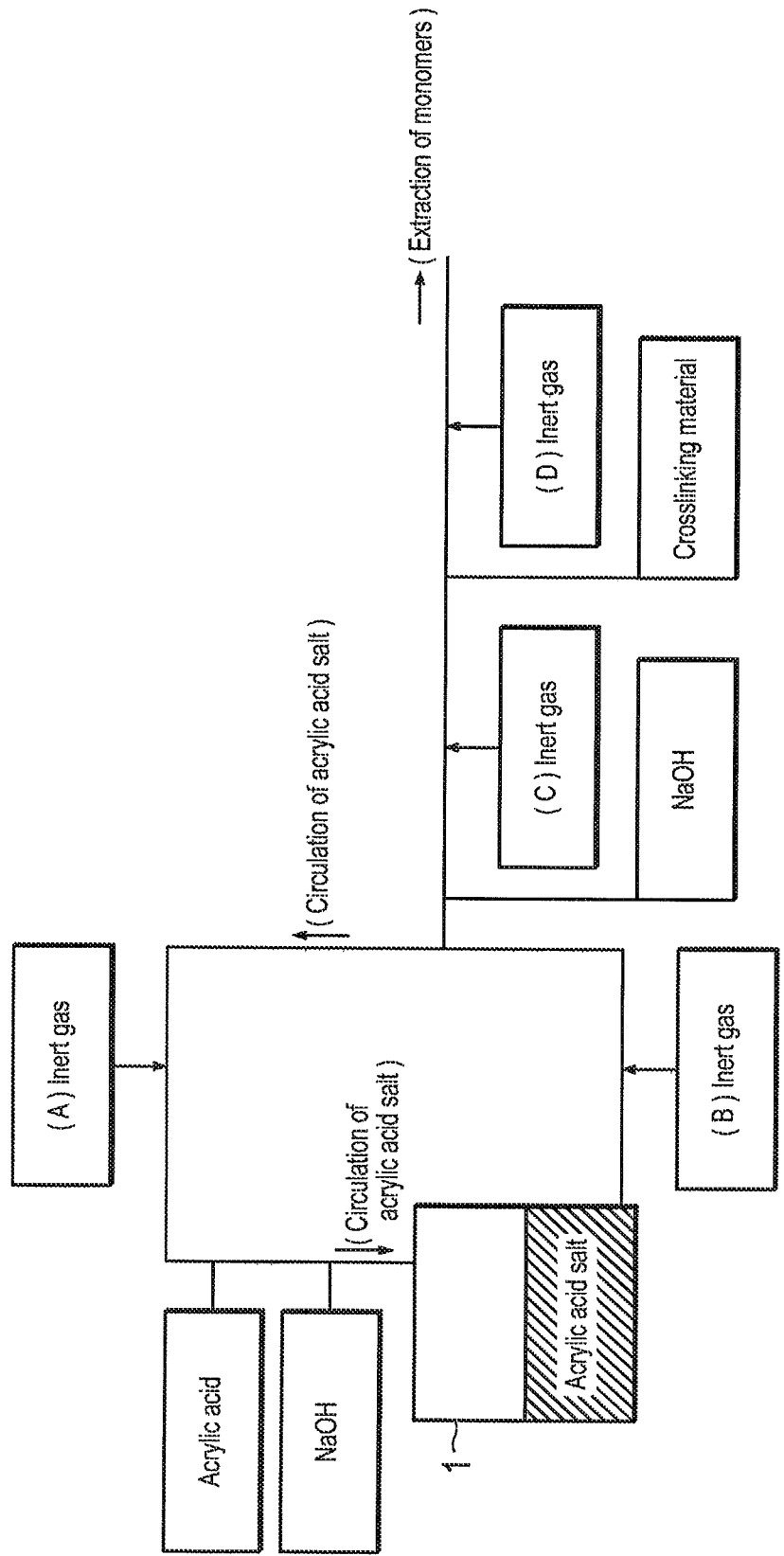
FIG. 2 is a flow diagram illustrating another example of the foam stabilizing step of circulating an aqueous monomer solution containing an inert gas in a circulating tank.

Specifically, such a debubbling step (uniforming of bubbles) is illustrated in FIG. 1 and FIG. 2. Meanwhile, in FIG. 1 and FIG. 2, the circulation pump, the thermal exchanger and the like are not shown.

As shown in FIG. 1, circulation is achieved as the monomers that have entered a tank 1 flow out through the lower part of the tank 1 to the circulation line, and an inert gas is introduced, flows through the circulation line, and flows again into the tank 1 through the upper part of the tank. Here, since the monomers are circulated while an inert gas is introduced, the gas is dissolved and/or dispersed in the monomers. The monomers in which the gas is dissolved and/or dispersed are retained inside the tank 1 for the period in which the monomers flow into the tank 1 and flow out again to the circulation line, and thus uniforming of bubbles proceeds.

Furthermore, also in the case of uniforming of bubbles while the monomers are neutralized, similarly, as shown in FIG. 2, circulation is achieved as the neutralized monomers that have entered the tank 1 flow out through the bottom of the tank 1 while an inert gas is introduced, and flow again into the tank 1 through the upper part, and thus uniforming of bubbles can be carried out.

Furthermore, the bubble-uniformed monomers may be directly pulled out and used in the subsequent step as shown in FIG. 1, or as shown in FIG. 2, the bubble-uniformed monomers may also be pulled out after a neutralizing agent or a crosslinking agent is added.

Meanwhile, examples of the circulation tank are described in WO 2007/28746 A, WO 2007/28747 A, and WO 2009/123197 A, but in the present invention, as illustrated in FIG. 1 and FIG. 2, gas bubbles can be homogenized and stabilized by dissolving or dispersing an inert gas in the aqueous monomer solution before circulation, and further circulating the aqueous monomer solution in a tank. Here, the interior of the circulation tank may be filled with an inert gas, but in view of the stability of the monomers, it is preferable that the tank be filled with oxygen, particularly air.

Furthermore, polymerization may be carried out by feeding an aqueous monomer solution containing gas bubbles into a polymerization apparatus having an open upper part, subsequently removing gas bubbles, with large gas bubbles being removed first, and then subjecting the aqueous monomer solution which stably contains fine gas bubbles, to the addition of a polymerization initiator or irradiation with energy rays such as ultraviolet, infrared, or microwave, after a predetermined time.

The size of the gas bubbles may be measured by (a) a laser diffraction scattering method (also known as: a static light scattering method), (b) a dynamic light scattering method, (c) an electrical sensing zone method (general name: Coulter counter method), (d) a particle counter method (a light scattering system, a light blocking system), (e) a visualization method by camera photographing, (f) an interference imaging method using laser light and a CCD camera, and the like. If the measurement in the aqueous monomer solution before polymerization is difficult, preferably, a foam-like polymer obtained after polymerization is conditioned with moisture so that the foam-like polymer can be easily stepped into semi-solid slices as necessary, subsequently the foam-like polymer cut to collect slices, and then the average pore size can be measured by visual inspection using a microscope, or by an image analysis software.

For the measurement of number, (c) an electrical sensing zone method or (d) a particle counter method is used if possible, and in order to measure gas bubbles having a size in the order of nanometers, (b) a dynamic light scattering method or (a) a laser diffraction scattering method (also known as: a static light scattering method) is appropriately used.

(Surfactant)

According to the present invention, mixing of the aqueous monomer solution and an inert gas is carried out preferably in the presence of a surfactant. By using a surfactant, the gas bubbles can be stably dispersed. Furthermore, a water absorbent resin having desired properties can be obtained by appropriately adjusting the type or amount of the surfactant, but in the present invention, the use of a surfactant is optional, and the present invention can be applied even in the absence of the surfactant. There are no particular limitations, but examples of such a surfactant include anionic surfactants, nonionic surfactants, cationic surfactants, amphoteric surfactants, fluorine-based surfactants, organometallic surfactants, and the like. These surfactants may be used individually or may be used in combination.

Specifically, polyglycerin fatty acid esters may be used, and the polyglycerin fatty acid esters are preferably fatty acid esters of polyglycerin of trimer or larger, and more preferably ranging from hexamer to decamer. The fatty acid is a linear or branched fatty acid having 6 to 28 carbon atoms, more preferably 12 to 24 carbon atoms, and particularly preferably 16 to 20 carbon atoms. Specific examples of the polyglycerin fatty acid esters include tetraglyceryl monostearate, tetraglyceryl monooleate, tetraglyceryl tristearate, tetraglyceryl pentastearate, tetraglyceryl pentaoleate, tetraglyceryl monolaurate, tetraglyceryl monomyristate, hexaglyceryl monostearate, hexaglyceryl monooleate, hexaglyceryl tristearate, hexaglyceryl pentastearate, hexaglyceryl pentaoleate, hexaglyceryl polyricinolate, decaglyceryl monolaurate, decaglyceryl monostearate, decaglyceryl monomyristate, decaglyceryl monoisostearate, decaglyceryl monooleate, decaglyceryl monolinoleate, decaglyceryl distearate, decaglyceryl diisostearate, decaglyceryl tristearate, decaglyceryl trioleate, decaglyceryl trioleate, decaglyceryl pentastearate, decaglyceryl pentaisostearate, decaglyceryl pentaoleate, decaglyceryl heptastearate, decaglyceryl heptaoleate, decaglyceryl decastearate, decaglyceryl decaisostearate, decaglyceryl decaoleate, and the like.

Specific examples of the nonionic surfactants include nonylphenol polyethylene oxide adducts; block polymers of ethylene oxide and propylene oxide; sorbitan fatty acid esters such as sorbitan monolaurate, sorbitan monomyristyrate, sorbitan monopalmitate, sorbitan monostearate, sorbitan tristearate, sorbitan monooleate, sorbitan trioleate, sorbitan sesquioleate, and sorbitan distearate; glycerin fatty acid esters such as glycerol monostearate, glycerol monooleate, diglycerol monooleate, and self-emulsifying glycerol monostearate; polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ethers; polyoxyethylene alkyl aryl ethers such as polyoxyethylene nonyl phenyl ether; polyoxyethylene sorbitan fatty acid esters such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate; polyoxyethylene sorbitol fatty acid esters such as polyoxyethylene sorbite tetraoleate; polyoxyethylene fatty acid esters such as polyethylene glycol monolaurate, polyethylene glycol monostearate, polyethylene glycol distearate, and polyethylene glycol monooleate; polyoxyethylene alkylamines; polyoxyethylene hardened castor oils; alkyl alkanolamides, and the like.

As the anionic surfactant, a compound having an anion moiety and an oil-soluble moiety can be preferably used, and examples thereof include reactive anionic emulsifiers having double bonds, such as alkyl sulfate salts such as sodium dodecyl sulfate, potassium dodecyl sulfate, ammonium alkyl sulfate; sodium dodecyl polyglycol ether sulfate; sodium sulforicinoate; alkyl sulfonates such as sulfonated paraffin salts; alkyl sulfonates such as sodium dodecyl benzenesulfonate, alkali metal sulfates of alkali phenol hydroxyethylene; higher alkyl naphthalenesulfonates; fatty acid salts such as naphthalenesulfonic acid-formalin condensate, sodium laurate, triethanolamine oleate; polyoxyalkyl ether sulfuric acid ester salts; polyoxyethylene carboxylic acid ester sulfuric acid ester salts, polyoxyethylene phenyl ether sulfuric acid ester salts; succinic acid dialkyl ester sulfonic acid salts; and polyoxyethylene alkyl aryl sulfate salts, and the like. In addition to these, the surfactants listed in JP 10-251310 A may be used.

The use amount of these surfactants is preferably an amount as small as possible relative to the amount of the monomer used. The use amount is preferably less than 10% by weight, more preferably less than 5% by weight, still more preferably less than 1% by weight, and particularly preferably less than 0.1% by weight. If the amount of the surfactant is large, when the resulting water absorbent resin is brought into contact with the aqueous liquid to be absorbed, the amount of the surfactant that is eluted also increases. Therefore, in the case of actual use in hygiene materials such as diapers, since the surfactant can decrease the interfacial tension of the body fluid, it is desirable to use an amount of surfactant that is as small as possible. Therefore, the elution of the surfactant at the time of water absorption can be suppressed by using a so-called reactive surfactant such as a surfactant having a reactive unsaturated group that is polymerizable with acrylic acid (salt) in the structure, or a silicone-based surfactant having an epoxy group or an amino group, which are both highly reactive with the carboxyl group of acrylic acid, or by using a surfactant having a high molecular weight. Particularly, for stable dispersion of gas bubbles, it is preferable to suppress a decrease in the interfacial tension described above, by using a hydrophilic polymer etc. that will be described below together and reducing the use amount of the surfactant.

According to the present invention, specifically, the surface tension of the water absorbent resin measured according to section (5-8) that will be described below, is controlled to be preferably 55 [mN/m] or higher, more preferably 60 [mN/m] or higher, particularly preferably 65 [mN/m] or higher, and still more preferably 70 [mN/m] or higher. For the upper limit, about 75 [mN/m] is usually sufficient. Since the decrease in the surface tension is suppressed, the liquid absorption characteristics of hygiene articles are improved, and the amount of re-wetting is decreased.

(2-3) Step (B) of Obtaining Foamed Polymer by Polymerizing Aqueous Monomer Solution (Polymerization Step)

This step is a step of polymerizing the aqueous monomer solution that has gone through the step (A), and step (D) as necessary, and thereby obtaining a foamed polymer. It is preferable that the aqueous monomer solution containing gas bubbles dispersed at a predetermined volumetric expansion factor, be supplied to the polymerization apparatus as rapidly as possible so that a certain amount of as bubbles are maintained. Preferably, it is preferable to supply the aqueous monomer solution to the polymerization apparatus within 5 minutes, more preferably within 3 minutes, and particularly preferably within 1 minute.

(Polymerization Initiator)

There are no particular limitations on the polymerization initiator that is used in the present invention, and one kind or two or more kinds can be selected for use from among those used in the production of conventional water absorbent resins, in accordance with the type of the monomer to be polymerized, the polymerization conditions, and the like. For example, thermally decomposable initiators (for example, persulfates such as sodium persulfate, potassium persulfate, and ammonium persulfate; peroxides such as hydrogen peroxide, t-butyl peroxide, and methyl ethyl ketone peroxide; azo compounds, such as azonitrile compounds such as 2-carbamoylazoisobutyronitrile, azoamidine compounds such as 2,2'-azobis(2-methylpropionamidine) dihydrochloride, cyclic azoamidine compounds such as 2,2'-azobis-2-(2-imidazolin-2-yl)propane hydrochloride, azoamide compounds, alkyl azo compounds, 2,2'-azobis(2-amidinopropane) dihydrochloride, 2,2'-azobis[2-(2-imidazolin-2-yl)propane]dihydrochloride), and the like, or photodecomposable initiators (for example, benzoin derivatives, benzyl derivatives, acetophenone derivatives such as 2-hydroxy-2-methyl-1-phenyl-propan-1-one, benzophenone derivatives, azo compounds, and the like), and the like may be used. Among these polymerization initiators, azo polymerization initiators (preferably, water-soluble azo polymerization initiators, for example, 2,2'-azobis(2-methylpropionamidine) dihydrochloride) that generate nitrogen gas at the time of polymerization may be used to incorporate more gas bubbles.

Furthermore, decomposition of these polymerization initiators can be accelerated by using a reducing agent in combination. Thus, a redox system initiator combining the two can also be used. There are no particular limitations on the reducing agent described above, but examples thereof include (bi)sulfites such as sodium sulfite, and sodium hydrogen sulfite; reducing metal (salts) such as L-ascorbic acid (salts), and ferrous salts; amines, and the like. In the case of using an oxidizing polymerization initiator and a reducing agent as in the case of redox system initiators, the respective agents may be incorporated into the aqueous monomer solution, or the reducing agent may be mixed into the aqueous monomer solution in advance.

The use amount of the polymerization initiator is preferably 0.0001% to 1% by mole, and more preferably 0.0005% to 0.5% by mole, relative to the total amount of the monomers. When the use amount is 0.0001% by mole or greater, it is preferable because the amount of residual monomer is decreased. Furthermore, when the use amount is 1% by mole or less, the polymerization initiator less affects the color tone of the water absorbent resin.

(Hydrophilic Polymer and the Like)

On the occasion of the polymerization as described above, a water-soluble polymer, a water absorbent resin, or water-insoluble fine particles, all of which are generally known as thickeners, is further used in the aqueous monomer solution prior to polymerization as necessary.

Specifically, the stability of the gas bubbles dispersed in the aqueous monomer solution can be improved by adding a water-soluble polymer such as high molecular weight polysaccharides, including starch, starch derivatives (for example, etherified starch, esterified starch and the like), cellulose, cellulose derivatives (for example, carboxymethyl cellulose, hydroxyethyl cellulose and the like), and guar gum; and hydrophilic polymers, including polyvinyl alcohol, polyacrylic acid (salts), and polyacrylic acid (salt) crosslinked products; or water-insoluble fine particles, including silicon dioxide (silica), zeolite, talc, titanium dioxide, and the like, and thereby foaming can be promoted. Furthermore, in order to reduce fine powder or to promote foaming, the aqueous monomer solution may be thickened by recycling the fine powder (preferably, a fine powder containing 70% by weight or more of a powder having a particle size of 150 µm or less) that will be described below of the water absorbent resin into the polymerization step. Preferably, a water-soluble polymer or a water absorbent resin, particularly a nonionic water-soluble polymer (particularly, starch, PVA, hydroxyethyl cellulose, or the like), or a polyacrylic acid (salt)-typed water absorbent resin, is used as the thickening agent.

Furthermore, for the purpose of improving the water absorption performance, a polymerization improving agent such as an inorganic reducing agent such as hypophosphorous acid (salt) or a chelating agent may also be used. Meanwhile, the inorganic reducing agent and the chelating agent will be described in detail below. Furthermore, in order to enhance the flexibility of the foam-like polymer thus obtainable, known plasticizers other than water, for example, polyols such as glycerin, polyethylene glycol, and polypropylene glycol, may also be used.

The use amount of the additives described above is 0 parts to 50 parts by weight, or 0.01 parts to 20 parts by weight, relative to 100 parts by weight of the monomer.

(Polymerization Method)

There are no particular limitations on the polymerization method that is employed in the present invention, and a method that is used as a conventional method for producing a water absorbent resin is employed. For example, an aqueous solution polymerization method may be used. Examples of the aqueous solution polymerization method include a static polymerization method of polymerizing an aqueous monomer solution in a static state (a state without mechanical stirring), a stirred polymerization method of performing polymerization in a stirring apparatus, and the like; however, when it is intended to obtain a foam-like polymer in a stable manner, a static polymerization method is employed. These polymerization methods respectively include batch methods and continuous methods, but continuous methods are preferred. Also, in these polymerization methods, usually a belt polymerization apparatus, a tank type (silo type) polymerization apparatus, or a stirred polymerization apparatus is employed.

The apparatus for producing a water absorbent resin according to the present invention is not particularly limited as long as it is an apparatus capable of continuously polymerizing an aqueous monomer solution that is continuously supplied according to the method described above, but a continuous belt polymerization apparatus or a continuous stirred polymerization apparatus is preferred. For an aqueous monomer solution containing gas bubbles dispersed therein at a predetermined volumetric expansion factor, it is preferable to initiate polymerization as rapidly as possible after the supply to the polymerization apparatus so that a certain amount of gas bubbles may be maintained, and preferably, polymerization is initiated by irradiation of energy rays or heating within 5 minutes, more preferably within 3 minutes, and particularly preferably within 1 minute.

Meanwhile, in relation to the continuous belt polymerization apparatus, the technologies disclosed in JP 2000-034305 A, JP 11-228604 A, JP 62-156102 A, and the like can be applied. For example, the high temperature high concentration polymerization technology disclosed in JP 2002-212204 A can be applied. In this case, a preferred form of the polymerization apparatus is a continuous polymerization apparatus of endless belt type, and the belt is desirably a belt made of a fluorine resin, or a belt coated with a fluorine resin on the surface. Furthermore, an apparatus having a system equipped with a heating apparatus or a temperature retaining apparatus, so that the vapor of water and/or the monomer liquid generated at the time of polymerization is collected and recycled, is preferred. Furthermore, for the purpose of preventing a backflow of the monomer mixture liquid, it is preferable that the belt be horizontal or have the monomer mixture liquid supply unit at a lower position, and it is preferable that a belt washing step be provided between the point of discharge of the polymer gel from the belt and the monomer mixture liquid supply port.

The thickness of the belt polymerization is appropriately determined depending on the purpose or heat removal at the time of polymerization, and for example, the polymer is polymerized to a gel thickness of 0.1 cm to 30 cm, 0.5 cm to 20 cm, or 1 cm to 10 cm. Furthermore, the size of the belt is determined in accordance with the amount of production, and from an industrial viewpoint, for example, the belt width is selected to be about 0.1 m to 10 m, or 1 m to 5 m, while the length is selected to be about 5 m to 200 m. Also, in the case where polymerization is carried out in a tank system, the size of the tank is determined in accordance with the amount of production, and from an industrial viewpoint, a tank having a volume of 0.1 $m^3$ to 300 $m^3$, 1 $m^3$ to 100 $m^3$, or the like is used. Such a polymer gel obtained by static polymerization may be subjected, as necessary, to cutting, surface polishing, compression or the like that will be described below to be made into a molded product, or may be made into a powder (non-molded product).

Furthermore, in regard to the continuous stirred polymerization apparatus, a single-axis stirring apparatus can be employed, or a stirring apparatus having plural stirring axes, such as a continuous kneader, can also be employed. However, from the viewpoint of productivity, a plural-axes stirring apparatus is preferably used.

(Maximum Arrival Temperature at Time of Polymerization, and Measurement Method)

On the occasion of the polymerization described above, boiling polymerization (at a temperature higher than or equal to the boiling point of the solvent water) is used in order to increase gas bubbles in the water absorbent resin, and at least one time period of the polymerization step is set to be at a temperature 100° C. or higher. That is, so-called boiling polymerization is carried out, in which the upper limit of the temperature during polymerization is set to 100° C. or higher, preferably in the range of 100° C. to 140° C., more preferably 102° C. to 130° C., still more preferably 104° C. to 120° C., and particularly preferably 105° C. to 118° C., and moisture is evaporated during polymerization. Meanwhile, boiling polymerization also includes the cases where the boiling point of water (100° C.) is changed due to polymerization under reduced pressure, polymerization under pressure, or an increase in the molar boiling point occurring in monomers dissolved in water, and in the present invention, instances involving a polymerization step at or above 100° C. are referred to as boiling polymerization. The maximum arrival temperature at the time of polymerization may be achieved to be in the range described above by performing heating or cooling during polymerization, or may be achieved to be in the range described above only by the polymerization heat.

The temperature of polymerization can be measured with a contact thermometer or a non-contact thermometer (for example, an infrared thermometer), and in belt polymerization, the polymerization temperature can be measured from the temperature at the surface of the polymer gel, or the like. In the method of the present invention, since a polymer gel containing continuous gas bubbles is obtained, and at the time of polymerization, the solvent water boils causing evaporation of water, the polymer gel boils at a substantially uniform temperature at the surface and in the interior. Therefore, the maximum temperature of the polymer gel may be measured in the interior, or may be measured at the surface. However, preferably, the temperature is determined in the interior (core area). For the measurement of the maximum temperature at the core area of the polymer gel, measurement may be made with a contact thermometer such as a thermocouple.

In an example of a preferred method for measuring the maximum arrival temperature at the time of polymerization, for the temperature measurement of system having a rapid temperature change, a PC card type data collection system NR-1000 manufactured by Keyence Corp. is used, a thermocouple is placed at the core area of the polymerization system, and measurement can be made at a sampling period of 0.1 seconds. From a temperature-time chart thus obtained, the polymerization initiation temperature and the peak temperature (maximum arrival temperature) can be read.

(Other Polymerization Conditions and the Like)

Regarding the pressure at the time of polymerization, polymerization under reduced pressure (particularly, pressure reduced by more than 10% of the atmospheric pressure) or polymerization under pressure (pressure added by more than 10% of the atmospheric pressure) may be carried out, but from the viewpoints of the convenience of the apparatus, cost, foaming efficiency, and the like, polymerization is carried out at a pressure equivalent to substantially normal pressure (±10% or less, ±7% or less, ±5% or less, ±3% or less, or ±1% or less, or particularly ±0.1% or less of the atmospheric pressure). Here, even though the pressure is not intentionally reduced or added, the pressure at the time of polymerization may slightly vary due to an increase or a decrease in the temperature at the time of polymerization, or by introduction of an inert gas or air into the polymerization vessel or by ventilation. Polymerization is carried out at substantially normal pressure within the range described above.

The time period in which the temperature is 100° C. or higher at the time of polymerization in the present invention is appropriately determined in accordance with the polymerization method, and the time period is preferably 1 second or longer, 5 seconds or longer, or 30 seconds or longer. The time period is preferably adjusted so as to exhibit an increment of the solid concentration of the gel described below. Boiling polymerization for a long time does not contribute much to foaming, and may deteriorate the physical properties (the water absorption capacity or the extractable water content). Accordingly, the upper limit of the time period in which the temperature is 100° C. or higher during polymerization is set to be one hour or less, 30 minutes or less, 10 minutes or less, 5 minutes or less, or particularly 1 minute or less.

Meanwhile, if the maximum arrival temperature (peak temperature) of polymerization exceeds 140° C., there is a risk that the physical properties of the water absorbent resin powder may deteriorate. The maximum arrival temperature is set to preferably 130° C. or lower, and more preferably 120° C. or lower. The amount of moisture evaporation during polymerization may vary with the difference in the initiation temperature or the like, but it is preferable that the increment of the solid concentration of the polymer gel relative to the solid concentration in the aqueous monomer solution be 2% by weight or more (the upper limit is preferably 20% by weight, and the concentration of the gel-like product, particularly the solid concentration, obtained after polymerization is preferably in the range of 80% by weight or less), and it is more preferable to set the increment to be 3% to 20% by weight, and particularly preferably 5% to 20% by weight. However, the solid concentration in the aqueous monomer solution is defined by the following formula. Meanwhile, although the weight of non-volatile additives (for example, a hydrophilic polymer, a surfactant, and the like) is not taken into consideration in connection with the monomer concentration (formula 2) described above, the following solid concentration is defined to include the weight of non-volatile additives. Also, it is speculated that the generation of water vapor described above contributes to the production of continuous gas bubbles.

Solid concentration in a monomer [wt %]={(Weight of a monomer)+(weight of a non-volatile additive)}/{(weight of a monomer)+(weight of a non-volatile additive)+(weight of solvent)}×100   [Formula 5]

Since polymerization is usually carried out in a polymerization equipment in the presence of a gas stream of an inert gas or the like, even if the temperature during polymerization is lower than 100° C., in the case where the polymerization time is long, evaporation of moisture occurs. However, this is not intended to have no effect on the interconnection of gas bubbles as disclosed in the present invention.

According to the present invention, since gas bubbles are dispersed in the aqueous monomer solution to cause a volumetric expansion of greater than 1.1 times so as to increase the surface area, heat removal is relatively well achieved, and the temperature does not easily rise. However, by adjusting the upper limit temperature during polymerization to the range described above, and causing moisture evaporation to occur actively during polymerization, the ratio of interconnected voids (continuous gas bubbles) in the foamed polymer (foam-like polymer) can be increased, and thus a foam-like water absorbent resin having a high water absorption rate, or a water absorbent resin powder having a high water absorption rate using the resin can be produced. Furthermore, in order to achieve the matter described above, the temperature of polymerization initiation is preferably initiation at a high temperature which is set higher than room temperature, and specifically, the polymerization initiation temperature in the polymerization step is preferably 40° C. or higher, or 50° C. or higher, while the upper limit is 100° C. or lower, or 90° C. or lower, and particularly preferably 85° C. or lower. If the initiation temperature is lower than 40° C., it is difficult for the temperature to reach 100° C., and if the initiation temperature is too high, stable dispersion of gas bubbles is difficult, which is not preferable.

The polymerization time may be appropriately determined in accordance with the types of the monomer and the polymerization initiator, polymerization temperature, and the like. However, it is preferable to shorten the time period from the polymerization initiation to the point when the polymerization temperature reaches the maximum temperature, and specifically, the time period is preferably set to 20 minutes or less, more preferably 10 minutes or less, still more preferably 5 minutes or less, particularly preferably 2 minutes or less, and most preferably 1 minute or less. If the time is extended to, for example, one hour or longer, the dispersed gas bubbles may be defoamed during polymerization, it is difficult for the generated water vapor to tear the barrier walls of the gel, and the dispersed gas bubbles do not easily form continuous gas bubbles, which is not preferable. In regard to the conditions of the present invention, it is conceived that the balance between the gas bubble stability during polymerization, the strength of the polymer gel that forms gas bubble walls during polymerization, and the evaporation of moisture is advantageous for the formation of continuous gas bubbles.

In this case, a higher concentration of the aqueous solution of acrylic acid-type monomers in the polymerization step is preferred, and the concentration is 40% by weight or greater, 45% by weight or greater, or 50% by weight or greater (the upper limit is usually 80% by weight or less, or 70% by weight or less). When such a concentration is 40% by weight or greater, the dispersed gas bubbles can exist stably even at or above 40° C. However, when the concentration is less than 40% by weight, for example, under the conditions disclosed in the Examples of Patent Literature 23, stable dispersion of gas bubbles is enabled at room temperature, but if the temperature rises, the gas bubbles become unstable and are defoamed in a short time. In order to avoid this, it is believed that there is a need to lower the initiation temperature, and to set the polymerization time taken for the polymerization temperature to increase, relatively longer so as to increase the polymerization ratio, and to thereby increase the gel strength of the gas bubble walls. In this case, the dispersed gas bubbles will exist in an independent state in the gel.

In the continuous belt polymerization described above, a foam-like polymer gel which is continuous in a band shape is obtained. Furthermore, in the tank type (silo type) static polymerization, a foam-like polymer gel having a tank (silo) shape is obtained. The foam-like polymer gel can be directly used, or can be used after being finely cracked (fine crush step described below). The foam-like polymer gel has an advantage that the apparatus load at the time of pulverization tends to be smaller as compared with plate-shaped gels that have high solids content and do not contain gas bubbles. This allows application to the cutting type pulverizer disclosed in JP 2002-212204 A, which is advantageous for the pulverization of gels with high solids content, as well as to the extrusion type pulverizer, as represented by a chopper, that is inapplicable to plate-shaped gels. In this case, when the foam-like gel is crushed while kneading, an increase in the bulk density obtainable when the foam-like gel is produced into a water absorbent resin powder, and an increase in the impact resistance can be promoted without disadvantageously delaying the water absorption rate, as compared with the case of crushing the foam-like gel without kneading. The foam-like polymer gel may be further dried and pulverized to obtain a water absorbent resin powder, or the foam-like polymer gel may also be, for example, cut into a sheet form having a predetermined shape and dried to obtain a water absorbent resin molded product. The molded water absorbent resin or the water absorbent resin powder may be further surface crosslinking treated, granulated, have the moisture content adjusted, or have various modifying agents added thereto, and then may be used as water absorbent resin products. The pulverization or drying of the polymer gel and the surface crosslinking treatment may be achieved by employing known technologies.

(Production Technology and Maximum Arrival Temperature at Time of Polymerization for Conventional Foam-Like Water Absorbent Resins)

It is a well known technology to control the maximum temperature to be low at the time of polymerization of a water absorbent resin, and Patent Literature 20 discloses the gist that "the polymerization temperature is preferably adjusted so as to avoid boiling of the polymerizable aqueous mixture," in relation to the production of foam-like water absorbent resins. Furthermore, Patent Literatures 8, 21 and 30 to 32 also disclose, similarly to the case of Patent Literature 20, the gist of "avoiding boiling at the time of polymerization" in relation to the production of foam-like water absorbent resins. Moreover, Patent Literature 33 discloses the gist that "open gas bubble foam increases when the foam is produced at or below 65° C."

Furthermore, in connection with polymerization other than foaming polymerization, there has been disclosed a technology of controlling the maximum temperature to be low for the purpose of reducing the extractables or the like. Specifically, a technology of controlling the maximum temperature to 95° C. or lower (Patent Literature 34), a technology of performing polymerization at a polymerization temperature of 20° C. to 70° C. (Patent Literature 35), and a technology of performing polymerization at a polymerization temperature of 20° C. to 95° C. (Patent Literature 36) have been proposed.

As described above, in Patent Literatures 8, 20, 21, 29 to 33 and the like, boiling polymerization has been avoided in the production of (continuous) foam-like water absorbent resins; however, in the present invention, it was found that the boiling polymerization that has been conventionally avoided in the production of foam-like water absorbent resins, efficiently provides a water absorbent resin having continuous gas bubbles at a concentration of 40% by weight or greater and at a volumetric expansion factor of 1.1 times or greater.

(Mechanism for Production of Continuous Gas Bubbles)

The mechanism for the production of continuous gas bubbles of the present invention, which is not elucidated in Patent Literatures 8, 20, 21, 29 to 33 and the like, is speculated to be as follows, but the right or wrong of the mechanism speculated as such is not intended to limit the scope of the present invention.

That is, it is speculated that when gas bubbles are dispersed in an aqueous monomer solution at a monomer concentration of 40% by weight or greater until the volumetric expansion factor reaches 1.1 times or greater, and then boiling polymerization is carried out, independent gas bubbles (for example, spherical gas bubbles of nitrogen gas or the like) that are dispersed in the aqueous monomer solution undergo volumetric expansion, and also, at the time of gelation by boiling polymerization of the aqueous monomer solution, the volumetric expansion of the water vapor generated by boiling of water and of the independent gas bubbles dispersed in the aqueous monomer solution causes tearing of the barrier walls of the gas bubbles (spherical independent gas bubbles) of the gel generated in the early stage of polymerization by the polymerization of the aqueous monomer solution, thereby continuous gas bubbles being produced. Here, it is speculated that boiling polymerization is necessary for the destruction of barrier walls of the gel caused by generation of water vapor, and the aqueous monomer solution at a monomer concentration of 40% by weight or greater facilitates tearing of the barrier walls of the gas bubbles (spherical independent gas bubbles) of the gel generated in the early stage of polymerization, and production of continuous gas bubbles, due to the hardness of the gel originating from the high solids content, and to the polymerization rate.

Specifically, for example, when an aqueous monomer solution at a monomer concentration of 45% by weight (100 g, solids content therein: 45 g) produces a polymer gel at a solids content of 50% by weight (solids content therein: 45 g) through boiling polymerization, since evaporation of 10 g of water, that is, even for water vapor at 100° C., evaporation of about 17 L of water vapor, is caused by boiling polymerization, it is speculated that for the 45 g of the solids content, such a large amount of water vapor brings about expansion of gas bubbles (spherical independent gas bubbles) in the gel, tearing of the barrier walls of the independent gas bubbles, and production of continuous gas bubbles.

This is also supported by the fact that in Comparative Examples 13 to 15 described below, if even any one of the boiling polymerization, the monomer concentration of 40% by weight greater, and the volumetric expansion factor of 1.1 or higher lacks, sufficient continuous gas bubbles are not provided. However, such a speculated mechanism is not intended to limit the scope of the invention.

(Fine Crush Step)

At the time of polymerization, a fine crush step in which crush and fine crush are simultaneously carried out, or the foamed polymer obtained after polymerization is crushed and finely granulated, may be carried out if necessary. When gel-crush is achieved, particularly when gel-crush by kneading (fine crush) is achieved, a balance between the water absorption rate and liquid permeability is promoted, and impact resistance is also enhanced. Specifically, when the polymerization step is conducted by continuous kneader polymerization, the gel is gel-crushed during polymerization, and when the polymerization step is conducted by continuous belt polymerization, the gel is gel-crushed after polymerization. In the case of performing kneader polymerization, since gel-crush of the gel can be carried out by means of a kneader during polymerization, the fine crush step is included in the kneader polymerization step.

There are no particular limitations on the gel-crusher that can be used, and examples include a gel-crusher equipped with plural rotating stirring blades, such as a batch type or continuous type double-blade kneader, a single-screw extruder, a twin-screw extruder, a meat chopper, and the like. Among them, a screw type extruder having a perforated plate at the front end is preferred, and for example, the screw type extruder disclosed in JP 2000-63527 A may be used.

The temperature of the hydro gel at the time of gel-crush (cracking) is preferably 40° C. to 120° C., and more preferably 50° C. to 110° C., in view of the physical properties. When the gel temperature is 40° C. to 120° C., the hardness of the hydro gel is appropriate, and control of the particle shape or the particle size distribution can be easily achieved at the time of gel-crush. Meanwhile, the gel temperature can be controlled by the temperature at the time of polymerization, or by heating, cooling, or the like after polymerization.

The weight average particle diameter (D50) of the particulate hydro gel obtainable after gel-crush (cracking) is preferably 0.5 mm to 4 mm, more preferably 0.5 mm to 3 mm, and still more preferably 0.6 mm to 2 mm. When the weight average particle diameter (D50) of the particulate hydro gel is 0.5 mm or greater, an increase in the residual monomer (monomer) or an effect of enhancing the water absorption rate (FSR) can be expected. When the weight average particle diameter (D50) is 4 mm or less, the drying time is short, and an increase in the water-solubilized faction (Ext) can be suppressed. The proportion of a particulate hydro bubble gel having a particle size of 5 mm or greater is preferably 0% to 10% by weight, and more preferably 0% to 5% by weight, relative to the total amount of the particulate hydro gel. The particle size of the particulate hydro gel can be determined by classifying the particles with sieves of specific mesh sizes, similarly to the particle size of the water absorbent resin powder obtained after the pulverization step. Furthermore, even the weight average particle diameter (D50) can also be determined similarly. However, if the classification step for the particulate hydro gel makes the measurement difficult in a dry classification method due to aggregation or the like, the measurement is made by using the wet classification method described in paragraph [0091] of JP 2000-63527 A.

Suitably, the gel crush step described in Japanese Patent Application No. 2010-088993 (PCT/JP2011/058829), particularly the gel crush step employing a gel crush energy (GGE) of 18 to 60 [J/g], is applied to the present invention. The gel crush energy is such that the upper limit is preferably 60 [J/g] or less, more preferably 50 [J/g] or less, and still more preferably 40 [J/g] or less. The lower limit is preferably 18 [J/g] or greater, more preferably 20 [J/g] or greater, and still more preferably 25 [J/g] or greater.

(2-4) Step (C) of Heating and Drying Foamed Polymer (Heating and Drying Step)

The foam-like polymer gel obtained as described above is dried into a dried polymer. The resin solids content that is determined from its dry weight loss (1 g of a powder or particles is heated for 3 hours at 180° C.) is preferably adjusted to the range of 80% by weight or greater, more preferably 85% to 99% by weight, and still more preferably 90% to 98% by weight, and thus a dried polymer is obtained. In the case of using the water absorbent resin as a molded water absorbent resin other than a powder, water or a plasticizer may be added as necessary to adjust the flexibility.

The drying temperature is not particularly limited, but may be preferably in the range of 100° C. to 300° C., and more preferably in the range of 150° C. to 250° C. The foam-like polymer gel of the present invention can be easily dried directly as well as in a pulverized form, and the drying method specified in JP 2000-212215 A is preferably applied. If there are many independent gas bubbles in the polymer gel, when a crude crushed gel is dried at a high temperature, the gel is prone to expand and deform. However, since the gel of the present invention has many continuous gas bubbles, gel expansion is almost not observed at the time of high temperature drying, and the occurrence of less deformation is also an advantageous feature. Furthermore, since the gel of the present invention has many continuous gas bubbles, it is another advantageous feature that the drying time taken until a dried polymer is obtained is shortened.

That is, drying of the hydro gel obtained after polymerization requires large facilities or large thermal energy, and a long drying time, and there are problems of deterioration or coloration of the water absorbent resin caused by this drying for a long time, and an increase in the production cost for the water absorbent resin. However, in the present invention, such problems are solved, and shortening of the drying time, prevention of coloration, an enhancement of the water absorption performance, and the like are achieved.

(2-5) Pulverization Step/Classification Step, Particle Size Distribution (Particle Size)

The water absorbent resin that has gone through the heating and drying step described above may be used in a sheet form or in a block form, but when the water absorbent resin is preferably used as a powder having a predetermined particle size by pulverizing and/or classifying the water absorbent resin.

(Powder)

The weight average particle diameter (D50) in the case of stepping the water absorbent resin into a water absorbent resin powder is adjusted to 200 µM to 600 µm, preferably greater than or equal to 300 µm and less than 600 µm, more preferably 200 µm to 550 µM, still more preferably 250 µm to 500 µm, and particularly preferably 350 µm to 450 µm, from the viewpoint of physical properties enhancement. Furthermore, it is more desirable if there are fewer particles having a particle size of less than 150 µm, and the content of such particles is usually adjusted to 0% to 5% by weight, preferably 0% to 3% by weight, and particularly preferably 0% to 1% by weight. Furthermore, it is more desirable if there are fewer particles having a particle size of 850 µm or greater (or 710 µm or greater), and the content of such particles is usually adjusted to 0% to 5% by weight, preferably 0% to 3% by weight, and particularly preferably 0% to 1% by weight. Furthermore, in the present invention, surface crosslinking is achieved such that the proportion of particles having a size of 850 µm to 150 µm, and more preferably the proportion of particles having a size of 710 µm to 150 µm, is 95% by weight or greater, and more preferably 98% by weight or greater (the upper limit is 100% by weight).

In these measurement methods, standard sieves are used, and the methods are described in, for example, WO 2004/69915 A or EDANA-ERT420.2-02. The particle size prior to the surface crosslinking is also preferably applied to the particle size after surface crosslinking and to the final product (also known as: a particulate water absorbing agent).

(2-6) Molded Product and Shaping Step

The foam-like polymer gel obtained as described above or a dried polymer thereof may be in the form of powder, but the foam-like polymer gel obtained after static polymerization such as belt polymerization, tank polymerization and the like or a dried polymer thereof may be used directly or may be shaped. That is, in the present invention, a shaping step is included simultaneously with the polymerization step, or after the polymerization step. The dried polymer that has gone through heating and drying after the polymerization step may be produced into a molded product, or heating and drying may be carried out through a shaping step simultaneously with the polymerization step or after the polymerization step. The foam-like polymer gel obtained by belt polymerization is in the form of band, and in tank polymerization, a foam-like polymer gel having a tank shape (for example, a cylindrical gel) is obtained. Therefore, those polymer gels may be directly used as molded products, or if necessary, the polymer gels may be subjected to cutting, surface polishing, compression, or the like. Also, an aqueous monomer solution may be introduced into a three-dimensional mold in accordance with a predetermined shape such as a napkin and the like, and thereby a water absorbent resin molded product in the form of a final manufactured product may be obtained simultaneously with polymerization.

In the belt polymerization step described above, for example, a sheet-like polymer gel having a thickness of 0.1 cm to 30 cm, 0.5 cm to 20 cm, or 1 cm to 10 cm may be continuously obtained, and the width is also about 0.1 m to 10 m, or 1 m to 5 m, depending on the belt width. However, it is desirable to step the sheet-like polymer thus obtained appropriately by cutting, surface polishing, mortising, compression or the like in the thickness direction, width direction and length direction, and to thereby obtain a molded product. Furthermore, in the case of performing tank type polymerization, a polymer gel (for example, a cylindrical gel, a three-dimensionally molded gel or the like) having a volume of 0.1 $m^3$ to 300 $m^3$, or 1 $m^3$ to 100 $m^3$, may be obtained, but such a polymer gel may be subjected to cutting, surface polishing, compression or the like as necessary to be obtained as a molded product.

The shape of the molded product may be appropriately determined in accordance with the purpose, but in the case of intending to obtain a napkin or a diaper, it is preferable to produce a sheet-like product having a thickness of 0.1 cm to 2 cm, or 0.2 cm to 1 cm, and an area of 5 $cm^2$ or greater. The sheet-like product may be finally shaped into the absorbent layer of a napkin or a diaper, or may be made into a roll shape or a carpet shape so that the sheet-like product can be further shaped (cut or tailored). Furthermore, the sheet-like product may also be provided with figures, holes or embossing on the surface.

(2-7) Surface Crosslinking Step (Crosslinking Agent)

The present invention may further include a surface crosslinking step after drying. In the surface crosslinking, a covalently bondable surface crosslinking agent and/or an ionically crosslinkable surface crosslinking agent is used, and preferably, those crosslinking agents are used in combination.

Meanwhile, surface crosslinking is an operation of rendering the surface highly crosslinked as compared with the interior, and radical crosslinking may be achieved by using a radical polymerization initiator (for example, a persulfuric acid salt or a photoinitiator), or surface polymerization may be carried out by adding monomers to the particle surface. However, preferably, a crosslinking agent which is capable of reacting with the carboxyl group of a polyacrylic acid (salt)-type water absorbent resin is used. As will be described below, the surface crosslinking according to the present invention is not intended to be limited as described below.

(Covalently Bondable Surface Crosslinking Agent)

Examples of the surface crosslinking agent that can be used in the present invention include various organic or inorganic crosslinking agents, but organic surface crosslinking agents can be preferably used. Preferred examples in view of physical properties include, as surface crosslinking agents, polyhydric alcohol compounds, epoxy compounds, oxetane compounds, polyvalent amine compounds or condensates thereof with haloepoxy compounds, oxazoline compounds, (mono-, di- or poly-)oxazolidinone compounds, and alkylene carbonate compounds. Particularly, dehydration reactive crosslinking agents formed from polyhydric alcohol compounds, alkylene carbonate compounds and oxazolidinone compounds, which require reaction at a high temperature, can be used. If a dehydration reactive crosslinking agent is not used, more specifically, the compounds described as examples in U.S. Pat. Nos. 6,228,930, 6,071,976, 6,254,990, and the like may be used. Examples thereof include polyhydric alcohol compounds such as monomeric, dimeric, trimeric, tetrameric, or higher-mer propylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether, and glycidol; alkylene carbonate compounds such as ethylene carbonate; oxetane compounds; cyclic urea compounds such as 2-imidazolidinone; and the like.

(Ionically Bondable Surface Crosslinking Agent)

Furthermore, in addition to the organic surface crosslinking agents described above, a polyamine polymer or a polyvalent metal salt maybe used as an ionically bondable surface crosslinking agent to enhance liquid permeability or the like. Examples of the polyvalent metal salt (inorganic surface crosslinking agent) to be used include divalent or higher-valent, and preferably trivalent or tetravalent, polyvalent metal salts (organic salts or inorganic salts), and hydroxides. Examples of the polyvalent metal that can be used include aluminum, zirconium and the like, and thus aluminum lactate or aluminum sulfate may be used.

(Solvent)

The use amount of the surface crosslinking agent is appropriately determined in the range of 0.001 parts to 10 parts by weight, or 0.01 parts to 5 parts by weight, relative to 100 parts by weight of the water absorbent resin powder. In addition to the surface crosslinking agent, preferably, water can be used. The amount of water to be used is in the range of 0.5 parts to 20 parts by weight, and preferably 0.5 parts to 10 parts by weight, relative to 100 parts by weight of the water absorbent resin powder. Even in the case of using an inorganic surface crosslinking agent and an organic surface crosslinking agent in combination, the surface crosslinking agents are used together respectively in an amount of 0.001 parts to 10 parts by weight, or 0.01 parts to 5 parts by weight, relative to 100 parts by weight of the water absorbent resin powder. Furthermore, at this time, a hydrophilic organic solvent may be used, and the amount is in the range of 0 parts to 10 parts by weight, and preferably 0 parts to 5 parts by weight, relative to 100 parts by weight of the water absorbent resin powder. Furthermore, on the occasion of mixing of a crosslinking agent solution into the water absorbent resin powder, an acid catalyst, a basic catalyst, water-insoluble fine particles, or a surfactant may be incorporated together to the extent that the effects of the present invention are not impaired, for example, in an amount of 0 parts to 10 parts by weight, preferably 0 parts to 5 parts by weight, and more preferably 0 parts to 1 part by weight. The surfactant used and the use amount thereof are exemplified in U.S. Pat. No. 7,473,739 etc.

The water absorbent resin obtained after incorporation of a surface crosslinking agent is heat treated, and then cooled if necessary. The heating temperature is 70° C. to 300° C., preferably 120° C. to 250° C., and more preferably 150° C. to 250° C. The heating time is preferably 1 minute to 2 hours.

Through such surface crosslinking, in the case of a water absorbent resin powder, the absorption capacity under load (AAP) that will be described below may be increased to preferably 20 [g/g] or greater, or 23 to 30 [g/g].

(2-8) Fine Powder Recycling Step

The water absorbent resin obtained after the polymerization step, preferably after the heating and drying step, is adjusted to have the particle size described above by going through a pulverization step and a classification step as necessary. Furthermore, the coarse particles (for example, 1 mm or greater) to be removed by classification may be pulverized if necessary, and the fine particles (for example, less than 150 µm, or less than 106 µm) to be removed by classification may be discarded, may be used in other applications, or may be subjected to fine powder recycling.

That is, the production method of the present invention may preferably include a fine powder recycling step. The fine powder recycling step refers to a step of separating the fine powder (particularly, a fine powder containing 70% by weight or more of a powder having a particle size of 150 µM or less) that is generated in the drying step and optionally the pulverization and classification steps, and then recycling the fine powder directly, or after hydration or granulation, to a site preceding the pulverization step, preferably to the polymerization step, the fine crush step of the foamed polymer, or the heating and drying step. When the fine powder is recycled, the particle size of the base polymer can be controlled, and also, the water absorption rate can be further enhanced by addition of the fine powder. The fine powder may be a fine powder obtainable before the surface crosslinking, or may be a fine powder obtainable after the surface crosslinking, and the amount of fine powder recycling is appropriately set to 1% to 40% by weight, or 5% to 30% by weight, of the dried product.

The fine powder recycling method that is preferably used in the present invention is a method of mixing a water absorbent resin fine powder, or a hydration product or granulation product thereof, and optionally inorganic fine particles, into the aqueous monomer solution at the time of polymerization or into the hydro gel in the middle of polymerization. Also, foaming may also be promoted by thickening the monomers at the time of polymerization with the fine powder to be recycled.

(2-9) Other Steps

In addition to the steps described above, if necessary, a second classification step, a recycling step for evaporated monomers, a granulation step, a fine powder removal step, and the like may also be provided. Furthermore, in order to obtain an effect of color stability over time, to prevent gel deterioration or the like, the chelating agent and/or reducing agent described below may be used with the monomers or a polymerization product thereof. That is, for the prevention of coloration and the prevention of deterioration, the present invention preferably includes a step of adding a chelate and/or a reducing agent.

The chelating agent and the reducing agent will be described below.

(Chelating Agent)

The water absorbent resin having continuous gas bubbles of the present invention preferably contains a chelating agent from the viewpoints of the resistance to urine and the prevention of coloration. When a chelating agent that is not disclosed in Patent Literature 20 or the like is used, a water absorbent resin containing continuous gas bubbles, which has excellent resistance to urine and excellent coloration prevention, is provided.

The chelating agent of the present invention is preferably a polymer compound or a non-polymer compound in view of the effect, and among them, a non-polymer compound is preferred. Specifically, a compound selected from amino-polyvalent carboxylic acid, organic polyvalent phosphoric acid, inorganic polyvalent phosphoric acid, amino-polyvalent phosphoric acid, and salts thereof is preferred. In view of the effect, the molecular weight of the chelating agent is preferably 100 to 5000, and more preferably 200 to 1000. When the water absorbent resin contains a chelating agent, coloration and deterioration over time of the resin are suppressed.

Here, the polyvalent compound has plural relevant functional groups in one molecule, and preferably has 2 to 30, more preferably 3 to 20, or 4 to 10, relevant functional groups. Furthermore, these chelating agents are preferably water-soluble chelating agents, specifically water-soluble chelating agents that dissolve in 100 g of water (25° C.) in an amount of 1 g or more, and more preferably 10 g or more. Meanwhile, for specific chelating agents and contents thereof and the like, the descriptions of paragraph [0104] to [0111] of WO 2011/040530 A apply correspondingly.

(Organic or Inorganic Reducing Agent)

The water absorbent resin containing continuous gas bubbles according to the present invention preferably contains an organic or inorganic reducing agent, and more preferably an inorganic reducing agent, from the viewpoints of the resistance to urine and the prevention of coloration. Still more preferably, the water absorbent resin contains a water-soluble inorganic compound having a reducing inorganic element or a water-soluble organic compound having a reducing inorganic element as an inorganic reducing agent. Meanwhile, the term "water-soluble" means that the relevant compound dissolves in 100 g of water at 25° C. in an amount of 1 g or more, more preferably 5 g or more, and particularly preferably 10 g or more. When organic or inorganic reducing agents that are not specified in Patent Literature 20 and the like are used, a water absorbent resin containing continuous gas bubbles, which is excellent in terms of residual monomer, coloration or deterioration, is obtained.

Meanwhile, for specific examples of the inorganic reducing agent according to the present invention, the descriptions of paragraph [0114] to [0121] of WO 2011/040530 A apply correspondingly.

Furthermore, according to the purpose, an oxidizing agent, an oxidation inhibitor, water, a polyvalent metal compound, a water-insoluble inorganic or organic powder such as silica, a metal soap, a deodorant, an antibacterial agent, pulp, a thermoplastic fiber, and the like may be added to the water absorbent resin powder in an amount of 0% to 3% by weight, and preferably 0% to 1% by weight, of the water absorbent resin powder. A preferred amount of surfactant in the water absorbent resin powder is in the range described above.

The present invention also provides a polyacrylic acid-type foam-like water absorbent resin containing continuous gas bubbles, particularly a polyacrylic acid-type water absorbent resin having an open gas bubble ratio of 5% or higher, preferably 5% to 98%, and more preferably 5% to 90%. Here, the open gas bubble ratio of the "water absorbent resin" defines the open gas bubble ratio of an "expanded polymer (hydro gel)" or a "water absorbent resin (powder)". Furthermore, an open gas bubble ratio that is particularly preferable to solve the problem is preferably 5% to 30%, and more preferably 5% to 15%, in the case of the water-absorbent resin (powder). Furthermore, in the case of a water absorbent resin molded product (particularly, a sheet-like molded product), the open gas bubble ratio is preferably 5% to 98%, and more preferably 10% to 90%.

Meanwhile, the open gas bubble ratio of the foamed polymer (hydro gel) prior to drying is preferably 5% or higher, and more preferably 5% to 90%. A polymer which dominantly contains continuous gas bubbles almost does not undergo a change in the shape (that is, volume) after drying, and a polymer containing many independent gas bubbles expands and undergoes an increase in volume, while the shape also becomes close to a spherical shape.

Meanwhile, the content of independent gas bubble ratio of the water absorbent resin (powder) in the present invention is not particularly limited, but the independent gas bubble ratio is preferably 5% or higher, more preferably 5% to 25%, and still more preferably 10% to 25%. Furthermore, the independent gas bubble ratio of the foamed polymer (hydro gel) prior to drying is preferably 0% or higher, and more preferably 0% to 20%.

Meanwhile, the constituent other than the independent gas bubbles and the open gas bubbles is the water absorbent resin, and since the sum is 100%, the sum of the independent gas bubble ratio and the open gas bubble ratio is, in the case of a water absorbent resin powder, preferably 10% to 90%, more preferably 10% to 50%, and particularly preferably 10% to 40%. Furthermore, in the case of a water absorbent resin molded product (particularly, a sheet-like molded product), the sum of the independent gas bubble ratio and the open gas bubble ratio is preferably 10% to 98%, more preferably 20% to 90%, and particularly preferably 50% to 90%.

[3] Physical Properties of Polyacrylic Acid-Type Water Absorbent Resin (Powder)

When it is intended to use the water absorbent resin in hygiene materials, particularly disposable diapers, it is preferable that the water absorbent resin have been subjected to polymerization or surface crosslinking, and have at least one of the following items (3-1) to (3-9), more preferably two or more including the AAP, and particularly preferably three or more of the items, controlled. If the conditions described below are not satisfied, the water absorbent resin may not exhibit sufficient performance in high concentration diapers that will be described below.

The production method of the present invention can be suitably applied to the method for producing a water absorbent resin powder that will be described below, but preferably, the production method can be applied to the control and enhancement of the water absorption rate (FSR). Meanwhile, unless stated otherwise, the properties described below and described in Examples are defined by the EDANA method.

In the present invention, the water absorbent resin is preferably a polyacrylic acid-type water absorbent resin powder having a water absorption rate index, which is defined by the following formula, of 90 or greater, and having a bulk density of 0.3 to 0.8 [g/cm³]. Furthermore, it is more preferable that a polyacrylic acid-type water absorbent resin powder having a water absorption rate index, which is defined by the following formula, of 90 or greater, and having a bulk density of 0.3 to 0.8 [g/cm³], be surface crosslinked.

$$\text{Water absorption rate index} = (\text{FSR [g/g/s]}) \times (\text{bulk density [g/cm}^3\text{]}) \times (\text{weight average particle diameter [μm]}) \quad \text{[Formula 6]}$$

provided that FSR represents the water absorption rate obtainable after swelling 20 times in physiological saline.

The water absorption rate index is such that a higher value which increases in the order of 90, 95, 100, 105, 110, 115 and 120, is more preferred, and the upper limit is sufficient at 150, or 140. Such a water absorbent resin powder has excellent liquid permeability or impact resistance, and can be suitably used in water absorbing articles such as disposable diapers. A water absorbent resin having a water absorption rate index that is low, or having a water absorption rate index that is too high on the contrary, tends to be unsuitable for the practical use.

Such a water absorbent resin powder has a foamed structure (also known as: a porous structure), and the porous structure can be judged by checking the particle surface from an electron microscopic photograph. The average pore size at the particle surface is preferably 200 μm or less, and more preferably 0.1 μm to 150 μm, or 1 μm to 100 μm. The main component of the individual powders is porous particles. Furthermore, when the gel is crushed with a kneading pulverizer, the particles have complicated shapes in addition to the shape described above.

(3-1) AAP (Absorption Against Pressure)

In order to prevent leakage into disposable diapers, the absorption capacity (AAP) against a 0.9 wt % aqueous solution of sodium chloride against a pressure of 2.06 kPa, or against a pressure of 4.83 kPa, is controlled to be preferably 20 [g/g] or greater, more preferably 22 [g/g] or greater, and still more preferably 24 [g/g] or greater, by applying the polymerization described above as a means for achieving the prevention. The upper limit of AAP is not particularly limited, but in view of the balance with other physical properties, the upper limit is preferably 40 [g/g] or less. If the AAP is less than 20 [g/g], when such a water absorbent resin is used in an absorbent material, there is a risk that a hygiene article having less return of liquid (usually, referred to as "re-wetting") when pressure is applied to the absorbent material, may not be obtained.

(3-2) CRC (Water Absorption Capacity without Load)

The water absorption capacity without load (CRC) is controlled to be preferably 10 [g/g] or greater, more preferably 20 [g/g] or greater, still more preferably 25 [g/g] or greater, and particularly preferably 30 [g/g] or greater. A higher CRC value is more preferred, and the upper limit of the CRC is not particularly limited. However, in view of the balance with other physical properties, the upper limit is preferably 50 [g/g] or less, more preferably 45 [g/g] or less, and still more preferably 40 [g/g] or less. If the CRC is less than 10 [g/g], there is a risk that the water absorbent resin may have a low amount of water absorption and may not be suitable for the use in the absorbent material in hygiene articles such as disposable diapers. Also, if the CRC exceeds 50 [g/g], when such a water absorbent resin is used in an absorbent material, there is a risk that a hygiene article having an excellent rate of liquid uptake may not be obtained.

(3-3) SFC (Saline Flow Conductivity)

In order to prevent leakage into disposable diapers, the 0.69 wt % saline flow conductivity (SFC) which represents liquid permeability characteristics under pressure, is controlled to be 1 [$\times 10^{-7}$ cm³·s·g⁻¹] or greater, preferably 20 [$\times 10^{-7}$ cm³·s·g⁻¹] or greater, more preferably 50 [$\times 10^{-7}$ cm³·s·g⁻¹] or greater, still more preferably 70 [×10$^{-7}$ cm$^3$·s·g$^{-1}$] or greater, and particularly preferably 100 [×10$^{-7}$ cm$^3$·s·g$^{-1}$] or greater, by applying the polymerization described above as a means for achieving the prevention. The upper limit of the SFC is not particularly limited, but is preferably 3,000 [×10$^{-7}$ cm$^3$·s·g$^{-1}$] or less, and more preferably 2,000 [×10$^{-7}$ cm$^3$·s·g$^{-1}$] or less. If the SFC exceeds 3,000 [×10$^{-7}$ cm$^3$·s·g$^{-1}$], when such a water absorbent resin is used in a water absorbent material, there is a risk that liquid leakage in the absorbent material may occur. The SFC is a well known measurement method, and can be defined according to, for example, U.S. Pat. No. 5,562,646.

The present invention can be suitably applied as a production method for a water absorbent resin powder having enhanced liquid permeability, particularly a high liquid permeability with an SFC value of 20 [×10$^{-7}$ cm$^3$·s·g$^{-1}$] or greater.

(3-4) Ext (Extractables)

The extractables is preferably 0% to 35% by weight or less, more preferably 25% by weight or less, still more preferably 15% by weight or less, and particularly preferably 10% by weight or less. If the Ext is greater than 35% by weight, the gel strength of the obtained water absorbent resin is weak, and there is a risk that liquid permeability may deteriorate. Furthermore, when such a water absorbent resin is used in a water absorbent material, there is a risk that a water absorbent resin which exhibits less return of liquid (re-wetting) when pressure is applied to the water absorbent material, may not be obtained.

FSR (Water Absorption Rate)

The water absorption rate (FSR) of 1 g of a water absorbent resin powder in 20 g of physiological saline is usually 0.1 [g/g/s] or greater, 0.15 [g/g/s] or greater, 0.20 [g/g/s] or greater, 0.25 [g/g/s] or greater, 0.35 [g/g/s] or greater, or 0.45 [g/g/s] or greater. The upper limit is 20 [g/g/s]. The measurement method for the FSR is defined in the Examples described below.

(3-6) Initial Color Hue

The L value of the water absorbent resin is preferably 87 or higher, and more preferably 90 or higher. Since the water absorbent resin according to an embodiment of the present invention has an open gas bubble ratio which is as high as 5% or higher, the L value also increases. Furthermore, when the content of p-methoxyphenol is 60 ppm or less, the L value is further increased.

(3-7) Bulk Density

The bulk density of the water absorbent resin powder is 0.3 to 0.8 [g/cm$^3$], preferably 0.4 to 0.7 [g/cm$^3$], and more preferably 0.5 to 0.7 [g/cm$^3$]. In the present invention, the water absorbent resin has a foamed structure (also known as: a porous structure), and has a lower bulk density as compared with conventional particles that are not foamed.

(3-8) Surface Tension

The surface tension (defined by the measurement method described in the Examples) is preferably 50 [mN/m] or greater, more preferably 55 [mN/m] or greater, 60 [mN/m] or greater, 65 [mN/m] or greater, still more preferably 70 [mN/m] or greater, and particularly 72 [mN/m] or greater. When the surface tension is 72 [mN/m] or greater, there is no substantial decrease in the surface tension. Meanwhile, the upper limit is usually sufficient at 75 [mN/m].

(3-9) Particle Size of Powder

The water absorbent resin may be a molded product, or may be a non-molded product (powder form). When the water absorbent resin is used in a powder form, it is preferable to adopt a particle size distribution in the range described in the above section (2-5). The above-described physical properties are particularly suitably defined when the water absorbent resin is in a powder form.

(3-10) Shape of Molded Product

Figure 6:
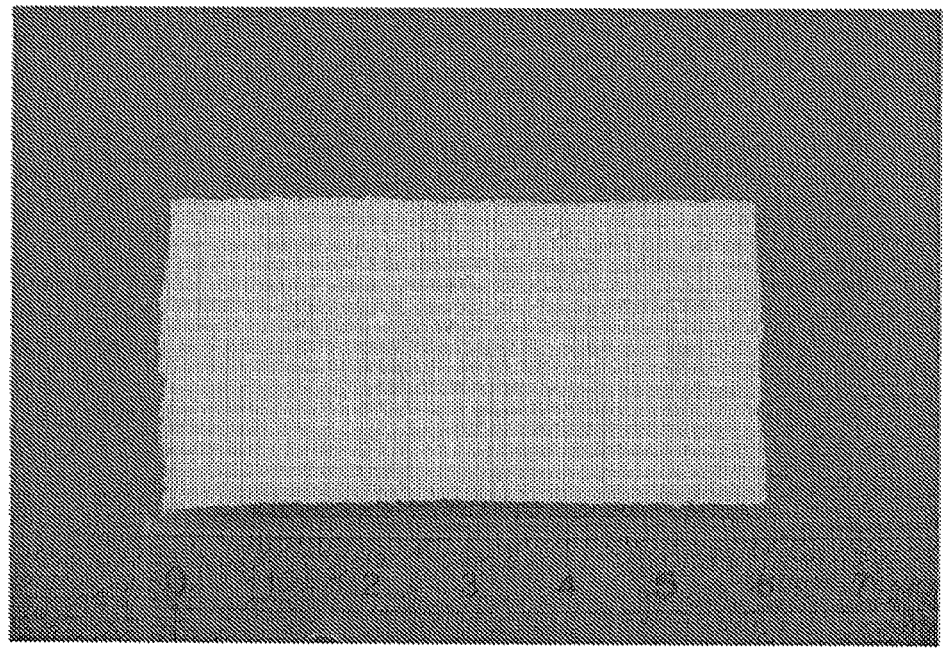
FIG. 6 is a representative shape (sheet form) of water absorbent resin molded products.

When the water absorbent resin is produced into a molded product, the water absorbent resin is preferably produced into the sheet-like product described in the above section (2-6). The shape of the sheet is as described in the above section (2-6), but is not limited thereto. FIG. 6 presents a representative shape (sheet form) of the water absorbent resin molded products.

[4] Use of Polyacrylic Acid-Type Water Absorbent Resin

There are no particular limitations on the use of the water absorbent resin of the present invention, but examples thereof include water retention applications for agriculture and horticulture, applications for solidifying waste liquid, industrial applications, hygiene material applications, and the like. Since the water absorbent resin of the present invention has excellent air permeability and an excellent water absorption rate and is white in color, the water absorbent resin can be used preferably in absorbing articles such as disposable diapers, sanitary napkins, and incontinence pads; more preferably in absorbing articles for hygiene materials; and particularly preferably in disposable diapers. Furthermore, if the water absorbent resin of the present invention is in a sheet form, the water absorbent resin can be directly used as an absorbent material (an absorbent core) having shape retention. Also, even if the water absorbent resin is in a powder form, since there is no excessive decrease in the bulk density, the water absorbent resin can be used in thin disposable diapers.

Since the water absorbent resin of the present invention has characteristics such as described above, the use amount of pulp can be reduced. Therefore, when the content (core concentration) of the water absorbent resin powder in an absorbent material containing other optional absorbent materials (pulp fiber and the like) in an absorbing article is 30% to 100% by weight, preferably 40% to 100% by weight, more preferably 50% to 100% by weight, still more preferably 60% to 100% by weight, particularly preferably 70% to 100% by weight, and most preferably 75% to 95% by weight, the effects of the present invention are exhibited.

[5] Examples

Hereinafter, the present invention will be described by way of Examples, but the present invention is not intended to be construed to be limited to the Examples. Furthermore, unless particularly stated otherwise, each step in the respective Examples was carried out at substantially normal pressure (atmospheric pressure±5%, and more preferably, 1% or less), and identical steps were carried out without applying any pressure change caused by intentional pressurization or pressure reduction. Furthermore, unless particularly stated otherwise, the measurement of physical properties and the like was carried out at room temperature (20° C. to 25° C.) and at a relative humidity of 40% RH to 50% RH.

(5-1) Open (Continuous) Gas Bubble Ratio

The open (continuous) gas bubble ratio related to the present invention was measured according to the method described Shimadzu Corp. HP.

(http://www.shimadzu.co.jp/powder/user/appli/csc221.pdf)

(a) Foamed Polymer

A foamed polymer obtained by carrying out the polymerization step was neatly cut with a sharp knife, and thus a cubic specimen which measured 5 mm on each side was obtained. Subsequently, the geometric (circumscribable shape) volume (va) [cm$^3$] and the surface area (sa) [cm$^2$] of the relevant cubic specimen were determined by measuring the dimensions accurately with vernier calipers. On the other hand, the specimen volume (Va) [cm$^3$] of the cubic specimen was measured by using a dry type densitometer (manufactured by Shimadzu Corp.; AccuPyc 11-1340). Meanwhile, the specimen volume (Va) is defined by the value obtained by subtracting the volume of open gas bubbles (including those independent gas bubbles that have turned into open gas bubbles at the time of fabricating the cubic specimen) from the geometric (circumscribable shape) volume (va).

Subsequently, the cubic specimen was further finely cut, and the geometric (circumscribable shape) volume (v'a) [cm$^3$] and the surface area (s'a) [cm$^2$] of a finely cut specimen were determined by using the dimensions measured with vernier calipers. Furthermore, the specimen volume (V'a) [cm$^3$] was determined by using a dry type densitometer.

The following simultaneous equations were established by using the values obtained by the operation described above, and the volume of open gas bubbles per unit volume, (Voa) [cm$^3$/cm$^3$], and the volume per unit area of (independent) gas bubbles that are opened by cutting the foamed polymer, (Vca) [cm$^3$/cm$^2$], were determined.

$$\begin{cases} Va \ [\text{cm}^3] = va - va \times Voa - sa \times Vca \\ V'a \ [\text{cm}^3] = v'a - v'a \times Voa - s'a \times Vca \end{cases} \quad [\text{Formula 7}]$$

wherein in the above formula, (va×Voa) and (v'a×Voa) each represent the volume [cm$^3$] of open gas bubbles, and (sa×Vca) and (s'a×Vca) each represent the volume [cm$^3$] of (independent) gas bubbles that are opened in the course of preparing the specimen.

As discussed above, the open (continuous) gas bubble ratio (Voa×100 [%]) of a foamed polymer is determined.

(b) Water Absorbent Resin (Powder)

A foamed polymer obtained by carrying out the polymerization step was neatly cut with a sharp knife, and thus a cubic specimen which measured 2 mm on each side was obtained. Thereafter, the cubic sample was dried in a hot air dryer (temperature: 180° C., air velocity: 2.0 [m/s], for 30 minutes) and pulverized with a roll mill, and thus a particulate water absorbent resin (powder) was obtained.

Next, the particulate water absorbent resin (powder) was classified by using JIS standard sieves (JIS Z8801-1 (2000)) having mesh sizes of 850 μm, 710 μm, 600 μm, 500 μm, 425 μm, 300 μm, 212 μm, 150 μm, and 45 μm, and a fraction of particles having a particle size of greater than or equal to 500 μm and less than 600 μm, and a fraction of particles having a particle size of greater than or equal to 300 μm and less than 425 μm were taken out.

For the two kinds of fractions, the geometric (circumscribable shape) (vb, v'b) [cm$^3$] and surface area (sb, s'b) [cm$^2$] were calculated by assuming the particles of each fraction as spheres. That is, the particles of the fraction with a particle size of greater than or equal to 500 μm and less than 600 μm were assumed to be spheres having a diameter of 550 μm, and the particles of the fraction with a particle size of greater than or equal to 300 μm and less than 425 μm were assumed to be spheres having a diameter of 362.5 μM.

Furthermore, the specimen volume (Vb, V'b) [cm$^3$] per one grain of each of the fractions was measured by using a dry type densitometer, in the same manner as in the case of the foamed polymer. That is, the total weight of each fraction and the weight of a known number of particles (for example, 100 particles) are measured to determine the weight per one grain, and thus the total number of particles of each fraction can be found. Further, the specimen volume per one grain (Vb, V'b) [cm$^3$] is determined from the value obtained with a dry densitometer.

The following simultaneous equations were established by using the values obtained by the operation described above, and thus the volume of open gas bubbles per unit volume, (Vob) [cm$^3$/cm$^3$], and the volume of (independent) gas bubbles per unit area that is (assumed to be) opened in the course of preparing the specimen, (Vcb) [cm$^3$/cm$^2$], were determined.

$$\begin{cases} Vb \ [\text{cm}^3] = vb - vb \times Vob - sb \times Vcb \\ V'b \ [\text{cm}^3] = v'b - v'b \times Vob - s'b \times Vcb \end{cases} \quad [\text{Formula 8}]$$

wherein in the above formula, (vb×Vob) and (v'b×Vob) each represent the volume [cm$^3$] of open gas bubbles, and (sb×Vcb) and (s'b×Vcb) each represent the volume [cm$^3$] of (independent) gas bubbles that are (assumed to be) opened in the course of preparing the specimen.

As discussed above, the open (continuous) gas bubble ratio (Vob×100 [%]) of a water absorbent resin (powder) is determined.

(5-2) Independent Gas Bubble Ratio (a) Foamed Polymer

A foamed polymer was neatly cut with a sharp knife, and thus a cubic specimen which measured 5 mm on each side was obtained. Subsequently, the geometric (circumscribable shape) volume (Vga) [cm$^3$] of the cubic specimen was determined by accurately measuring the dimensions by using vernier calipers. Furthermore, the weight of the cubic specimen, Wa [g], was measured.

Next, the moisture content αa [wt %] of the cubic specimen was determined by the method disclosed in section (5-5). Subsequently, the cubic specimen which was dried after the moisture content was determined was finely pulverized by the method disclosed in section (5-13) until a particle size of 45 μm or less was obtained. Thereby, the true density [g/cm$^3$] of the water absorbent resin portion was determined (see FIG. 8). Furthermore, the true density Da [g/cm$^3$] of the cubic specimen was calculated from the specific gravity of water (1.00 [g/cm$^3$]) according to the following formula.

$$Da \ [\text{g/cm}^3] = \{(100-\alpha a) \times (\text{true density of water absorbent resin portion}) + \alpha a\}/100 \quad [\text{Formula 9}]$$

Furthermore, from the geometric (circumscribable shape) volume (Vga) [cm$^3$], weight Wa [g], and true density Da [g/cm$^3$] of the cubic specimen, and the open (continuous) gas bubble ratio (Voa [%]) of the foamed polymer determined in the section (5-1), the independent gas bubble ratio (Vc [%]) of the foamed polymer was determined according to the following formula.

$$Vc \ [\%] = \{(Vga - Wa/Da - Voa)\}/Vga \times 100 \quad [\text{Formula 10}]$$

(b) Case of Water Absorbent Resin (Powder)

A foamed polymer was neatly cut with a sharp knife, and thus a cubic specimen which measured 2 mm on each side was obtained. Thereafter, the cubic specimen was dried in a hot air dryer (temperature: 180° C., air velocity: 2.0 [m/s], for 30 minutes) and pulverized with a roll mill, and thus a particulate water absorbent resin (powder) was obtained.

Next, the particulate water absorbent resin (powder) was classified by using JIS standard sieves (JIS Z8801-1 (2000)) having mesh sizes of 850 μm, 710 μm, 600 μm, 500 μm, 425 μm, 300 μm, 212 μm, 150 μm, and 45 μm, and a fraction of particles having a particle size of greater than or equal to 500 µm and less than 600 µm, and a fraction of particles having a particle size of less than 45 µm were taken out.

For the fraction of particles having a particle size of less than 45 µm, the density [g/cm³] was determined from the weight [g] and volume [cm³] of the entirety, and this was designated as the true density of the water absorbent resin portion of the water absorbent resin (powder). Furthermore, the true density Db [g/cm³] of the water absorbent resin (powder) was calculated from the moisture content αb [wt %] by the method described in section (5-5), according to the following formula.

$$Db\ [g/cm^3]=\{(100-\alpha b)\times(\text{true density of water absorbent resin portion})+\alpha b\}/100 \quad \text{[Formula 11]}$$

Furthermore, from the geometric (circumscribable shape) volume (Vgb) [cm³] (similarly to the section (5-1)(b), the particles of the fraction were assumed to be spheres; therefore, Vgb is the volume of a sphere having a diameter of 550 µm), weight Wb [g], and the true density Db [g/cm³] for the fraction of particles having a particle size of greater than or equal to 500 µm and less than 600 µm, and the open (continuous) gas bubble ratio (Vob [%]) of the water absorbent resin (powder) determined in the section (5-1), the independent gas bubble ratio (Vd [%]) of the water absorbent resin (powder) was determined according to the following formula.

$$Vd\ [\%]=(Vgb-Wb/Db-Vgb\times Vob)\times 100/Vgb \quad \text{[Formula 12]}$$

(5-3) Weight Average Particle Diameter (D50) and Logarithmic Standard Deviation (σζ) of Particle Size Distribution The weight average particle diameter (D50) and the logarithmic standard deviation (σζ) of the particle size distribution of the water absorbent resin (powder) according to the present invention were measured according to the following procedure.

That is, 10.0 g of a water absorbent resin (powder) was fed to JIS standard sieves (the IIDA Testing Sieve: diameter 8 cm/JIS Z8801-1 (2000)) having mesh sizes of 850 µm, 710 µm, 600 µm, 500 µm, 425 µm, 300 µm, 212 µm, 150 µm and 45 µm, under the conditions of room temperature (23±2° C.) and a humidity of 50 RH %, and a vibrating classifier (IIDA Sieve Shaker; Type ES-65/SER. No. 0501) was operated at a number of rotations of 60 Hz, 230 rpm/a number of impacts of 60 Hz, 130 rpm to classify the particles for 5 minutes. Subsequently, the residual percentage R was plotted on a logarithmic probability paper, and the particle size corresponding to R=50% by weight was read as the weight average particle diameter (D50). Furthermore, the logarithmic standard deviation (σζ) of the particle size distribution can be determined by the following formula, and a smaller value of σζ means a narrower particular size distribution.

$$\sigma\zeta=0.5\times\ln(X2/X1) \quad \text{[Formula 13]}$$

wherein X1 means the particle size corresponding to R=84.1% by weight, and X2 means the particle size corresponding to R=15.9% by weight.

(5-4) Water Absorption Capacity without Load (CRC)

The water absorption capacity without load (CRC) of the water absorbent resin (powder) according to the present invention was measured according to ERT441.2-02.

That is, 0.200 g (weight: W0 [g]) of a water absorbent resin (powder) was weighed and was uniformly placed in a bag made of a non-woven fabric (60×85 mm), which was heat-sealed. Subsequently, the bag was immersed in 500 ml of a 0.9 wt % aqueous solution of sodium chloride that had been temperature-adjusted to 25±3° C. After 30 minutes passed, the bag was pulled up, and dehydration was carried out by using a centrifuge (centrifuge manufactured by Kokusan Corp.: Model H-122) under the conditions of 250 G for 3 minutes. Thereafter, the weight of the bag (W1 [g]) was measured.

The same operation was carried out without placing a water absorbent resin (powder) in the bag, and the weight of the bag at that time (W2 [g]) was measured. From the values of W0 [g], W1 [g], and W2 [g] thus obtained, the water absorption capacity without load (CRC) was calculated according to the following formula.

$$CRC\ [g/g]=\{(W1-W2)/W0\}-1 \quad \text{[Formula 14]}$$

(5-5) Moisture Content and Solids Content

The moisture content of the water absorbent resin (powder) related to the present invention was measured according to ERT430.2-02.

That is, in an aluminum cup having a diameter of the bottom of about 50 mm, 1.00 g of a water absorbent resin (powder) was weighed, and the total weight W3 [g] of the specimen (the water absorbent resin (powder) and the aluminum cup) was measured. Subsequently, the specimen was left to stand in an airless oven at an atmospheric temperature of 180° C., and thus the water absorbent resin (powder) was dried. After 3 hours passed, the specimen was removed from the oven, and the specimen was cooled to room temperature in a desiccator. Thereafter, the total weight W4 [g] of the specimen after drying (the water absorbent resin (powder) after being dried, and the aluminum cup) was measured, and the moisture content [wt %] was calculated according to the following formula.

$$\text{Moisture content [wt \%]}=(W3-W4)/(\text{weight of water absorbent resin (powder)})\times 100 \quad \text{[Formula 15]}$$

Meanwhile, the solids content can be determined according to the following formula.

$$\text{Solids content [wt \%]}=100-(\text{moisture content}) \quad \text{[Formula 16]}$$

(5-6) Water Absorption Rate (FSR)

The water absorption rate (FSR) of the water absorbent resin (powder) related to the present invention was measured according to the following procedure.

That is, 1.00 g of a water absorbent resin (powder) was placed in a cylindrical container made of glass (diameter: 32 mm to 34 mm, height: 50 mm) with an open top, and the top surface of the water absorbent resin (powder) was made horizontal. At this time, if necessary, the top surface of the water absorbent resin (powder) may be made horizontal by carefully striking the bottom of the glass container, or the like.

Subsequently, 20 g of a 0.90 wt % aqueous solution of sodium chloride that had been temperature-adjusted to 23±0.2° C. was weighed in a 50-ml beaker made of glass, and the total weight of the aqueous solution of sodium chloride and the glass beaker (weight: W5 [g]) was measured. Thereafter, the aqueous solution of sodium chloride was rapidly and carefully poured into the glass beaker containing the water absorbent resin (powder).

Taking the time point where the aqueous solution of sodium chloride poured into the glass beaker was brought into contact with the water absorbent resin (powder), as the starting point, the time taken for the top surface of the aqueous solution of sodium chloride was replaced by the swollen gel of the water absorbent resin (powder) that had absorbed the aqueous solution of sodium chloride (time: is [seconds]) was measured. Furthermore, the top surface state was checked by visual inspection from an angle of about 20°.

Next, the weight of the 50-ml glass beaker that had been emptied after the introduction of the aqueous solution of sodium chloride (weight: W6 [g]) was measured, and the water absorption rate (FSR) [g/g/s]) was calculated according to the following formula.

$$FSR[g/g/s]=(W5-W6)/(ts\times\text{weight of water absorbent resin (powder)}) \quad \text{[Formula 17]}$$

(5-7) Bulk Density

The bulk density of the water absorbent resin (powder) related to the present invention was measured according to JIS K 3362 by using a bulk density analyzer (manufactured by Kuramochi Kagaku Kiki Seisakusho K.K.).

That is, 100.0 g of a water absorbent resin (powder) that had been sufficiently mixed to eliminate any deviation due to particle size was introduced into a funnel closed with a dumper. Subsequently, the dumper was rapidly opened, and the water absorbent resin (powder) was dropped into a receptacle (weight: W7 [g]) having an internal capacity of 100 ml. Subsequently, the bulging portion of the water absorbent resin (powder) was dropped from the receptacle by rubbing with a glass rod, and the weight of the receptacle (weight: W8 [g]) filled with the water absorbent resin (powder) was measured accurately up to the first decimal place. The bulk density [g/ml] was calculated according to the following formula.

$$\text{Bulk density [g/ml]}=(W8-W7)/100 \quad \text{[Formula 18]}$$

(5-8) Surface Tension

The surface tension of the water absorbent resin (powder) related to the present invention was measured according to the following procedure.

That is, in a glass beaker having a capacity of 100 ml that had been sufficiently washed, 50 ml of a 0.9 wt % aqueous solution of sodium chloride (physiological saline) that had been temperature-adjusted to 20° C. was placed, and the surface tension was measured by using a surface tension meter (manufactured by Kruss GmbH; K11 Automatic Surface Tension Meter). Meanwhile, in this measurement, it is necessary that the surface tension reach 71 to 75 [mN/m].

Subsequently, in the glass beaker containing the physiological saline for which the surface tension had been measured, a rotor made of a fluoro resin and having a length of 25 mm, which had been sufficiently washed, and 0.5 g of a water absorbent resin (powder) were introduced, and the content was stirred for 4 minutes at 500 rpm. After 4 minutes passed, stirring was stopped, and the water absorbent resin (powder) that had absorbed water was caused to sediment. Thereafter, the supernatant was subjected to the same operation as described above, and the surface tension was measured. Meanwhile, according to the present invention, a platinum plate method was employed. The platinum plate was sufficiently washed with deionized water before each measurement and was cleaned by heating with a gas burner before use.

(5-9) Liquid Permeability (SFC)

The liquid permeability (SFC) is a well known measurement method, and the measurement was made according to the method disclosed in U.S. Pat. No. 5,562,646.

(5-10) Color Tone Evaluation (Hunter's Lab Colorimetric System)

The color tone evaluation (Hunter's Lab colorimetric system) in the water absorbent resin (powder) related to the present invention was carried out by the technique described below, by using a spectroscopic colorimeter (manufactured by Hunter Laboratories, Inc.; LabScan (registered trademark) XE).

That is, about 5 g of a water absorbent resin (powder) was filled in a sample container for powder and paste having an internal diameter of 30 mm and a height of 12 mm, and the L value (Lightness: brightness index) of the water absorbent resin (powder) surface was measured with the spectroscopic colorimeter. This value was evaluated as the "brightness index (initial)." As this value is larger, the resin becomes white in color. Furthermore, the a value and the b value were also measured at the same time. As these a value and b value are smaller, less coloration occurs, and the color becomes close to a substantially white color. Furthermore, the measurement conditions described above were selected to be suitable for reflection measurement, a standard round whiteboard No. 2 for powder and paste was used as a standard, and a translucent pipe of 30° C. was used. Furthermore, the color hue of a water absorbent resin (powder) obtained immediately after production, or the color hue of a water absorbent resin (powder) that had been stored for a storage period of one year or less under the conditions of 30° C. or lower and a relative humidity of 50% RH or less, was evaluated as the initial color hue.

On the other hand, about 5 g of a water absorbent resin (powder) was filled in the sample container for powder and paste, and then the resin was left to stand for 7 days in a constant humidity thermostat (manufactured by Espec Corp.; small-sized environmental test chamber, model SH-641) adjusted to an atmosphere at 70±1° C. and a relative humidity of 65±1% RH (coloration acceleration test). Thereafter, the L value, a value and b value of the surface of the water absorbent resin (powder) were measured as the color tone after coloration over time (color tone over time), by using the spectroscopic colorimeter described above.

(5-11) Methoxyphenol Compounds in Water Absorbent Resin (Powder)

The methoxyphenol compounds in the water absorbent resin (powder) related to the present invention were measured by the technique described below.

That is, into a plastic container with a lid and having a capacity of 250 mL, in which a rotor having a length of 35 mm was placed, 1.0 g of a water absorbent resin (powder) and 200.0 g of a 0.90 wt % aqueous solution of sodium chloride were introduced, and the contents were stirred for one hour in an atmosphere at 20° C. to 25° C. (room temperature) and a relative humidity of 50±5 RH %. Subsequently, the liquid was filtered by using one sheet of a filter paper (Advantec Toyo Kaisha, Ltd., product name: JIS P 3801, No. 2, thickness: 0.26 mm, retained particle size: 5 μm).

The filtrate obtained by the operation described above is analyzed by high performance liquid chromatography under the following conditions, and thereby, the methoxyphenol compounds in the water absorbent resin (powder) (unit: ppm (relative to the water absorbent resin (powder)) can be quantitatively determined.

TABLE 1

Eluent: Aqueous phosphoric acid solution, 0.35 wt %
Flow rate: 1.0 [ml/min]
Column: Shodex Rspak DM-614
Column temperature: 35° C.
Detector: L4200 UV detector manufactured by Hitachi, Ltd.
Injection: 100 μl (5-12) Chelating Agent in Water Absorbent Resin (Powder)

The chelating agent in the water absorbent resin (powder) related to the present invention was measured by the technique described below.

That is, into a plastic container with a lid and having a capacity of 250 mL, in which a rotor having a length of 35 mm was placed, 1.0 g of a water absorbent resin (powder) and 200.0 g of a 0.90 wt % aqueous solution of sodium chloride were introduced, and the contents were stirred for one hour in an atmosphere at 20° C. to 25° C. (room temperature) and a relative humidity of 50±5 RH %. Subsequently, the liquid was filtered by using one sheet of a filter paper (Advantec Toyo Kaisha, Ltd., product name: JIS P 3801, No. 2, thickness: 0.26 mm, retained particle size: 5 μm).

The filtrate obtained by the operation described above is analyzed by high performance liquid chromatography, and thereby, the chelating agent in the water absorbent resin (powder) (unit: ppm (relative to the water absorbent resin (powder)) can be quantitatively determined.

(5-13) True Density

The true density of the water absorbent resin (powder) related to the present invention was measured by the technique described below.

That is, into a ball mill pot (manufactured by Teraoka Seisakusho Co., Ltd.;

porcelain ball mill pot, product No.: No. 90/internal dimension: diameter 80 mm and height 75 mm, external dimension: diameter 90 mm and height 110 mm), 15.0 g of a water absorbent resin (powder) and 400 g of cylindrical porcelain ball (diameter 13 mm, length 13 mm) were introduced, and the water absorbent resin powder was pulverized by using a ball mill at 60 Hz for 2 hours. Thus, a fine powder of which 70% by weight or more could pass through a JIS standard sieve having a mesh size of 45 μm was obtained. The fine powder pulverized to 45 μm or less was measured by using a dry type densitometer (manufactured by Shimadzu Corp.; Accupyc 11-1340), and the value thus obtained was designated as the true density of the water absorbent resin (powder).

EXAMPLE 1

A solution (A) prepared by mixing 224.0 g of acrylic acid in which the p-methoxyphenol content was adjusted to 70 ppm, 0.48 g of polyethylene glycol diacrylate (number average molecular weight 522), and 0.13 g of 2-hydroxy-2-methyl-1-phenyl-propan-1-one, and a solution (B) prepared by diluting 153.8 g of a 48.5 wt % aqueous solution of sodium hydroxide with 113.2 g of ion-exchanged water, and adding 0.03 g of pentasodium diethylenetriamine pentaacetate as a chelating agent to the dilution, were respectively prepared. Subsequently, the solution (A) was mixed with the solution (B) under stirring with a magnetic stirrer, while heat was removed from the solution (B) in an open system. Thus, an aqueous monomer solution (1') at 45° C. was obtained.

Next, 4.4 g of a 30 wt % aqueous solution of polyoxyethylene sorbitan monostearate (manufactured by Kao Corp.) was added to the aqueous monomer solution (1'), and the mixture was stirred. Thus, an aqueous monomer solution (1) was obtained. The volume of 400 g of the aqueous monomer solution (1) thus obtained was 340 ml. Thereafter, the aqueous monomer solution was further degassed for 20 minutes with nitrogen gas at room temperature.

Subsequently, 4.1 g of a 3.0 wt % aqueous solution of 2,2'-azobis(2-methylpropionamidine) dihydrochloride was added thereto, and then the aqueous monomer solution (1) and nitrogen gas were fluid mixed by using a desktop whip cream machine "Whip Auto (trade name)" (manufactured by Deutsch Hans Kratt GmbH/sold by Aicohsha Manufacturing Co., Ltd.). Thus, gas bubbles of nitrogen gas were dispersed in the aqueous monomer solution (1) (monomer concentration: 53.2% by weight). Furthermore, the volume of 400 g of the aqueous monomer solution (1) having nitrogen gas dispersed therein was 480 ml, and the volumetric expansion factor of the aqueous monomer solution (1) in Example 1 was 1.4 times (=480 ml/340 ml).

Subsequently, 400 g of the aqueous monomer solution (1) that had passed through the Whip Auto was introduced into a vat type container (bottom side: 250 mm×250 mm, height 30 mm, inner surface: clad with a Teflon (registered trademark) sheet) made of stainless steel that had been heated in advance to 90° C. in a system exposed to the atmosphere. Furthermore, a hot plate was used to heat the vat type container made of stainless steel. Thereafter, a polymerization reaction was immediately initiated by performing UV irradiation. Meanwhile, UV irradiation was carried out by using a black light mercury lamp (peak wavelength: 352 nm, Model H400BL manufactured by Toshiba Lighting and Technology Corp.).

During the polymerization reaction, water vapor was generated after about 35 seconds from the initiation of polymerization, and the reaction proceeded under boiling at or above 100° C. During the boiling polymerization, the foamed polymer (1) thus obtained underwent slight volumetric expansion compared with the aqueous monomer solution (1), but since water vapor could easily evaporate from the continuous gas bubbles, there was almost no volumetric change as compared with the aqueous monomer solution (1). Meanwhile, the temperature of the aqueous monomer solution (1) at the time of initiation of polymerization was 40° C. due to heating from the hot plate, or the like. However, thereafter, the temperature increased rapidly as polymerization proceeded, and after about 40 seconds from the initiation of polymerization, the maximum arrival temperature recorded 107° C.

At the time point where the UV irradiation had been conducted for 3 minutes, the foamed polymer (1) was removed from the vat type container made of stainless steel, and the open gas bubble ratio and the independent gas bubble ratio were measured and calculated. The open gas bubble ratio was 14%, and the independent gas bubble ratio was 16%. Meanwhile, the foamed polymer (1) had numerous fine gas bubbles, and formed a steamed bun-like white foam gel due to the gas bubbles.

Next, in order to check the condition from a SEM (scanning electron microscope) photographic image, the foamed polymer (1) was cut with a knife into a cube which measured 5 mm on each side, and the cut foamed polymer was dried in a hot air dryer at a hot air temperature of 180° C. and an air velocity of 2.0 [m/s] for 30 minutes. Thus, a water absorbent resin dried product (1') was obtained.

Figure 4:
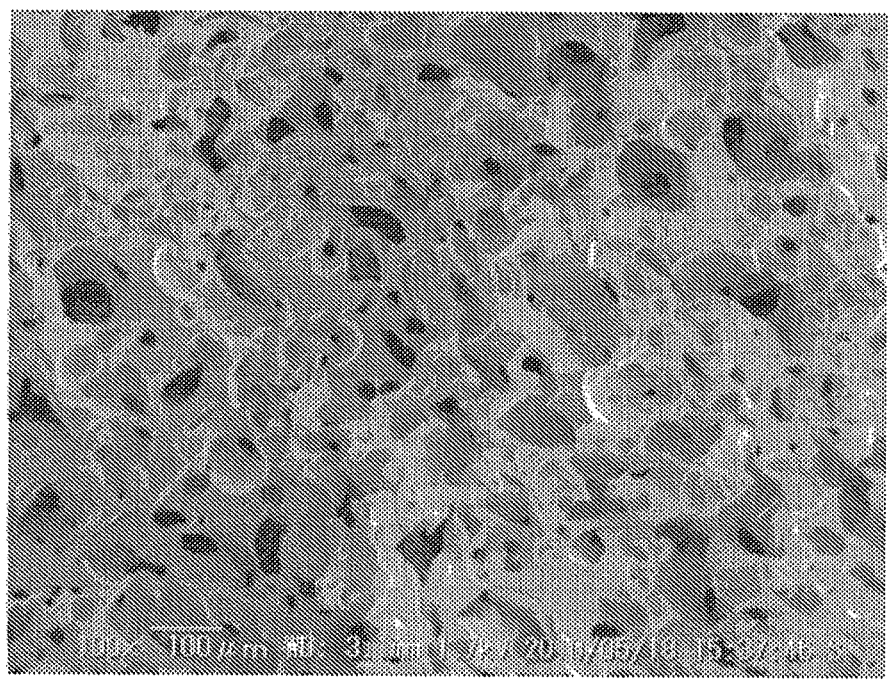
FIG. 4 is a SEM (scanning electron microscope) photographic image of a water absorbent resin dried product (1') according to Example 1.

During the drying step, the foamed polymer (1) (5-mm piece) was such that since water could easily evaporate from the continuous gas bubbles, gel expansion due to drying was not observed, and substantial deformation did not occur, except for slight shrinkage due to drying. The cube-shaped water absorbent resin dried product (1') thus obtained was cut, and a SEM (scanning electron microscope) photographic image for the fractured surface (see FIG. 4) was observed. It was found that continuous gas bubbles had been formed.

Next, separately, the foamed polymer (1) obtained by the operation described above was cut with a knife into a cube which measured 2 mm on each side, and the cut foamed polymer was dried in a hot air dryer at a hot air temperature of 180° C. and an air velocity of 2.0 [m/s] for 30 minutes. Thus, a cube-shaped water absorbent resin dried product (1) was obtained.

Thereafter, the water absorbent resin dried product (1) was further pulverized with a roll mill, and subsequently, the pulverized product was classified with JIS standard sieves having mesh sizes of 600 μm and 300 μm. Thereby, a water absorbent resin powder (1) having a weight average particle diameter (D50) of 460 μm was obtained. Various physical properties of the water absorbent resin powder (1) thus obtained are presented in Table 1. Furthermore, the open gas bubble ratio and the independent gas bubble ratio of the water absorbent resin powder (1) were separately measured by applying the methods described in the above sections (5-1) and (5-2) to the water absorbent resin dried product (1) (measurement was made in the same manner in the following Examples and Comparative Examples). As a result, the open gas bubble ratio was 6%, and the independent gas bubble ratio was 16%.

EXAMPLE 2

Addition of a Step of Uniforming Gas Bubbles

The same operation as that carried out in Example 1 was carried out, and thereby an aqueous monomer solution (2) (monomer concentration: 53.2% by weight, volumetric expansion factor: 1.4 times) containing gas bubbles of nitrogen gas dispersed therein was obtained.

Thereafter, the same operation as that carried out in Example 1 was carried out, except that while nitrogen gas was further continuously incorporated, the aqueous monomer solution (2) was circulated, and uniforming gas bubbles was carried out (see FIG. 1). Thus, a foamed polymer (2) was obtained. At the time of polymerization, after about 40 seconds from the initiation of polymerization, the maximum arrival temperature recorded 107° C. Furthermore, the open gas bubble ratio of the foamed polymer (2) was 12%, and the independent gas bubble ratio was 14%. Furthermore, the foamed polymer (2) had numerous fine gas bubbles, and formed a steamed bun-like white foam gel due to the gas bubbles.

Next, in order to check the condition from a SEM (scanning electron microscope) photographic image, the foamed polymer (2) was cut with a knife into a cube which measured 5 mm on each side, and the cut foamed polymer was subjected to the same hot air drying as that carried out in Example 1. Thus, a water absorbent resin dried product (2') was obtained.

During the drying step, the foamed polymer (2) (5-mm piece) was such that since water could easily evaporate from the continuous gas bubbles, gel expansion due to drying was not observed, and substantial deformation did not occur, except for slight shrinkage due to drying. The water absorbent resin dried product (2') thus obtained was cut, and a SEM (scanning electron microscope) photographic image for the fractured surface was observed. It was found that continuous gas bubbles had been formed.

Next, separately, the foamed polymer (2) obtained by the operation described above was cut with a knife into a cube which measured 2 mm on each side, and the cut foamed polymer was subjected to the same hot air drying as that carried out in Example 1. Thus, a cube-shaped water absorbent resin dried product (2) was obtained.

Thereafter, the water absorbent resin dried product (2) was further subjected to the same pulverization and classification steps as those carried out in Example 1. Thereby, a water absorbent resin powder (2) having a weight average particle diameter (D50) of 460 μm was obtained. Various physical properties of the water absorbent resin powder (2) thus obtained are presented in Table 1. Furthermore, the open gas bubble ratio of the water absorbent resin powder (2) was 6%, and the independent gas bubble ratio was 13%.

EXAMPLE 3

Volumetric Expansion Factor: 1.3 Times

The same operation as that carried out in Example 1 was carried out, except that as compared to Example 1, the use amount of the 30 wt % aqueous solution of polyoxyethylene sorbitan monostearate (manufactured by Kao Corp.) was changed from 4.4 g (Example 1) to 0.80 g (the content per monomer was 0.09% by weight), and also, simultaneously 2.65 g of hydroxyethyl cellulose (Wako First Grade/manufactured by Wako Pure Chemical Industries, Ltd.) was added to obtain an aqueous monomer solution (3) (monomer concentration: 53.5% by weight, volumetric expansion factor: 1.3 times). Thus, a foamed polymer (3) was obtained. At the time of polymerization, after about 40 seconds from the initiation of polymerization, the maximum arrival temperature recorded 107° C. Furthermore, the open gas bubble ratio of the foamed polymer (3) was 10%, and the independent gas bubble ratio was 11%. Furthermore, the foamed polymer (3) had numerous fine gas bubbles, and formed a steamed bun-like white foam gel due to the gas bubbles.

Next, in order to check the condition from a SEM (scanning electron microscope) photographic image, the foamed polymer (3) was cut with a knife into a cube which measured 5 mm on each side, and the cut foamed polymer was subjected to the same hot air drying as that carried out in Example 1. Thus, a water absorbent resin dried product (3') was obtained.

During the drying step, similarly to the case of drying of the foamed polymer (1) in Example 1, gel expansion was not observed, and deformation did not occur. The water absorbent resin dried product (3') thus obtained was cut, and a SEM (scanning electron microscope) photographic image for the fractured surface was observed. It was found that continuous gas bubbles had been formed.

Next, separately, the foamed polymer (3) obtained by the operation described above was cut with a knife into a cube which measured 2 mm on each side, and the cut foamed polymer was subjected to the same hot air drying as that carried out in Example 1. Thus, a cube-shaped water absorbent resin dried product (3) was obtained.

Thereafter, the water absorbent resin dried product (3) was further subjected to the same pulverization and classification steps as those carried out in Example 1. Thereby, a water absorbent resin powder (3) having a weight average particle diameter (D50) of 430 μm was obtained. Various physical properties of the water absorbent resin powder (3) thus obtained are presented in Table 1. Furthermore, the open gas bubble ratio of the water absorbent resin powder (3) was 5%, and the independent gas bubble ratio was 10%.

Next, 100 parts by weight of the water absorbent resin powder (3) was mixed with a surface crosslinking agent solution composed of 0.48 parts by weight of 1,4-butanediol, 0.75 parts by weight of propylene glycol, and 4.0 parts by weight of deionized water, by uniformly spraying the solution thereon. Thereafter, the mixture was heat treated at a temperature of 180° C. for 45 minutes, and the resultant was passed through a JIS standard sieve having a mesh size of 600 μm. Thereby, surface-crosslinked water absorbent resin particles (3) were obtained. Meanwhile, the water absorbent resin particles mean a powder of the surface-crosslinked water absorbent resin.

Thereafter, a second surface crosslinking agent mixture liquid composed of 0.80 parts by weight of a 27 wt % aqueous solution of aluminum sulfate (8 wt % in terms of aluminum oxide), 0.134 parts by weight of a 60 wt % aqueous solution of sodium lactate, and 0.016 parts by weight of propylene glycol was added relative to 100 parts by weight of the surface-crosslinked water absorbent resin particles (3). Subsequently, the mixture was dried at a temperature of 60° C. for one hour without air blowing, and the dried product was passed through a JIS standard sieve having a mesh size of 600 μm. Thus, a water absorbent resin (3a) was obtained.

The water absorbent resin (3a) thus obtained was such that the CRC was 26.5 [g/g], the FSR was 0.45 [g/g/s], and the SFC was 117 [×$10^{-7}$·s·cm$^3$·g$^{-1}$]. Furthermore, the open gas bubble ratio of the water absorbent resin (3a) was 5%, the independent gas bubble ratio was 10%, and any change in the gas bubble ratio associated with the surface treatment was not recognized.

Subsequently, 1.66 parts by weight of a 30 wt % aqueous solution of sodium sulfite was added to 100 parts by weight of the water absorbent resin (3a) obtained by the operation described above, and the mixture was mixed. Subsequently, the mixture was left to stand in a hot air dryer at 60° C. for 30 minutes. Thereafter, the resultant was passed through a JIS standard sieve having a mesh size of 600 μm, and thus a water absorbent resin (3b) was obtained. The water absorbent resin (3b) thus obtained had improved coloration property over time and improved resistance to urine, as compared with the water absorbent resin (3a).

EXAMPLE 4

Volumetric Expansion Factor: 1.2 Times

The same operation as that carried out in Example 1 was carried out, except that as compared to Example 1, the 30 wt % aqueous solution of polyoxyethylene sorbitan monostearate (manufactured by Kao Corp.) was not used, but instead, 5.30 g of hydroxyethyl cellulose (Wako First Grade/manufactured by Wako Pure Chemical Industries, Ltd.) was added to obtain an aqueous monomer solution (4) (monomer concentration: 53.5 wt %, volumetric expansion factor: 1.2 times). Thus, a foamed polymer (4) was obtained. At the time of polymerization, after about 40 seconds from the initiation of polymerization, the maximum arrival temperature recorded 107° C. Furthermore, the open gas bubble ratio of the foamed polymer (4) was 7%, and the independent gas bubble ratio was 9%. Furthermore, the foamed polymer (4) had numerous fine gas bubbles, and formed a steamed bun-like white foam gel due to the gas bubbles.

Next, in order to check the condition from a SEM (scanning electron microscope) photographic image, the foamed polymer (4) was cut with a knife into a cube which measured 5 mm on each side, and the cut foamed polymer was subjected to the same hot air drying as that carried out in Example 1. Thus, a water absorbent resin dried product (4') was obtained.

During the drying step, similarly to the case of drying of the foamed polymer (1) in Example 1, gel expansion was not observed, and deformation did not occur. The water absorbent resin dried product (4') thus obtained was cut, and a SEM (scanning electron microscope) photographic image for the fractured surface was observed. It was found that continuous gas bubbles had been formed.

Next, separately, the foamed polymer (4) obtained by the operation described above was cut with a knife into a cube which measured 2 mm on each side, and the cut foamed polymer was subjected to the same hot air drying as that carried out in Example 1. Thus, a cube-shaped water absorbent resin dried product (4) was obtained.

Thereafter, the water absorbent resin dried product (4) was further subjected to the same pulverization and classification steps as those carried out in Example 1. Thereby, a water absorbent resin powder (4) having a weight average particle diameter (D50) of 440 μm was obtained. Various physical properties of the water absorbent resin powder (4) thus obtained are presented in Table 1. Furthermore, the open gas bubble ratio of the water absorbent resin powder (4) was 5%, and the independent gas bubble ratio was 9%.

EXAMPLE 5

Monomer Concentration: 42.6% by Weight

A solution (C) prepared by mixing 177.50 g of acrylic acid, 0.77 g of polyethylene glycol diacrylate (number average molecular weight 522), and 0.11 g of 2-hydroxy-2-methyl-1-phenyl-propan-1-one, and a solution (D) prepared by diluting 121.89 g of a 48.5 wt % aqueous solution of sodium hydroxide with 180.30 g of ion-exchanged water, and further adding 0.02 g of pentasodium diethylenetriamine pentaacetate, were respectively prepared, and then the solution (C) was mixed with the solution (D) under stirring with a magnetic stirrer while heat was removed from the solution (D) in an open system. Thus, an aqueous monomer solution (5') at 45° C. was obtained.

Next, 7.00 g of a 30 wt % aqueous solution of polyoxyethylene sorbitan monostearate (manufactured by Kao Corp.) and 4.20 g of hydroxyethyl cellulose (Wako First Oracle/manufactured by Wako Pure Chemical Industries, Ltd.) were added to the aqueous monomer solution (5'), and the mixture was stirred. Thus, an aqueous monomer solution (5) was obtained. The volume of 400 g of the aqueous monomer solution (5) thus obtained was 345 ml. Thereafter, the aqueous monomer solution was further degassed for 20 minutes with nitrogen gas.

Subsequently, 8.21 g of a 3.0 wt % aqueous solution of 2,2'-azobis(2-methylpropionamidine) dihydrochloride was added thereto, and then the aqueous monomer solution (5) and nitrogen gas were fluid mixed by using a desktop whip cream machine "Whip Auto (trade name)" in the same manner as in Example 1. Thus, gas bubbles of nitrogen gas were dispersed in the aqueous monomer solution (5) (monomer concentration: 42.6% by weight). Furthermore, the volume of 400 g of the aqueous monomer solution (5) having nitrogen gas dispersed therein was 3300 ml, and the volumetric expansion factor of the aqueous monomer solution (5) in Example 5 was 9.6 times (=3300 ml/345 ml).

Subsequently, 400 g of the aqueous monomer solution (5) that had passed through the Whip Auto was introduced into a vat type container made of stainless steel used in Example 1 that had been heated in advance to 90° C. with a hot plate in a system exposed to the atmosphere. Thereafter, a polymerization reaction was immediately initiated by performing UV irradiation by using a black light mercury lamp in the same manner as in Example 1.

During the polymerization reaction, water vapor was generated after about 40 seconds from the initiation of polymerization, and the reaction proceeded under boiling at or above 100° C. The white foamed polymer (5) thus obtained in the boiling polymerization underwent slight volumetric expansion compared with the aqueous monomer solution (5), but since water vapor could easily evaporate from the continuous gas bubbles, there was almost no volumetric change. Meanwhile, the temperature of the aqueous monomer solution (5) at the time of initiation of polymerization was 40° C. due to heating from the hot plate, or the like. However, thereafter, the temperature increased rapidly as polymerization proceeded, and after about 50 seconds from the initiation of polymerization, the maximum arrival temperature recorded 101° C.

At the time point where the UV irradiation had been conducted for 3 minutes, the foamed polymer (5) was removed from the vat type container made of stainless steel, and the open gas bubble ratio and the independent gas bubble ratio were measured and calculated. The open gas bubble ratio was 87%, and the independent gas bubble ratio was 0%.

Next, in order to check the condition from a SEM (scanning electron microscope) photographic image, the foamed polymer (5) was cut with a knife into a cube which measured 5 mm on each side, and the cut foamed polymer was subjected to the same hot air drying as that carried out in Example 1. Thus, a water absorbent resin dried product (5') was obtained.

Figure 5:
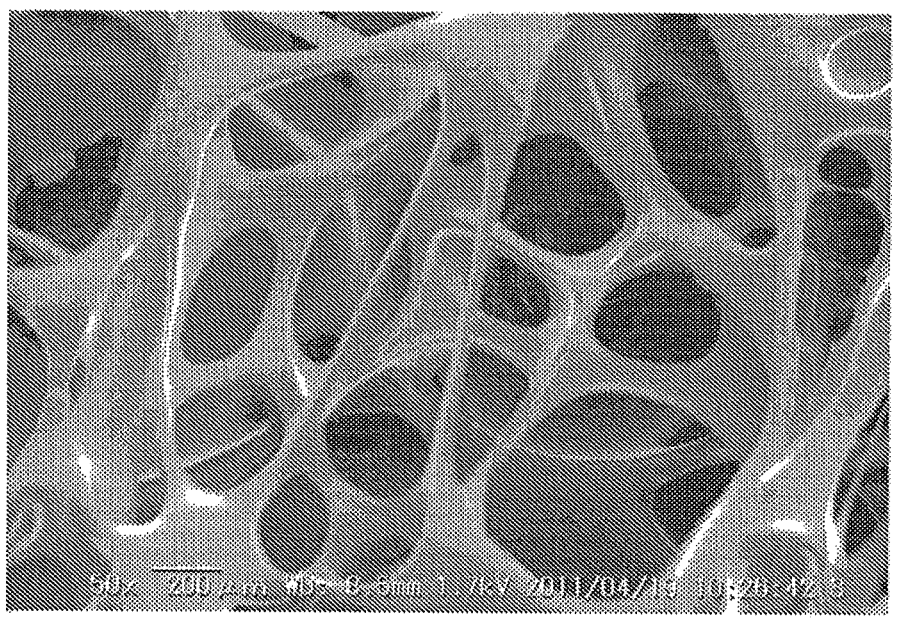
FIG. 5 is a SEM (scanning electron microscope) photographic image of a water absorbent resin dried product (5') according to Example 5.

During the drying step, similarly to the case of drying of the foamed polymer (1) in Example 1, gel expansion was not observed, and substantial deformation did not occur except for slight shrinkage due to drying. The water absorbent resin dried product (5') thus obtained was cut, and a SEM (scanning electron microscope) photographic image (FIG. 5) for the fractured surface was observed. It was found that continuous gas bubbles had been formed.

Comparative Example 1

Monomer Concentration: 37.3% by Weight

A solution (E) prepared by mixing 150.5 g of acrylic acid, 1.86 g of trimethylolpropane triacrylate, and 0.09 g of 2-hydroxy-2-methyl-1-phenyl-propan-1-one, and a solution (F) prepared by diluting 129.2 g of a 48.5 wt % aqueous solution of sodium hydroxide with 205.1 g of ion-exchanged water, and further adding 0.02 g of pentasodium diethylenetriamine pentaacetate, were respectively prepared, and then the solution (E) was mixed with the solution (F) under stirring with a magnetic stirrer while heat was removed from the solution (F) in an open system. Thus, a comparative aqueous monomer solution (1') at 30° C. was obtained.

Next, 6.2 g of a 30 wt % aqueous solution of polyoxyethylene sorbitan monostearate (manufactured by Kao Corp.) was added to the comparative aqueous monomer solution (1'), and the mixture was stirred. Thus, a comparative aqueous monomer solution (1) was obtained. The volume of 100 g of the comparative aqueous monomer solution (1) thus obtained was 90 ml. Thereafter, the comparative aqueous monomer solution was further degassed for 20 minutes with nitrogen gas.

Subsequently, 7.0 g of a 3.0 wt % aqueous solution of 2,2'-azobis(2-methylpropionamidine) dihydrochloride was added thereto, and then the comparative aqueous monomer solution (1) and nitrogen gas were fluid mixed by using a desktop whip cream machine "Whip Auto (trade name)" in the same manner as in Example 1. Thus, gas bubbles of nitrogen gas were dispersed in the comparative aqueous monomer solution (1) (monomer concentration: 37.3% by weight). Furthermore, the volume of 100 g of the comparative aqueous monomer solution (1) having nitrogen gas dispersed therein was 920 ml, and the volumetric expansion factor of the comparative aqueous monomer solution (1) in Comparative Example 1 was 10.2 times (=920 ml/90 ml).

Subsequently, 100 g of the comparative aqueous monomer solution (1) that had passed through the Whip Auto was introduced into a vat type container made of stainless steel used in Example 1 that had been heated in advance to 90° C. with a hot plate in a system exposed to the atmosphere. Thereafter, a polymerization reaction was immediately initiated by performing UV irradiation by using a black light mercury lamp in the same manner as in Example 1.

However, immediately after the comparative aqueous monomer solution (1) was introduced into the vat type container made of stainless steel, it was recognized that integration of gas bubbles progressed, and anti-foaming occurred. Furthermore, anti-foaming further progressed along with an increase in the temperature.

At the time point where the UV irradiation had been conducted for 3 minutes, the comparative polymer (1) was removed from the vat type container made of stainless steel. However, a white foam-like gel caused by gas bubbles such as in the cases of Examples 1 to 5 was not formed, and since the gel did not contain gas bubbles, the gel was almost transparent. From the record of change in the temperature of the polymerization system, the maximum arrival temperature at the time of polymerization was 97° C. (after about 100 seconds from the initiation of polymerization).

Next, in order to check the condition from a SEM (scanning electron microscope) photographic image, the comparative polymer (1) was cut with a knife into a cube which measured 5 mm on each side, and the cut comparative polymer was subjected to the same hot air drying as that carried out in Example 1. Thus, a comparative water absorbent resin dried product (1') was obtained.

During the drying step, since the comparative polymer (1) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying. The comparative water absorbent resin dried product (1') thus obtained was cut, and a SEM (scanning electron microscope) photographic image for the fractured surface was observed. However, continuous gas bubbles were not recognized.

Comparative Example 2

Volumetric Expansion Factor: 1.0 Times

The same operation as that carried out in Example 1 was carried out, except that as compared to Example 1, a comparative aqueous monomer solution (2) (monomer concentration: 53.5% by weight, volumetric expansion factor: 1.0 times) was obtained without using the 30 wt % aqueous solution of polyoxyethylene sorbitan monostearate (manufactured by Kao Corp.). Thus, a comparative polymer (2) was obtained. At the time of polymerization, when the temperature change of the polymerization system was recorded, the maximum arrival temperature at the time of polymerization recorded 107° C. (after about 40 seconds from the initiation of polymerization). Furthermore, the comparative polymer (2) was such that although polymerization was carried out in the same manner as in Example 1, a white foam-like gel caused by gas bubbles was not formed, and since the gel did not contain gas bubbles, the gel was an almost transparent gel.

Next, in order to check the condition from a SEM (scanning electron microscope) photographic image, the comparative polymer (2) was cut with a knife into a cube which measured 5 mm on each side, and the cut comparative polymer was subjected to the same hot air drying as that carried out in Example 1. Thus, a comparative water absorbent resin dried product (2') was obtained.

During the drying step, since the comparative polymer (2) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying step. The comparative water absorbent resin dried product (2') thus obtained was cut, and a SEM (scanning electron microscope) photographic image for the fractured surface was observed. However, continuous gas bubbles were not recognized.

Next, separately, the comparative polymer (2) obtained by the operation described above was cut with a knife into a cube which measured 2 mm on each side, and the cut comparative polymer was subjected to the same hot air drying as that carried out in Example 1. Thus, a cube-shaped comparative water absorbent resin dried product (2) was obtained.

Thereafter, the comparative water absorbent resin dried product (2) was further subjected to the same pulverization and classification steps as those carried out in Example 1. Thereby, a comparative water absorbent resin powder (2) having a weight average particle diameter (D50) of 470 μm was obtained. Various physical properties of the comparative water absorbent resin powder (2) thus obtained are presented in Table 1. Furthermore, the open gas bubble ratio of the comparative water absorbent resin powder (2) was 1.5%, and the independent gas bubble ratio was 4%.

Next, the comparative water absorbent resin powder (2) was subjected to the same surface treatment as that carried out in Example 3, and thereby a comparative water absorbent resin (2) was obtained.

The CRC of the comparative water absorbent resin (2) was 26.3 [g/g], the FSR was 0.18 [g/g/s], and the SFC was 135 [$\times 10^{-7} \cdot s \cdot cm^3 \cdot g^{-1}$]. Furthermore, the open gas bubble ratio of the comparative water absorbent resin (2) was 1.3%, and the independent gas bubble ratio was 4.2%.

From a comparison of Example 3 (FSR: 0.45 [g/g/s]) and Comparative Example 2 (FSR: 0.18 [g/g/s]) which had been subjected to the same surface crosslinking, it was found that in the present invention, the water absorption rate (FSR) obtained after the surface crosslinking improved 2.5 times.

Comparative Example 3

Volumetric Expansion Factor: 1.0 Times

The same operation as that carried out in Example 1 was carried out, except that as compared to Example 1, a comparative aqueous monomer solution (3) (monomer concentration: 53.2% by weight, volumetric expansion factor: 1.0 times) was obtained without carrying out the dispersion of gas bubbles of nitrogen gas in the aqueous monomer solution using the Whip Auto. Thus, a comparative polymer (3) was obtained. At the time of polymerization, when the temperature change of the polymerization system was recorded, the maximum arrival temperature at the time of polymerization recorded 107° C. (after about 40 seconds from the initiation of polymerization). Furthermore, the comparative polymer (3) was such that although polymerization was carried out in the same manner as in Example 1, a white foam-like gel caused by gas bubbles was not formed, and since the gel did not contain gas bubbles, the gel was an almost transparent gel.

Next, in order to check the condition from a SEM (scanning electron microscope) photographic image, the comparative polymer (3) was cut with a knife into a cube which measured 5 mm on each side, and the cut comparative polymer was subjected to the same hot air drying as that carried out in Example 1. Thus, a comparative water absorbent resin dried product (3') was obtained.

During the drying step, since the comparative polymer (3) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying step. The comparative water absorbent resin dried product (3') thus obtained was cut, and a SEM (scanning electron microscope) photographic image for the fractured surface was observed. However, continuous gas bubbles were not recognized.

Comparative Example 4

A comparative aqueous monomer solution (4) and nitrogen gas were fluid mixed by using a "Whip Auto (trade name)" in the same manner as in Example 1, but without adding a 3.0 wt % aqueous solution of 2,2'-azobis(2-methylpropionamidine) dihydrochloride. Thus, gas bubbles of nitrogen gas were dispersed in the comparative aqueous monomer solution (4) (monomer concentration: 53.6% by weight, volumetric expansion factor: 1.4 times).

Next, 400 g of the comparative aqueous monomer solution (4) that had passed through the Whip Auto was introduced into the vat type container made of stainless steel used in Example 1 in a system exposed to the atmosphere. Thereafter, a polymerization reaction was immediately initiated by performing UV irradiation by using a black light mercury lamp in the same manner as in Example 1.

The polymerization was completed by repeating an operation of stopping UV irradiation at the time point when the monomer temperature increased to 80° C. and resuming UV irradiation at the time point when the monomer temperature decreased to 60° C., and thus a comparative polymer (4) was obtained.

Next, in order to check the condition from a SEM (scanning electron microscope) photographic image, the comparative polymer (4) was cut with a knife into a cube which measured 5 mm on each side, and the cut comparative polymer was subjected to the same hot air drying as that carried out in Example 1. Thus, a comparative water absorbent resin dried product (4') was obtained.

During the drying step, since the comparative polymer (4) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying. The comparative water absorbent resin dried product (4') thus obtained was cut, and a SEM (scanning electron microscope) photographic image for the fractured surface was observed. However, continuous gas bubbles were not recognized.

Next, separately, the comparative polymer (4) obtained by the operation described above was cut with a knife into a cube which measured 2 mm on each side, and the cut comparative polymer was subjected to the same hot air drying as that carried out in Example 1. Thus, a cube-shaped comparative water absorbent resin dried product (4) was obtained.

Thereafter, the comparative water absorbent resin dried product (4) was further subjected to the same pulverization and classification steps as those carried out in Example 1. Thereby, a comparative water absorbent resin powder (4) having a weight average particle diameter (D50) of 470 μm was obtained. Various properties of the comparative water absorbent resin powder (4) thus obtained are presented in Table 1. Furthermore, the open gas bubble ratio of the comparative water absorbent resin powder (4) was 2%, and the independent gas bubble ratio was 5%.

Comparative Example 5

Monomer Concentration: 35.2% by Weight

A solution (G) prepared by mixing 142.4 g of acrylic acid, 1.75 g of trimethylolpropane triacrylate and 0.09 g of 2-hydroxy-2-methyl-1-phenyl-propan-1-one, and a solution (H) prepared by diluting 122.2 g of a 48.5 wt % aqueous solution of sodium hydroxide with 226.3 g of ion-exchanged water, and further adding 0.02 g of pentasodium diethylenetriamine pentaacetate, were respectively prepared, and then the solution (G) was mixed with the solution (H) under stirring with a magnetic stirrer while heat was removed from the solution (H) in an open system. Thus, a comparative aqueous monomer solution (5') at 30° C. was obtained.

Next, 0.6 g of a 30 wt % aqueous solution of polyoxyethylene sorbitan monostearate (manufactured by Kao Corp.) was added to the comparative aqueous monomer solution (5'), and the mixture was stirred. Thus, a comparative aqueous monomer solution (5) was obtained. The volume of 400 g of the comparative aqueous monomer solution (5) thus obtained was 360 ml. Thereafter, the aqueous monomer solution was further degassed for 20 minutes with nitrogen gas.

Subsequently, 6.6 g of a 3.0 wt % aqueous solution of 2,2'-azobis(2-methylpropionamidine) dihydrochloride was added thereto, and then the comparative aqueous monomer solution (5) and nitrogen gas were fluid mixed by using a desktop whip cream machine "Whip Auto (trade name)" in the same manner as in Example 1 to disperse gas bubbles of nitrogen gas in the comparative aqueous monomer solution (5) (monomer concentration: 35.2% by weight). Furthermore, the volume of 400 g of the comparative aqueous monomer solution (5) having nitrogen gas dispersed therein was 500 ml, and the volumetric expansion factor of the comparative aqueous monomer solution (5) in Comparative Example 5 was 1.4 times (=500 ml/360 ml).

Subsequently, 400 g of the aqueous monomer solution (5) that had passed through the Whip Auto was introduced into a vat type container made of stainless steel used in Example 1 that had been heated in advance to 90° C. with a hot plate in a system exposed to the atmosphere. Thereafter, a polymerization reaction was immediately initiated by performing UV irradiation by using a black light mercury lamp in the same manner as in Example 1. The temperature of this comparative aqueous monomer solution (5) at the time of initiation of polymerization was 30° C.

However, immediately after the comparative aqueous monomer solution (5) was introduced into the vat type container made of stainless steel, it was recognized that integration of gas bubbles progressed, and anti-foaming occurred. Furthermore, anti-foaming further progressed along with an increase in the temperature.

At the time point where the UV irradiation had been conducted for 3 minutes, the comparative polymer (5) was removed from the vat type container made of stainless steel. However, a white foam-like gel caused by gas bubbles such as in the cases of Examples 1 to 5 was not formed, and since the gel did not contain gas bubbles, the gel was almost transparent. From the record of change in the temperature of the polymerization system, the maximum arrival temperature at the time of polymerization was 92° C. (after about 120 seconds from the initiation of polymerization).

Next, in order to check the condition from a SEM (scanning electron microscope) photographic image, the comparative polymer (5) was cut with a knife into a cube which measured 5 mm on each side, and the cut comparative polymer was subjected to the same hot air drying as that carried out in Example 1. Thus, a comparative water absorbent resin dried product (5') was obtained.

During the drying step, since the comparative polymer (5) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying. The comparative water absorbent resin dried product (5') thus obtained was cut, and a SEM (scanning electron microscope) photographic image for the fractured surface was observed. However, continuous gas bubbles were not recognized.

Comparative Example 6

Additional Test of Patent Literature 22

Polymerization was carried out according to Example 18 of the Patent Literature 22 (U.S. Pat. No. 6,107,358) described above.

That is, a comparative aqueous monomer solution (6) was prepared by mixing 306 g of acrylic acid, 3240 g of 37 wt % sodium acrylate, 8.2 g of polyethylene glycol (n=8) diacrylate, 0.3 g of polyoxyethylene sorbitan monostearate (manufactured by Kao Corp.), 1420 g of pure water, and 10 g of a 10 wt % aqueous solution of sodium persulfate.

Subsequently, the comparative aqueous monomer solution (6) and nitrogen gas were fluid mixed by using a desktop whip cream machine "Whip Auto (trade name)" in the same manner as in Example 1 to disperse gas bubbles of nitrogen gas in the comparative aqueous monomer solution (6). Furthermore, the volumetric expansion factor of the comparative aqueous monomer solution (6) obtained after the aqueous monomer solution was passed through the Whip Auto (trade name) was 1.2 times.

Subsequently, 10 g of a 10 wt % aqueous sulfurous acid was added thereto, and polymerization was initiated at a monomer concentration of 30.2% by weight. This polymerization mode was static polymerization for one hour at a temperature of 25° C. to 95° C. (maximum arrival temperature: 95° C. (after 15 minutes from the initiation of polymerization), and polymerization was initiated 7 minutes after the supply to the polymerization apparatus), a sponge-like comparative polymer (6) containing a large amount of gas bubbles was obtained.

Next, in order to check the condition from a SEM (scanning electron microscope) photographic image, the comparative polymer (6) was cut with a knife into a cube which measured 5 mm on each side, and the cut comparative polymer was subjected to the same hot air drying as that carried out in Example 1. Thus, a comparative water absorbent resin dried product (6') was obtained.

During the drying step, since the comparative polymer (6) (5-mm piece) did not contain continuous gas bubbles, evaporation of vapor from the inside was difficult, and as drying progressed, gel expansion was recognized. Thus, there was a balloon-like deformation with a size of about 1 to several centimeters (cm) after the drying. The comparative water absorbent resin dried product (6') thus obtained was cut, and a SEM (scanning electron microscope) photographic image for the fractured surface was observed. However, continuous gas bubbles were not recognized, and it was confirmed that there were many independent gas bubbles.

Comparative Example 7

Additional Test of Patent Literature 20

Polymerization was carried out according to Example 2 of the Patent Literature 20 (U.S. Pat. No. 6,136,873). Meanwhile, Patent Literature 20 describes that "the polymerization temperature is preferably adjusted such that boiling of the polymerizable aqueous mixture can be avoided."

That is, a comparative aqueous monomer solution (7) was obtained by dissolving 2.00 g of trimethylolpropane triacrylate in 38.1 g of acrylic acid, subsequently adding 400.0 g of 37.3 wt % sodium acrylate and 10.00 g of a sodium salt of C13/C15-oxo alcohol sulfuric acid semiester thereto while stirring, and stirring the mixture for 5 hours. Thereafter, the system was stirred while nitrogen bubbling was carried out by using a commercially available cooking machine (BRAUN Multiquick Professional).

Subsequently, 21.22 g of a 3.0 wt % aqueous solution of 2,2-azobis-(N,N-dimethyleneisobutylamine) dihydrochloride was added thereto, and the resulting mixture was stirred for 5 minutes. Meanwhile, the volumetric expansion factor of the comparative aqueous monomer solution (7) obtained after the incorporation of gas bubbles was 8 times.

Thereafter, the comparative aqueous monomer solution (7) was introduced into a container made of polypropylene (dimension: 15 cm×19 cm×18 cm), but the rate of anti-foaming was fast, and at the time point of irradiating microwaves, the volume of the comparative aqueous monomer solution (7) decreased to almost a half. Irradiation of microwaves was further continued, but it was confirmed that anti-foaming further progressed. Meanwhile, in Comparative Example 7, the polymerization temperature was adjusted so as to avoid boiling of the comparative aqueous monomer solution (7).

A the time point when irradiation of microwaves had been carried out for 10 minutes, the comparative polymer (7) was removed from the container, but a foam-like polymer such as defined by the present invention was not obtained.

Comparative Example 8

Additional Test of Patent Literature 28

Polymerization was carried out according to Example 1 of the Patent Literature 28 (JP 1-318021 A).

That is, 0.08 parts by weight of methylenebisacrylamide and 0.1 parts by weight of polyoxyethylene (20) stearyl ether were added to 90 parts by weight of a 80 wt % aqueous solution of acrylic acid, and while the mixture was vigorously stirred in a nitrogen gas stream, 71 parts by weight of a 42 wt % aqueous solution of caustic soda was slowly added thereto. After cooling, 0.15 parts by weight of ammonium persulfate was dissolved therein, and thus a comparative monomer dispersion liquid (8) in which fine precipitates of acrylic acid sodium salt were uniformly dispersed was obtained. The comparative monomer dispersion liquid (8) was a slurry stock solution at a neutralization rate of 75% by mole and a monomer concentration of 54.9% by weight.

Next, the comparative monomer dispersion liquid (8) was flow cast into a layer having a thickness of about 2 cm in a polymerization vessel that had been purged with nitrogen, and the polymerization vessel was heated through the bottom. Polymerization started immediately after heating, and polymerization was associated with uniform foaming. Thus, a foamed rubber plate-like polymerization product having a thickness of about 5 cm was obtained in 20 minutes.

The polymerization product obtained by the operation described above has no tackiness, and the polymerization product was cut to a thickness of 5 mm by using a slicer to obtain a sheet form. Furthermore, the sheet was cut to squares which measured 5 mm on each side, and the squares were molded into pellets. Subsequently, the pellets were dried to obtain a comparative water absorbent resin dried product (8). The comparative water absorbent resin dried product (8) was cut, and a SEM (scanning electron microscope) photographic image for the fractured surface was observed. However, continuous gas bubbles were not recognized.

TABLE 1

| | Water absorbent resin powder | | | | | |
|---|---|---|---|---|---|---|
| | Open gas bubble ratio [%] | Independent gas bubble ratio [%] | D50 [μm] | FSR [g/g/s] | CRC [g/g] | Solids content [wt %] |
| Example 1 | 6.0 | 16 | 460 | 0.58 | 34.7 | 96.4 |
| Example 2 | 6.0 | 13 | 460 | 0.59 | 34.6 | 96.5 |
| Example 3 | 5.0 | 10 | 430 | 0.45 | 34.3 | 96.1 |
| Example 4 | 5.0 | 9.0 | 440 | 0.42 | 34.5 | 96.1 |
| Comparative Example 2 | 1.5 | 4.0 | 470 | 0.17 | 34.0 | 95.2 |
| Comparative Example 4 | 2.0 | 5.0 | 470 | 0.18 | 34.5 | 95.1 |

(Conclusions)

From a comparison of Example 1 and the like with the Comparative Examples, it is understood that it is important to satisfy the three requirements of "the volumetric expansion factor exceeds 1.1 times," "the monomer concentration is 40% by weight or greater," and "the maximum arrival temperature at the time of polymerization is 100° C. or higher," in order to obtain a water absorbent resin having a high water absorption rate (FSR).

That is, as disclosed in Comparative Example 1 (monomer concentration: 37.3% by weight), Comparative Example 5 (monomer concentration: 35.2% by weight), Comparative Example 2 and Comparative Example 3 (volumetric expansion factor: 1.0 times), Comparative Example 4 (temperature at the time of polymerization: 60° C. to 80° C.), Comparative Example 8 (slurry/non-aqueous solution) and the like, it is understood that if all the three constituent requirements of the present invention are not satisfied, continuous gas bubbles may not be obtained, or the continuous gas bubble ratio is less than 5%, so that a high water absorption rate may not be achieved.

Also, for Comparative Example 6 or Comparative Example 7 as related art technologies, it is understood that continuous gas bubbles are not formed. Furthermore, it is understood that in the method of the present invention, as the solids content (wt %) is higher, the rate of drying of the hydro gel is improved (shortened drying time).

As described in the above section (2-3), the "avoidance of boiling at the time of polymerization" that is recommended in Patent Literatures 8, 20, 21, 30 to 33 and the like is accompanied by a decrease in productivity, expensive cooling facilities, and the like. However, in the present invention, the boiling polymerization that has been conventionally avoided in the method for producing a (continuous) foam-like water absorbent resin, efficiently provides continuous gas bubbles at a monomer concentration of 40% by weight or greater and a volumetric expansion factor of 1.1 times or greater.

EXAMPLE 6

Monomer Concentration; 45.4% by Weight, MQ: 70 ppm

A solution (I) prepared by mixing 190.18 g of acrylic acid, 0.83 g of polyethylene glycol diacrylate (number average molecular weight: 522), and 0.11 g of 2-hydroxy-2-methyl-1-phenyl-propan-1-one, and a solution (J) prepared by diluting 130.60 g of a 48.5 wt % aqueous solution of sodium hydroxide with 163.46 g of ion-exchanged water, and further adding 0.02 g of pentasodium diethylenetriamine pentaacetate, were respectively prepared, and then the solution (I) was mixed with the solution (J) under stirring with a magnetic stirrer while heat was removed from the solution (J) in an open system. Thus, an aqueous monomer solution (6') at 45° C. was obtained. Meanwhile, acrylic acid in which the content of p-methoxyphenol (hereinafter, may be simply referred to as "MQ") was adjusted to 70 ppm was used.

Next, 3.75 g of a 30 wt % aqueous solution of polyoxyethylene sorbitan monostearate (manufactured by Kao Corp.) and 2.25 g of hydroxyethyl cellulose (Wako First Grade/manufactured by Wako Pure Chemical Industries, Ltd.) were added to the aqueous monomer solution (6'), and the mixture was stirred. Thus, an aqueous monomer solution (6) (content of p-methoxyphenol: 70 ppm (relative to acrylic acid)) was obtained. The volume of 400 g of the aqueous monomer solution (6) thus obtained was 340 ml. Thereafter, the aqueous monomer solution was further degassed for 20 minutes with nitrogen gas.

Subsequently, 8.8 g of a 3.0 wt % aqueous solution of 2,2'-azobis(2-methylpropionamidine) dihydrochloride was added thereto, and then the aqueous monomer solution (6) and nitrogen gas were fluid mixed by using a desktop whip cream machine "Whip Auto (trade name)" in the same manner as in Example 1 to disperse gas bubbles of nitrogen gas in the aqueous monomer solution (6) (monomer concentration: 45.4% by weight). Furthermore, the volume of 400 g of the aqueous monomer solution (6) having nitrogen gas dispersed therein was 850 ml, and the volumetric expansion factor of the aqueous monomer solution (6) in Example 6 was 2.5 times (=850 ml/340 ml).

Subsequently, 400 g of the aqueous monomer solution (6) that had passed through the Whip Auto was introduced into a vat type container made of stainless steel that was used in Example 1 and had been heated in advance to 90° C. with a hot plate in a system exposed to the atmosphere. Thereafter, a polymerization reaction was immediately initiated by performing UV irradiation by using a black light mercury lamp in the same manner as in Example 1.

During the polymerization reaction, water vapor was generated after about 40 seconds from the initiation of polymerization, and the reaction proceeded under boiling at or above 100° C. The foamed polymer (6) as a white foam-like gel thus obtained in the boiling polymerization underwent slight volumetric expansion as in the case of Example 1, but there was almost no volumetric change. Meanwhile, the temperature of the aqueous monomer solution (6) at the time of initiation of polymerization was 42° C. due to heating from the hot plate, or the like. However, thereafter, the temperature increased rapidly as polymerization proceeded, and after about 50 seconds from the initiation of polymerization, the maximum arrival temperature recorded 102° C.

At the time point where the UV irradiation had been conducted for 3 minutes, the foamed polymer (6) was removed from the vat type container made of stainless steel, and the open gas bubble ratio and the independent gas bubble ratio were measured and calculated. The open gas bubble ratio was 53%, and the independent gas bubble ratio was 8%. Meanwhile, the foamed polymer (6) had numerous fine gas bubbles, and formed a steamed bun-like white foam gel due to the gas bubbles.

Next, in order to check the condition from a SEM (scanning electron microscope) photographic image, the foamed polymer (6) was cut with a knife into a cube which measured 5 mm on each side, and the cut foamed polymer was subjected to the same hot air drying as that carried out in Example 1. Thus, a water absorbent resin dried product (6') was obtained.

During the drying step, gel expansion was not observed, and deformation did not occur as in the case of the drying of the foamed polymer (1) in Example 1. The water absorbent resin dried product (6') thus obtained was cut, and a SEM (scanning electron microscope) photographic image for the fractured surface was observed. It was found that continuous gas bubbles had been formed.

Next, separately, the foamed polymer (6) obtained by the operation described above was cut with a knife into a cube which measured 2 mm on each side, and the cut foamed polymer was subjected to the same hot air drying as that carried out in Example 1. Thus, a cube-shaped water absorbent resin dried product (6) was obtained. Thereafter, the water absorbent resin dried product (6) was further subjected to the same pulverization and classification steps as those carried out in Example 1. Thereby, a water absorbent resin powder (6) having a weight average particle diameter (D50) of 460 μm was obtained. Various physical properties of the water absorbent resin powder (6) thus obtained are presented in Table 1. Furthermore, the open gas bubble ratio of the water absorbent resin powder (6) was 15%, and the independent gas bubble ratio was 24%. Also, the p-methoxyphenol content in the water absorbent resin powder (6) was 20 ppm.

EXAMPLE 7

MQ: 120 ppm

The same operation as that carried out in Example 6 was carried out, except that as compared to Example 6, acrylic acid in which the content of p-methoxyphenol (MQ) was adjusted to 120 ppm was used. Thus, a foamed polymer (7) was obtained. The foamed polymer (7) was further subjected to the same operation as that used in Example 6, and thus a water absorbent resin powder (7) having a weight average particle diameter (D50) of 460 μm was obtained. Various physical properties of the water absorbent resin powder (7) thus obtained are presented in Table 1. Furthermore, the open gas bubble ratio of the water absorbent resin powder (7) was 13%, and the independent gas bubble ratio was 23%. Furthermore, the p-methoxyphenol content in the water absorbent resin powder (7) was 35 ppm.

EXAMPLE 8

MQ: 200 ppm

The same operation as that carried out in Example 6 was carried out, except that as compared to Example 6, acrylic acid in which the content of p-methoxyphenol (MQ) was adjusted to 200 ppm was used. Thus, a foamed polymer (8) was obtained. The foamed polymer (8) was further subjected to the same operation as that used in Example 6, and thus a water absorbent resin powder (8) having a weight average particle diameter (D50) of 450 μm was obtained. Various physical properties of the water absorbent resin powder (8) thus obtained are presented in Table 1. Furthermore, the open gas bubble ratio of the water absorbent resin powder (8) was 13%, and the independent gas bubble ratio was 21%. Furthermore, the p-methoxyphenol content in the water absorbent resin powder (8) was 56 ppm.

EXAMPLE 9

MQ: 250 ppm

The same operation as that carried out in Example 6 was carried out, except that as compared to Example 6, acrylic acid in which the content of p-methoxyphenol (MQ) was adjusted to 250 ppm was used. Thus, a foamed polymer (9) was obtained. The foamed polymer (9) was further subjected to the same operation as that used in Example 6, and thus a water absorbent resin powder (9) having a weight average particle diameter (D50) of 460 μm was obtained. Various physical properties of the water absorbent resin powder (9) thus obtained are presented in Table 1. Furthermore, the open gas bubble ratio of the water absorbent resin powder (9) was 14%, and the independent gas bubble ratio was 22%. Furthermore, the p-methoxyphenol content in the water absorbent resin powder (9) was 67 ppm.

Comparative Example 9

Volumetric Expansion Factor: 1.0 Times, MQ: 70 ppm

The same operation as that carried out in Example 6 was carried out, except that as compared with Example 6, a comparative aqueous monomer solution (9) (volumetric expansion factor: 1.0 times) was obtained without using polyoxyethylene sorbitan monostearate and hydroxyethyl cellulose, furthermore without using the Whip Auto, and without dispersing gas bubbles of nitrogen gas in the aqueous monomer solution. Thus, a comparative polymer (9) which was a transparent gel was obtained. Furthermore, the comparative polymer (9) was subjected to the same operation as that carried out in Example 6, and thus a comparative water absorbent resin powder (9) having a weight average particle diameter (D50) of 470 μm was obtained. Various physical properties of the comparative water absorbent resin powder (9) thus obtained are presented in Table 2. Furthermore, the open gas bubble ratio of the comparative water absorbent resin powder (9) was 1.3%, and the independent gas bubble ratio was 3%. Furthermore, the p-methoxyphenol content in the comparative water absorbent resin powder (9) was 20 ppm.

Comparative Example 10

Volumetric Expansion Factor: 1.0 Times, MQ: 120 ppm

The same operation as that carried out in Comparative Example 9 was carried out, except that as compared with Comparative Example 9, acrylic acid in which the content of p-methoxyphenol was adjusted to 120 ppm was used. Thus, a comparative water absorbent resin powder (10) having a weight average particle diameter (D50) of 470 μm was obtained. Various physical properties of the comparative water absorbent resin powder (10) thus obtained are presented in Table 1. Furthermore, the open gas bubble ratio of the comparative water absorbent resin powder (10) was 1.5%, and the independent gas bubble ratio was 3.5%. Furthermore, the p-methoxyphenol content in the comparative water absorbent resin powder (10) was 36 ppm.

Comparative Example 11

Volumetric Expansion Factor: 1.0 Times, MQ: 200 ppm

The same operation as that carried out in Comparative Example 9 was carried out, except that as compared with Comparative Example 9, acrylic acid in which the content of p-methoxyphenol was adjusted to 200 ppm was used. Thus, a comparative water absorbent resin powder (11) having a weight average particle diameter (D50) of 480 μm was obtained. Various physical properties of the comparative water absorbent resin powder (11) thus obtained are presented in Table 1. Furthermore, the open gas bubble ratio of the comparative water absorbent resin powder (11) was 2.1%, and the independent gas bubble ratio was 3.1%. Furthermore, the p-methoxyphenol content in the comparative water absorbent resin powder (11) was 55 ppm.

Comparative Example 12

Volumetric Expansion Factor: 1.0 Times, MQ: 250 ppm

The same operation as that carried out in Comparative Example 9 was carried out, except that as compared with Comparative Example 9, acrylic acid in which the content of p-methoxyphenol was adjusted to 250 ppm was used. Thus, a comparative water absorbent resin powder (12) having a weight average particle diameter (D50) of 460 μm was obtained. Various physical properties of the comparative water absorbent resin powder (12) thus obtained are presented in Table 2. Furthermore, the open gas bubble ratio of the comparative water absorbent resin powder (12) was 1.8%, and the independent gas bubble ratio was 2.8%. Furthermore, the p-methoxyphenol content in the comparative water absorbent resin powder (12) was 68 ppm.

TABLE 2

| | Water absorbent resin powder | | | | | | | | |
|---|---|---|---|---|---|---|---|---|---|
| | Open gas bubble ratio [%] | Independent gas bubble ratio [%] | D50 [μm] | FSR [g/g/s] | CRC [g/g] | Solids content [wt %] | Initial color tone | | |
| | | | | | | | L [—] | a [—] | b [—] |
| Example 6 | 15 | 24 | 460 | 0.70 | 34.5 | 96.8 | 91.8 | −1.5 | 8.3 |
| Example 7 | 13 | 23 | 460 | 0.68 | 34.0 | 96.5 | 91.4 | −1.5 | 10.2 |
| Example 8 | 13 | 21 | 450 | 0.67 | 34.4 | 96.5 | 90.3 | −1.3 | 11.3 |
| Example 9 | 14 | 22 | 460 | 0.67 | 34.2 | 96.5 | 86.4 | −1.1 | 15.5 |
| Comparative Example 9 | 1.3 | 3.0 | 470 | 0.17 | 33.8 | 95.2 | 91.6 | −1.5 | 8.6 |
| Comparative Example 10 | 1.5 | 3.5 | 470 | 0.18 | 34.0 | 95.1 | 90.1 | −1.4 | 11.6 |

TABLE 2-continued

<table>
<tr><td colspan="9">Water absorbent resin powder</td></tr>
<tr><td></td><td>Open gas bubble ratio [%]</td><td>Independent gas bubble ratio [%]</td><td>D50 [μm]</td><td>FSR [g/g/s]</td><td>CRC [g/g]</td><td>Solids content [wt %]</td><td colspan="3">Initial color tone</td></tr>
<tr><td></td><td></td><td></td><td></td><td></td><td></td><td></td><td>L [—]</td><td>a [—]</td><td>b [—]</td></tr>
<tr><td>Comparative Example 11</td><td>2.1</td><td>3.1</td><td>480</td><td>0.18</td><td>33.8</td><td>95.2</td><td>89.5</td><td>−1.3</td><td>14.5</td></tr>
<tr><td>Comparative Example 12</td><td>1.8</td><td>2.8</td><td>460</td><td>0.17</td><td>33.9</td><td>95.2</td><td>85.1</td><td>−1.2</td><td>17.6</td></tr>
</table>

(Conclusions) From a comparison of Examples 6 to 8 and Comparative Examples 9 to 13, it is understood that the content of p-methoxyphenol (MQ) in the water absorbent resin powder is important from the viewpoint of the initial coloration.

In the respective comparisons of Example 6 and Comparative Example 9 (MQ=70 ppm), Example 7 and Comparative Example 10 (MQ=120 ppm), Example 8 and Comparative Example 11 (MQ=200 ppm), and Example 9 and Comparative Example 12 (MQ=250 ppm), which respectively used the same amounts of MQ at the time of polymerization that is indicated in Table 2, the water absorption rate (FSR) drastically increased to 4 times in the method of the present invention. Furthermore, the water absorption capacity (CRC) also slightly improved, and the initial color hue was also improved (a larger L value, and smaller a value/b value). Furthermore, for the respective comparisons, it is understood that in the method of the present invention, as the solids content (wt %) is high, the rate of drying of the hydro gel is improved (shortened drying time).

The conventional methods for enhancing the water absorption rate as in Patent Literature 20 and the like do not disclose the prevention of coloration, and as compared with the conventional methods for preventing coloration as described in Patent Literature 29 and the like, the present invention is such that the water absorption rate (FSR) is significantly improved.

Comparative Example 13

Monomer Concentration: 37.3% by Weight

The same operation as that carried out in Example 6 was carried out, except that as compared with Example 6, the monomer concentration was adjusted to 37.3% by weight by changing the amount of ion-exchanged water used in the preparation of the aqueous monomer solution to 271.60 g. Thus, a comparative polymer (13) was obtained. At the time of polymerization, the maximum arrival temperature at the time of polymerization from the record of the change in the temperature of the polymerization system was 97° C. (after about 100 seconds from the initiation of polymerization).

Next, the comparative polymer (13) obtained by the operation described above was subjected to the same drying, pulverization and classification as those carried out in Example 6, and thus a comparative water absorbent resin powder (13) was obtained. The physical properties of the comparative water absorbent resin powder (13) thus obtained are presented in Table 3.

EXAMPLE 10

Monomer Concentration: 50.5% by Weight

The same operation as that carried out in Example 6 was carried out, except that as compared with Example 6, the monomer concentration was adjusted to 50.5% by weight by changing the amount of ion-exchanged water used in the preparation of the aqueous monomer solution to 113.49 g. Thus, a foamed polymer (10) was obtained. At the time of polymerization, the maximum arrival temperature at the time of polymerization from the record of change in the temperature of the polymerization system was 105° C. (after about 45 seconds from the initiation of polymerization).

Next, the foamed polymer (10) obtained by the operation described above was subjected to the same drying, pulverization and classification as those carried out in Example 6, and thus a water absorbent resin powder (10) was obtained. The physical properties of the water absorbent resin powder (10) thus obtained are presented in Table 3.

Comparative Example 14

Maximum Temperature: 98° C.

As compared with Example 6, the maximum arrival temperature at the time of polymerization was controlled to 98° C. (after about 50 seconds from the initiation of polymerization) by reinforcing cooling after the initiation of polymerization, and thus a comparative polymer (14) was obtained.

Next, the comparative polymer (14) obtained by the operation described above was subjected to the same drying, pulverization and classification as those carried out in Example 6, and thus a comparative water absorbent resin powder (14) was obtained. The physical properties of the comparative water absorbent resin powder (14) thus obtained are presented in Table 3.

Comparative Example 15

Volumetric Expansion Factor: 1.04

As compared with Example 6, the aqueous monomer solution (6) having a volumetric expansion factor of 2.5 times was left to stand for 10 minutes without any change so as to adjust the volumetric expansion factor to 1.04, and then the same polymerization as that carried out in Example 6 was carried out. Thus, a comparative polymer (15) was obtained. During the polymerization step, the maximum arrival temperature at the time of polymerization from the record of change in the temperature of the polymerization system was 102° C. (after about 50 seconds from the initiation of polymerization).

Next, the comparative polymer (15) obtained by the operation described above was subjected to the same drying, pulverization and classification as those carried out in Example 6, and thus a comparative water absorbent resin powder (15) was obtained. The physical properties of the comparative water absorbent resin powder (15) thus obtained are presented in Table 3.

TABLE 3

|  | Water absorbent resin powder | | | | |
| --- | --- | --- | --- | --- | --- |
|  | Open gas bubble ratio [%] | Independent gas bubble ratio [%] | FSR [g/g/s] | CRC [g/g] | Solids content [wt %] |
| Comparative Example 13 | 2.0 | 2.0 | 0.17 | 34.9 | 95.3 |
| Example 10 | 8.0 | 13 | 0.61 | 33.1 | 96.4 |
| Comparative Example 14 | 3.0 | 4.5 | 0.19 | 34.4 | 95.2 |
| Comparative Example 15 | 3.5 | 5.0 | 0.20 | 35.2 | 95.3 |

(Conclusions)

As indicated in Table 3, in Comparative Example 13 (monomer concentration: 37.3% by weight), Comparative Example 14 (maximum temperature: 98° C.), and Comparative Example 15 (1.04 times), each of which lacks one requirement as compared with Example 10 of the present invention (open gas bubble ratio=8.0%, FSR=0.61) which satisfied all the three requirements of the maximum polymerization temperature (100° C. or higher), the monomer concentration (40% by weight or greater), and the volumetric expansion factor (1.1 times or greater) as defined in the present application, the open gas bubble ratio was as low as 2.0% to 3.5%, and the water absorption rate (FSR) also decreased to ⅓ or less. Furthermore, it is understood that in the method of the present invention, as the solids content was (wt %) was higher, the rate of drying of the hydro gel improved (shortened drying time). It is understood from Table 3 that the three requirements are essential.

EXAMPLE 11

Drying Experiment

The foamed polymer (6) as a white foam-like gel obtained in Example 6 was cut to a size of 2 mm to 3 mm, and then the cut foamed polymer was mounted on a punching plate. Hot air at 180° C. having a dew point of 5° C. was blown at a velocity of 1.6 [m/s], upward from the lower part of the punching plate. At this time, the rate of drying was measured, and the drying time to reach a solids concentration of 95% by weight or greater was 20 minutes. Thus, it is understood that the rate of drying is fast in the method of the present invention.

Comparative Example 16

Drying Experiment

The comparative polymer (9) as a transparent gel obtained in Comparative Example 9 was cut to a size of 2 mm to 3 mm, and then the rate of drying was measured by the same method as in Example 11. The drying time to reach a solids concentration of 95% by weight or greater was 25 minutes.

EXAMPLE 12

Water Absorbent Sheet

The foamed polymer (6) as a white foam-like gel obtained in Example 6 was cut to a diameter of 90 mm, and thus a water absorbent sheet (12) (molded product) was obtained. For the water absorbent sheet (miniature absorbent core 12) thus obtained, the amount of re-wet was measured by the evaluation method described below, which is equivalent to an evaluation of disposable diapers. Here, the miniature absorbent core is a model of a disposable diaper and is an example of the water absorbing article of the present invention.

The miniature absorbent core 12 (diameter: 90 mm) was placed on the bottom of a Petri dish made of SUS and having an internal diameter of 90 mm, and a non-woven fabric having a diameter of 90 mm was mounted thereon. Further, a piston and a weight that had been adjusted such that a load of 4.8 kPa would be uniformly exerted on the miniature absorbent core 12, were placed. The piston and the weight used had a liquid feeding port having a diameter of 5 mm at the center.

Subsequently, 25 ml of physiological saline (0.9 wt % aqueous solution of sodium chloride) was poured in through the liquid feeding port to allow the miniature absorbent core 12 to absorb the liquid. After 30 minutes passed, 25 ml of physiological saline was further poured in through the liquid feeding port to allow the miniature absorbent core to absorb the liquid. After 30 minutes passed, the piston and the weight were removed, and 30 sheets of filter paper (manufactured by Toyo Roshi Kaisha, Ltd.; No. 2) having an external diameter of 90 mm, the total weight (W9 [g]) of which had been measured in advance, were mounted on the non-woven fabric, and the piston and the weight that exert a uniform load (total weight: 20 kg) were rapidly placed thereon. After 5 minutes passed, the weight of the 30 sheets of filter paper (W10 [g]) was measured, and the amount of liquid return [g] of the miniature absorbent core 12 was calculated according to the following formula. The amount of liquid return was 3.8 g.

Amount of re-wet (miniature absorbent core) [g]=$W10-W9$ [Formula 19]

Furthermore, the water absorbent sheet (12) also had excellent air permeability, and there was almost no feeling of stuffiness.

Comparative Example 17

Water Absorbent Sheet

The comparative polymer (9) as a transparent gel obtained in Comparative Example 9 was cut in the same manner as in Example 12, and thus a comparative water absorbent sheet (17) (molded product) was obtained. For the comparative water absorbent sheet (17) thus obtained, the amount of re-wet was measured in the same manner as in Example 12, and the amount of re-wet was 14.6 g. Furthermore, the comparative water absorbent sheet (17) had a large amount of re-wet, so that the comparative water absorbent sheet had poor air permeability and a heavy feeling of stuffiness.

(Conclusions)

From a comparison of Comparative Example 17 and Example 12, it is understood that the water absorbent resin of the present invention provides an excellent water absorbing article (particularly, a hygiene material such as a disposable diaper) exhibiting less return of urine and excellent air permeability, but without stuffiness.

INDUSTRIAL APPLICABILITY

A water absorbent resin having a high water absorption rate can be conveniently obtained, and such a water absorbent resin can be widely utilized, including hygiene materials such as disposable diapers.

The present patent application is based on JP 2010-149907 A filed Jun. 30, 2010, the entire disclosure of which is incorporated herein by reference.

REFERENCE SIGNS LIST

1 TANK
2 MIXING ZONE
3 SURFACE ASPERITY
4 AQUEOUS MONOMER SOLUTION
5 GAS
6 ASPIRATOR
7 GAS BUBBLE-CONTAINING AQUEOUS MONOMER SOLUTION
8 MONOMER PREPARATION TANK
9 PUMP

The invention claimed is:

1. A polyacrylic acid-type water absorbent resin having an open gas bubble ratio of 5% or greater and the content of p-methoxyphenol is 60 ppm or less.

2. The water absorbent resin according to claim 1, wherein the independent gas bubble ratio is 5% or greater.

3. The water absorbent resin according to claim 1, comprising at least any one of a metal chelating agent and a reducing agent.

4. The water absorbent resin according to claim 1, wherein the water absorption rate (FSR) is 0.25 [g/g/s] or greater.

5. The water absorbent resin according to claim 1, wherein the water absorbent resin is surface-crosslinked by using a covalently bondable crosslinking agent and/or an ionically bondable crosslinking agent.

6. The water absorbent resin according to claim 1, which is in a sheet form.

7. The water absorbent resin according to claim 1, wherein the water absorbent resin is in the form of a powder having a weight average particle diameter (D50) of greater than or equal to 300 μm and less than 600 μm.

8. A water absorbing article comprising the water absorbent resin according to claim 1.

* * * * *